United States Patent
Freire et al.

(10) Patent No.: US 7,183,267 B2
(45) Date of Patent: Feb. 27, 2007

(54) β-LACTAMASE INHIBITORS AND METHODS OF USE THEREOF

(75) Inventors: Ernesto Freire, Baltimore, MD (US); Patrick Ross, Baltimore, MD (US); Yingxin Xiao, Gaithersburg, MD (US); Raphael Ottenbrite, Midlothian, VA (US); Irene Luque, Granada (ES)

(73) Assignees: The Johns Hopkins University, Baltimore, MD (US); Fulcrum Pharmaceuticals Inc., Las Vagas, NV (US)

( * ) Notice: Subject to any disclaimer, the term of this patent is extended or adjusted under 35 U.S.C. 154(b) by 0 days.

(21) Appl. No.: 10/866,179

(22) Filed: Jun. 10, 2004

(65) Prior Publication Data

US 2005/0124580 A1    Jun. 9, 2005

Related U.S. Application Data

(60) Provisional application No. 60/477,636, filed on Jun. 10, 2003.

(51) Int. Cl.
*A61K 31/69* (2006.01)
*C07F 5/02* (2006.01)

(52) U.S. Cl. .................... 514/64; 568/3; 560/8
(58) Field of Classification Search ............ 514/64, 514/512, 576; 560/22, 8; 568/1, 3; 558/288, 558/286
See application file for complete search history.

(56) References Cited

U.S. PATENT DOCUMENTS 6,075,014 A    6/2000    Weston et al.
6,417,174 B1   7/2002    Shoichet et al.

*Primary Examiner*—Joseph K. McKane
*Assistant Examiner*—Yong Chu
(74) *Attorney, Agent, or Firm*—Darby & Darby

(57) ABSTRACT

The invention provides novel non-β-lactam inhibitors of β-lactamases. In particular, the invention provides boronic acid-based compounds set forth in the specification. These compounds may be used with β-lactam antibiotics to bacterial infection, particularly, β-lactam-antibiotic-resistant bacterial infections. These compounds are also antibacterial agents by themselves. The invention further provides methods of using such compounds. Finally, the invention provides a pharmaceutical composition comprising these compounds.

21 Claims, No Drawings

β-LACTAMASE INHIBITORS AND METHODS OF USE THEREOF

CROSS REFERENCE TO RELATED APPLICATIONS

The present application claims priority under 35 U.S.C. § 119(e) of provisional application 60/477,636, filed Jun. 10, 2003, which is hereby incorporated herein by reference in its entirety.

FIELD OF THE INVENTION

The present invention relates to inhibitors of β-lactamase and methods of use thereof. Specifically, the invention relates to non-β-lactam-based inhibitors of β-lactamase.

BACKGROUND OF THE INVENTION

Drug resistance to antibiotics, especially β-lactam antibiotics such as penicillin, cephalosporin and related compounds is one of the most serious problems in the treatment of infectious diseases (Neu, *Science*, 257, 1064–1073 (1992)). It represents not only a significant medical problem but a major public health and economic burden. Between 1980 and 1992, the death rate, due to infectious diseases as the underlying cause of death, increased 58%, from 41 to 65 deaths per 100,000 population in the U.S. Age adjusted mortality from infectious diseases increased 39% during the same period. Infectious disease mortality increased 25% among those aged 65 years and older (from 271 to 338 per 100,000) and 6.3 times among 25–44 year olds (from 6 to 38 per 100,000). Mortality due to respiratory tract infections increased 20% (from 25 to 30 deaths per 100,000). Reports from the Center for Disease Control (CDC) indicate that two million Americans acquire infections in hospitals each year, the cost of which runs to an estimated $4.5 billion. Of these infections, 70% are due to microbes that are resistant to one or more antibiotics and in 30–40% of the infections the causative microbe is resistant to first line treatment. The rate at which patients acquire infections in hospitals rose by 36% in 1995 compared with 1975. In 1995, 35.9 million patients entered hospitals in the U.S. compared with 37.7 million patients in 1975. For the same period, lengths of hosptial stays dropped to an average of 5.3 days from 7.9 days due to managed health care guidelines. However, the number of infections per 1,000 patient days rose to 9.77 from 7.18.

Without being limited to any particular theory or mechanism of action, it is believed that evolutionary selection and genetic transformation have made this problem pressing. Most antibiotic drugs are derivatives of naturally occurring bactericides (Davies, *Science*, 264, 375–382 (1994)), and many resistance mechanisms evolved long ago. Human use of antibiotics has refined these mechanisms and promoted their spread through gene transfer (Davies, *Science*, 264, 375–382 (1994)). A resistance mechanism originating in one species of bacteria can be expected to spread throughout the biosphere.

β-lactam antibiotics inhibit bacterial cell wall biosynthesis (Tomasz, *Rev. Infect. Dis.*, 8, S270–S278 (1986)). They form covalent complexes with and consequently inactivate a group of transpeptidases/carboxypeptidases called the Penicillin Binding Proteins (PBPs). PBP inactivation disrupts cell wall biosynthesis, leading to self-lysis and death of the bacteria. β-lactam antibiotics have been widely prescribed. In the absence of resistance, β-lactams are the first choice for treatment in 45 of 78 common bacterial infections (Goodman & Gilman's *The Pharmacological Basis of Therapeutics* (Hardman et al., eds., McGraw-Hill, New York, 1996)).

Bacterial adaptations to β-lactam drugs (e.g., amoxicillin, cephalothin, clavulanate, and aztreonam) are among the best studied and most pernicious forms of antibiotic resistance. Without being limited to any particular theory or mechanism of action, it is believed that bacteria use several different mechanisms to escape from β-lactam antibiotics (Sanders, *Clinical Infectious Disease,* 14, 1089–1099 (1992); Li et al., *Antimicrob. Agents Chemother.*, 39, 1948–1953 (1995)). Probably the most widespread is the hydrolysis of β-lactams by β-lactamase enzymes.

β-lactamases are endogenous bacterial enzymes that destroy β-lactam antibiotics and eliminate their efficacy. The name derives from their ability to cleave the β-lactam ring. The structures of many β-lactamases are known at the atomic level and available in the protein database. At least four classes of β-lactamases are known: Classes A, B, C and D. At the clinical level, the most important β-lactamases belong to Class A (TEM) and Class C (AmpC). TEM and Amp-C are serine hydrolases and have a critical serine in their catalytic site. TEM and AmpC) among different bacterial species share high sequence identity and structural similarity (Galleni, et al., *Biochem. J.,* 250, 753–760 (1988); Galleni, et al., *Biochem. J.,* 250, 753–760 (1988); Usher et al., *Biochemistry,* 30, 16082–16092 (1998)).

One way to overcome the negative effects of β-lactamases is to use molecules that neutralize the action of β-lactamase (known as β-lactamase inhibitors or inhibitors of β-lactamase) in combination with antibiotics. The three β-lactamase inhibitors currently in clinical use (clavulanic acid, sulbactam and tazobactam) are all transition state analogs that utilize the same β-lactam core that is present in the antibiotics themselves.

The similarity between the β-lactam antibiotics and β-lactam-based β-lactam-based β-inhibitors has proven to be a serious problem. Resistance to such β-lactam-based β-lactamase inhibitors arises through modifications of previously susceptible mechanisms. Certain mutations in β-lactamase, for example, reduce the effectiveness of β-lactam-based β-lactamase inhibitors while preserving the ability of the β-lactamase to hydrolyze the antibiotic molecules. Certain point substitutions in β-lactamases allow the enzymes to hydrolyze compounds designed to evade them (Philippon et al., *Antimicrob. Agents Chemother.*, 33, 1131–1136 (1989)). Other substitutions reduce the affinity of β-lactam inhibitors for the enzymes (Saves, et al., *J. Biol. Chem.*, 270, 18240–18245 (1995)) or allow the enzymes to simply hydrolyze them. Furthermore, several gram-positive bacteria (e.g., *Staph. Aureus*) have acquired sensor proteins that detect β-lactams in the environment of the cell (Bennet and Chopra, *Antimicrob. Agents Chemotherapy,* 37, 153–158 (1993)). β-lactam binding to these sensors leads to transcriptional up-regulation of the β-lactamase. β-lactam-based β-lactamase inhibitors, thus, can induce the production of the enzyme that they are meant to inhibit, preventing or reducing their efficacy.

Without being limited to any particular theory or mechanism of action, it is believed that one reason that bacteria have been able to respond rapidly with "new" resistance mechanisms to β-lactam-based inhibitors is that the mechanisms of action of the inhibitors are not, in fact, new, because β-lactamases have evolved mechanisms for, e.g., sensing and/or hydrolyzing such molecules. Accordingly, as long as medicinal chemistry focuses on β-lactam-based molecules to overcome β-lactamases, resistance can be expected to follow shortly.

One way to avoid recapitulating this "arms race" between bacteria and β-lactams is to develop non-β-lactam inhibitors that have novel chemistries and are dissimilar to β-lactams. Such non-β-lactam inhibitors would not themselves be degraded by β-lactamases, and mutations in the enzymes would not be expected render such inhibitors labile to hydrolysis. Such novel inhibitors would also escape detection by β-lactam sensor proteins that up-regulate β-lactamase transcription, and may be unaffected by porin mutations that limit the access of β-lactams to PBPs. Such inhibitors would allow the current β-lactam antibiotics to effectively work against bacteria where β-lactamases provide the dominant resistance mechanism.

It has previously been reported that boric acid and certain phenyl boronic acids are inhibitors of certain β-lactamases (Koehler and Lienhard, (1971); Kiener and Waley, *Biochem. J.*, 169, 197–204 (1978) (boric acid, phenylboronic acid and m-aminophenylboronate); Beesley et al., *Biochem. J.*, 209, 229–233 (1983) (twelve substituted phenylborinic acids, including 2-formylphenylboronate, 4-formylphenylboronate, and 4-methylphenylboronate; and Amicosante et al., *J. Chemotherapy*, 1, 394–398 (1989) (boric acid, phenylboronic acid, m-aminophenylboronate and tetraphenylboronic acid)). m-(dansylamidophenyl)-boronic acid has been reported to inhibitor of the *Enterobacter cloacae* P99 β-lactamase (Dryjanski and Pratt, *Biochemistry*, 34, 3561–3568 (1995)). In addition, Strynadka and colleagues used the crystallographic structure of a mutant TEM-1 enzyme-penicillin G complex to design a novel alkylboronic acid inhibitor [(1R)-1-acetamido-2-(3-carboxyphenyl)ethane boronic acid] with high affinity for this enzyme. (Strynadka et al., *Nat. Struc. Biol.*, 3, 688–695 (1996)).

Additional boronic acid-based compounds with demonstrated or potential ability to inhibit b-lactamases have been reported in Tondi et al. (*Chemistry & Biology*, 8, 593–610 (2001), Martin et al. (*Bioorganic & Medicinal Chemistry Letters*, 4(10), 1229–1234 (1994), Weston et al. (*J. Med. Chem.*, 41, 4577–4586 (1998) and U.S. Pat. Nos. 6,075,014 and 6,184,363.

Many of the compounds described above are peptide derivatives or peptidyl mimetics which are not desirable as orally available pharmaceutical drugs due to their rapid degradation by digestive enzymes (Ness et al, 2000; Morandi et al, 2003, Rudgers et al, 2001).

Hence, there remains a need for new non-β-lactam-based β-lactamase inhibitors that are active against a wide variety of β-lactamases, particularly those that are resistant to clavulanic acid, sulbactam and tazobactam.

Citation or identification of any references in the "Background of the Invention" or anywhere in the specification of this application is not an admission that such references available as prior art to the present invention.

SUMMARY OF THE INVENTION

The present invention provides compounds having the formula (A):

(HO)$_2$—B-T    (A)

wherein

B stands for boron, and

T has one of the following structures:

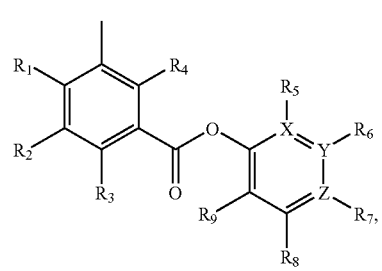

(I)

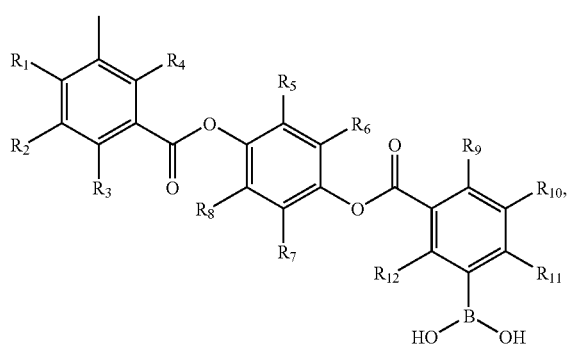

(II)

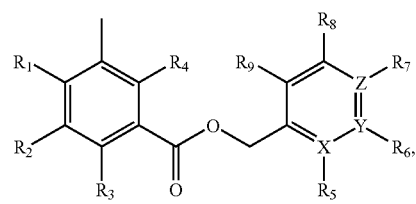

(III)

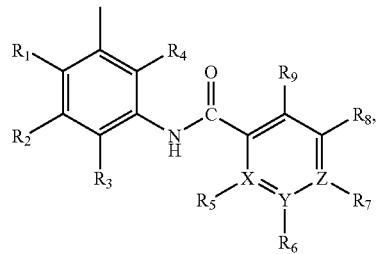

(IV)

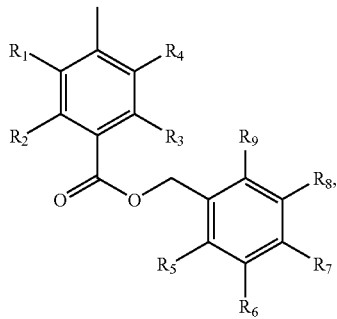

(V)

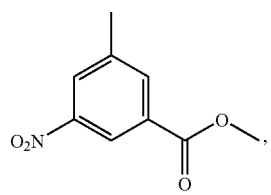

(VI)

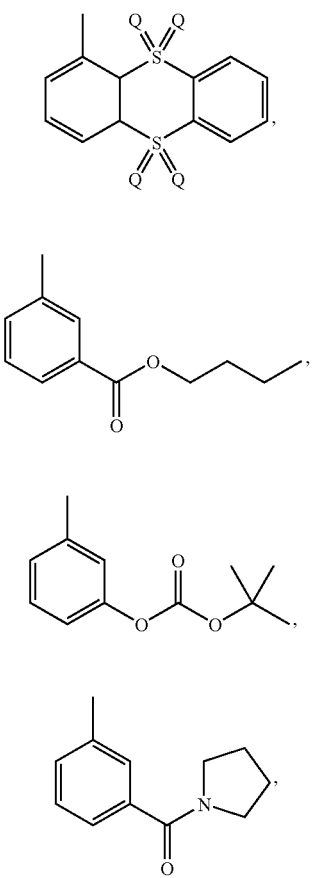

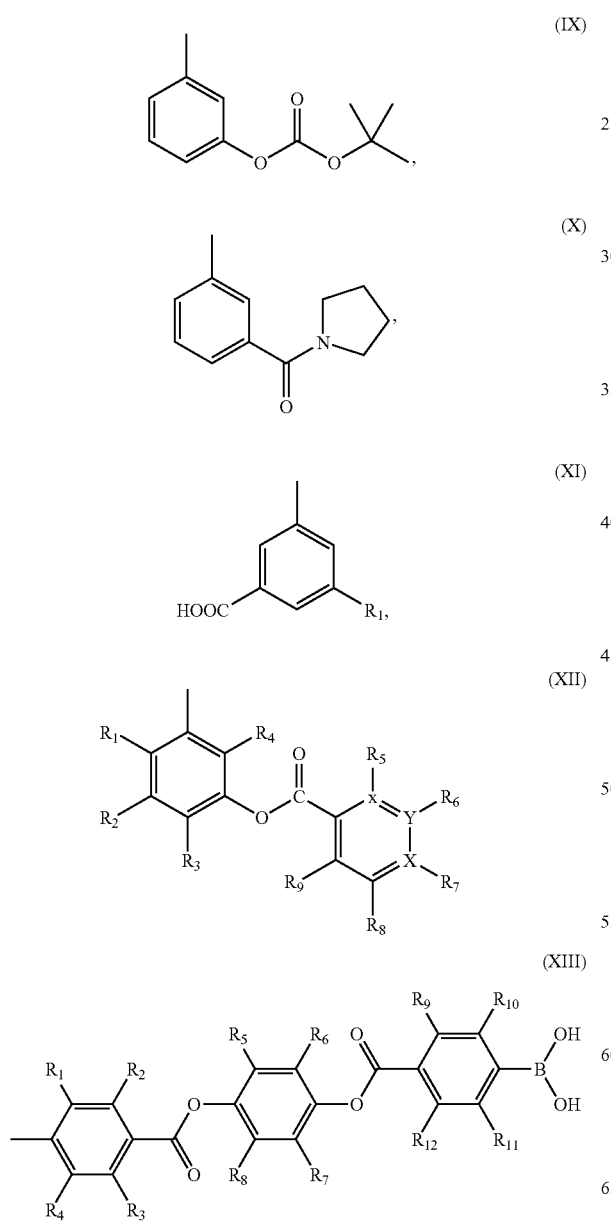

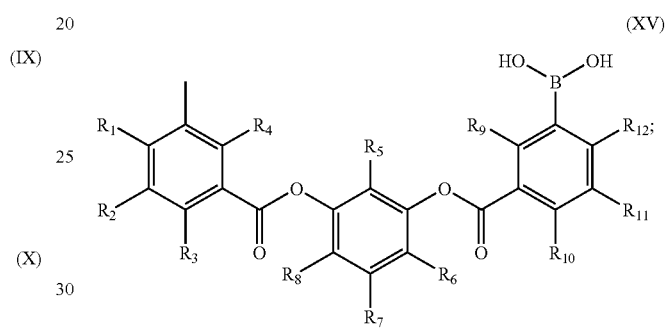

wherein $R_1$ through $R_{12}$ are each independently (i) when connected to a carbon atom: hydrogen, $C_{1-6}$ alkyl, $C_{3-6}$ cycloalkyl, $C_{1-3}$ alkoxy, n-butoxy, i-butoxy, sec-butoxy, $R_{13}R_{14}N$— (wherein $R_{13}$ and $R_{14}$ are each independently hydrogen or $C_{1-3}$ alkyl), trifluoromethyl, trifluoromethoxy, difluoromethoxy, fluoro, chloro, bromo, cyano, acetyl, amino, borono, nitro, carboxyl, $C_{1-6}$ alkoxycarbonyl, phenyl, phenoxy, phenoxycarbonyl, benzyloxy, hydroxyl, trimethylsilyloxy, diphenyl-t-butylsilyloxy, hydroxymethyl, —CHO, —CH=NOH, —C=NOHCH$_3$, —SO$_3$H, —SO$_2$CH$_3$, —SO$_2$NHR$_{15}$, wherein $R_{15}$ is hydrogen or $C_{1-3}$ alkyl, or —O(CH$_2$)$_n$OR$_{16}$—, wherein $R_{16}$ is hydrogen or $C_{1-3}$ alkyl, and n is 1, 2 or 3; or when any two $R_i$s are located at the ortho position to each other, they together form -$Z_1$=$Z_2$-$Z_3$=$Z_4$- (wherein $Z_1$ through $Z_4$ each independently represents CH or N), —S—CO—O—, —CH=CH—NH—, —CH=CH—S—, —CH=CH—O—, —N=CH—NH—, —CH$_2$—N=N—, —N=N—O—, —N=CH—S— or —O—CH$_2$CH$_2$—O—;

or (ii) when connected to a nitrogen atom: absent;

X, Y and Z are each independently carbon or nitrogen; and

Q is oxygen or lone-pair electrons.

In a first embodiment, the compounds of the present invention are represented by formula A(I):

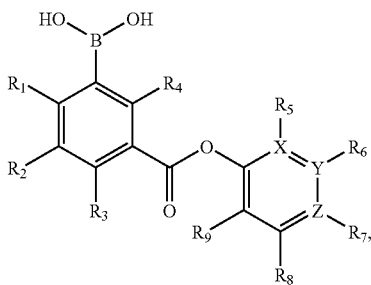

A(I)

wherein
$R_1$ through $R_9$ are each independently
  (i) when connected to a carbon atom: hydrogen, $C_{1-6}$ alkyl, $C_{3-6}$ cycloalkyl, $C_{1-3}$ alkoxy, n-butoxy, i-butoxy, sec-butoxy, $R_{13}R_{14}N-$, wherein $R_{13}$ and $R_{14}$ are each independently hydrogen or $C_{1-3}$ alkyl, trifluoromethyl, trifluoromethoxy, difluoromethoxy, fluoro, chloro, bromo, cyano, acetyl, amino, borono, nitro, carboxyl, $C_{1-6}$ alkoxycarbonyl, phenyl, phenoxy, phenoxycarbonyl, benzyloxy, hydroxyl, trimethylsilyloxy, diphenyl-t-butylsilyloxy, hydroxymethyl, —CHO, —CH=NOH, —C=NOHCH$_3$, —SO$_3$H, —SO$_2$CH$_3$, —SO$_2$NHR$_{15}$, wherein $R_{15}$ is hydrogen or $C_{1-3}$ alkyl, or —O(CH$_2$)$_n$OR$_{16}$—, wherein $R_{16}$ is hydrogen or $C_{1-3}$ alkyl, and n is 1, 2 or 3; or when any two $R_i$s are located at the ortho position to each other, they together form -$Z_1$=$Z_2$-$Z_3$=$Z_4$-, wherein $Z_1$ through $Z_4$ each independently represents CH or N, —S—CO—O—, —CH=CH—NH—, —CH=CH—S—, —CH=CHO—, —N=CH—NH—, —CH$_2$—N=N—, —N=N—O—, —N=CH—S— or —O—CH$_2$CH$_2$—O—; or
  (ii) when connected to a nitrogen atom: absent; and
X, Y and Z are each independently carbon or nitrogen.

In a preferred embodiment of the first embodiment,
$R_1$, $R_3$ and $R_4$ are each hydrogen;
$R_2$ is hydrogen, fluoro, chloro, bromo, cyano, acetyl, amino, nitro, carboxyl, $C_{1-4}$ alkoxycarbonyl, phenoxycarbonyl, hydroxyl, —CHO, —CH=NOH, —C=NOHCH$_3$, —SO$_3$H, —SO$_2$CH$_3$ and —SO$_2$NH$_2$;
$R_5$ is:
  (i) when X is nitrogen:
  absent, and
  (ii) when X is carbon:
  hydrogen, $C_{1-4}$ alkyl, $C_{3-6}$ cycloalkyl, $C_{1-3}$ alkoxy, trifluoromethyl, fluoro, chloro, bromo, cyano, acetyl, amino, borono, nitro, carboxyl, $C_{1-4}$ alkoxycarbonyl, phenyl, phenoxy, phenoxycarbonyl, 2,4-dichlorophenoxy, benzyloxy, hydroxyl, hydroxymethyl, —CHO, —CH=NOH, —C=NOHCH$_3$, —SO$_3$H, —SO$_2$CH$_3$, —SO$_2$NH$_2$, or when $R_5$ are located at the ortho position to another $R_i$, they together form -$Z_1$=$Z_2$-$Z_3$=$Z_4$- (wherein $Z_1$ through $Z_4$ each independently represents CH or N), —S—CO—O—, —CH=CH—NH—, —CH=CH—S—, —CH=CH—O—, —N=CH—NH—, —CH$_2$—N=N—, —N=N—O—, —N=CH—S— or —O—CH$_2$CH$_2$—O—;
$R_6$ is:
  (i) when Y is nitrogen:
  absent, and
  (ii) when Y is carbon:
  hydrogen, $C_{1-4}$ alkyl, $C_{3-6}$ cycloalkyl, $C_{1-3}$ alkoxy, trifluoromethyl, fluoro, chloro, bromo, cyano, acetyl, amino, borono, nitro, carboxyl, $C_{1-4}$ alkoxycarbonyl, phenyl, phenoxy, phenoxycarbonyl, benzyloxy, hydroxyl, hydroxymethyl, —CHO, —CH=NOH, —C=NOHCH$_3$, —SO$_3$H, —SO$_2$CH$_3$, —SO$_2$NH$_2$, or when $R_6$ are located at the ortho position to another $R_i$, they together form -$Z_1$=$Z_2$-$Z_3$=$Z_4$- (wherein $Z_1$ through $Z_4$ each independently represents CH or N), —S—CO—O—, —CH=CH—NH—, —CH=CH—S—, —CH=CH—O—, —N=CH—NH—, —CH$_2$—N=N—, —N=N—O—, —N=CH—S— or —O—CH$_2$CH$_2$—O—;
$R_7$ is:
  (i) when Z is nitrogen:
  absent, and
  (ii) when Z is carbon:
  hydrogen, $C_{1-4}$ alkyl, $C_{3-6}$ cycloalkyl, $C_{1-3}$ alkoxy, trifluoromethyl, fluoro, chloro, bromo, cyano, acetyl, amino, borono, nitro, carboxyl, $C_{1-4}$ alkoxycarbonyl, phenyl, phenoxy, phenoxycarbonyl, benzyloxy, hydroxyl, hydroxymethyl, —CHO, —CH=NOH, —C=NOHCH$_3$, —SO$_3$H, —SO$_2$CH$_3$, —SO$_2$NH$_2$, or when $R_7$ are located at the ortho position to another $R_i$, they together form -$Z_1$=$Z_2$-$Z_3$=$Z_4$- (wherein $Z_1$ through $Z_4$ each independently represents CH or N), —S—CO—O—, —CH=CH—NH—, —CH=CH—S—, —CH=CH—O—, —N=CH—NH—, —CH$_2$—N=N—, —N=N—O—, —N=CH—S— or —O—CH$_2$CH$_2$—O—;
$R_8$ through $R_9$ are each independently hydrogen, $C_{1-4}$ alkyl, $C_{3-6}$ cycloalkyl, $C_{1-3}$ alkoxy, trifluoromethyl, fluoro, chloro, bromo, cyano, acetyl, amino, borono, nitro, carboxyl, $C_{1-4}$ alkoxycarbonyl, phenyl, phenoxy, phenoxycarbonyl, benzyloxy, hydroxyl, hydroxymethyl, —CHO, —CH=NOH, —C=NOHCH$_3$, —SO$_3$H, —SO$_2$CH$_3$, —SO$_2$NH$_2$, or when any two $R_i$s are located at the ortho position to each other, they together form -$Z_1$=$Z_2$-$Z_3$=$Z_4$- (wherein $Z_1$ through $Z_4$ each independently represents CH or N), —S—CO—O—, —CH=CH—NH—, —CH=CH—S—, —CH=CH—O—, —N=CH—NH—, —CH$_2$—N=N—, —N=N—O—, —N=CH—S— or —O—CH$_2$CH$_2$—O—; and
X, Y and Z are each independently carbon or nitrogen.

In a second embodiment, the compounds of the present invention are represented by formula A(II):

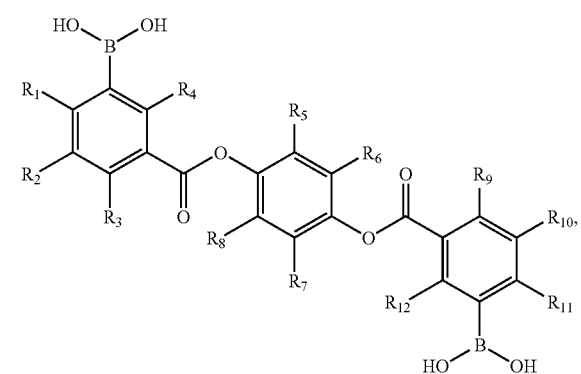

A(II)

wherein $R_1$ through $R_{12}$ are each independently hydrogen, $C_{1-6}$ alkyl, $C_{3-6}$ cycloalkyl, $C_{1-3}$ alkoxy, n-butoxy, i-butoxy, sec-butoxy, $R_{13}R_{14}N$— (wherein $R_{13}$ and $R_{14}$ are each independently hydrogen or $C_{1-3}$ alkyl), trifluoromethyl, trifluoromethoxy, difluoromethoxy, fluoro, chloro, bromo, cyano, acetyl, amino, borono, nitro, carboxyl, $C_{1-6}$ alkoxycarbonyl, phenyl, phenoxy, phenoxycarbonyl, benzyloxy, hydroxyl, trimethylsilyloxy, diphenyl-t-butylsilyloxy, hydroxymethyl, —$SO_3H$, —$SO_2CH_3$, —$SO_2NHR_{15}$ (wherein $R_{15}$ is hydrogen or $C_{1-3}$ alkyl), or —$O(CH_2)_n$$OR_{16}$— (wherein $R_{16}$ is hydrogen or $C_{1-3}$ alkyl, and n is 1, 2 or 3); or when any two $R_i$s are located at the ortho position to each other, they together form -$Z_1$=$Z_2$-$Z_3$=$Z_4$- (wherein $Z_1$ through $Z_4$ each independently represents CH or N), —S—CO—O—, —CH=CH—NH—, —CH=CH—S—, —CH=CH—O—, —N=CH—NH—, —CH$_2$—N=N—, —N=N—O—, —N=CH—S— or —O—CH$_2$CH$_2$—O—.

In a preferred embodiment of the second embodiment,
$R_1$, $R_3$, $R_4$, $R_9$, $R_{11}$ and $R_{12}$ are each hydrogen;
$R_2$ and $R_{10}$ are each independently hydrogen, fluoro, chloro, bromo, cyano, acetyl, nitro, amino, borono, carboxyl, $C_{1-4}$ alkoxycarbonyl, phenoxycarbonyl, hydroxyl, —$SO_3H$, —$SO_2CH_3$ and —$SO_2NH_2$;
$R_5$ through $R_8$ are each independently hydrogen, $C_{1-4}$ alkyl, $C_{3-6}$ cycloalkyl, $C_{1-3}$ alkoxy, trifluoromethyl, fluoro, chloro, bromo, cyano, acetyl, amino, borono, nitro, carboxyl, $C_{1-4}$ alkoxycarbonyl, phenyl, phenoxy, phenoxycarbonyl, benzyloxy, hydroxyl, hydroxymethyl, —$SO_3H$, —$SO_2CH_3$, —$SO_2NH_2$, or when any two $R_i$s are located at the ortho position to each other, they together form -$Z_1$=$Z_2$-$Z_3$=$Z_4$- (wherein $Z_1$ through $Z_4$ each independently represents CH or N), —S—CO—O—, —CH=CH—NH—, —CH=CH—S—, —CH=CH—O—, —N=CH—NH—, —CH$_2$—N=N—, —N=N—O—, —N=CH—S— or —O—CH$_2$CH$_2$—O—.

In a third embodiment, the compounds of the present invention are represented by formula A(III):

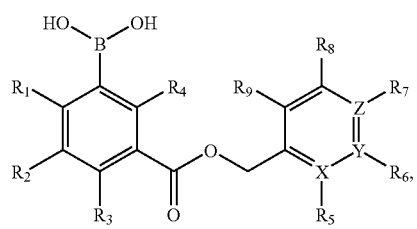

A(III)

wherein $R_1$ through $R_9$ are each independently
(i) when connected to a carbon atom:
hydrogen, $C_{1-6}$ alkyl, $C_{3-6}$ cycloalkyl, $C_{1-3}$ alkoxy, n-butoxy, i-butoxy, sec-butoxy, $R_{13}R_{14}N$— (wherein $R_{13}$ and $R_{14}$ are each independently hydrogen or $C_{1-3}$ alkyl), trifluoromethyl, trifluoromethoxy, difluoromethoxy, fluoro, chloro, bromo, cyano, acetyl, amino, borono, nitro, carboxyl, $C_{1-6}$ alkoxycarbonyl, phenyl, phenoxy, phenoxycarbonyl, benzyloxy, hydroxyl, trimethylsilyloxy, diphenyl-t-butylsilyloxy, hydroxymethyl, —CHO, —CH=NOH, —C=NOHCH$_3$, —$SO_3H$, —$SO_2CH_3$, —$SO_2NHR_{15}$ (wherein $R_{15}$ is hydrogen or $C_{1-3}$ alkyl), or —$O(CH_2)_n$$OR_{16}$— (wherein $R_{16}$ is hydrogen or $C_{1-3}$ alkyl, and n is 1, 2 or 3); or when any two $R_i$s are located at the ortho position to each other, they together form -$Z_1$=$Z_2$-$Z_3$=$Z_4$- (wherein $Z_1$ through $Z_4$ each independently represents CH or N), —S—CO—O—, —CH=CH—NH—, —CH=CH—S—, —CH=CH—O—, —N=CH—NH—, —CH$_2$—N=N—, —N=N—O—, —N=CH—S— or —O—CH$_2$CH$_2$—O—; or
(ii) when connected to a nitrogen atom;
absent;
and
X, Y and Z are each independently carbon or nitrogen.

In a preferred embodiment of the third embodiment,
$R_1$, $R_3$ and $R_4$ are each hydrogen;
$R_2$ is hydrogen, fluoro, chloro, bromo, cyano, acetyl, amino, nitro, carboxyl, $C_{1-4}$ alkoxycarbonyl, phenoxycarbonyl, hydroxyl, —CHO, —CH=NOH, —C=NOHCH$_3$, —$SO_3H$, —$SO_2CH_3$ and —$SO_2NH_2$;
$R_5$ is:
(i) when X is nitrogen:
absent, and
(ii) when X is carbon:
hydrogen, $C_{1-4}$ alkyl, $C_{3-6}$ cycloalkyl, $C_{1-3}$ alkoxy, trifluoromethyl, fluoro, chloro, bromo, cyano, acetyl, amino, borono, nitro, carboxyl, $C_{1-4}$ alkoxycarbonyl, phenyl, phenoxy, phenoxycarbonyl, benzyloxy, hydroxyl, hydroxymethyl, —CHO, —CH=NOH, —C=NOHCH$_3$, —$SO_3H$, —$SO_2CH_3$, —$SO_2NH_2$, or when $R_5$ are located at the ortho position to another $R_i$, they together form -$Z_1$=$Z_2$-$Z_3$=$Z_4$- (wherein $Z_1$ through $Z_4$ each independently represents CH or N), —S—CO—O—, —CH=CH—NH—, —CH=CH—S—, —CH=CH—O—, —N=CH—NH—, —CH$_2$—N=N—, —N=N—O—, —N=CH—S— or —O—CH$_2$CH$_2$—O—;
$R_6$ is:
(i) when Y is nitrogen:
absent, and
(ii) when Y is carbon:
hydrogen, $C_{1-4}$ alkyl, $C_{3-6}$ cycloalkyl, $C_{1-3}$ alkoxy, trifluoromethyl, fluoro, chloro, bromo, cyano, acetyl, amino, borono, nitro, carboxyl, $C_{1-4}$ alkoxycarbonyl, phenyl, phenoxy, phenoxycarbonyl, benzyloxy, hydroxyl, hydroxymethyl, —CHO, —CH=NOH, —C=NOHCH$_3$, —$SO_3H$, —$SO_2CH_3$, —$SO_2NH_2$, or when $R_6$ are located at the ortho position to another $R_i$, they together form -$Z_1$-$Z_2$-$Z_3$=$Z_4$- (wherein $Z_1$ through $Z_4$ each independently represents CH or N), —S—CO—O—, —CH=CH—NH—, —CH=CH—S—, —CH=CH—O—, —N=CH—NH—, —CH$_2$—N=N—, —N=N—O—, —N=CH—S— or —O—CH$_2$CH$_2$—O—;
$R_7$ is:
(i) when Z is nitrogen:
absent, and
(ii) when Z is carbon:
hydrogen, $C_{1-4}$ alkyl, $C_{3-6}$ cycloalkyl, $C_{1-3}$ alkoxy, trifluoromethyl, fluoro, chloro, bromo, cyano, acetyl, amino, borono, nitro, carboxyl, $C_{1-4}$ alkoxycarbonyl, phenyl, phenoxy, phenoxycarbonyl, benzyloxy, hydroxyl, hydroxymethyl, —CHO, —CH=NOH, —C=NOHCH$_3$, —$SO_3H$, —$SO_2CH_3$, —$SO_2NH_2$, or when $R_7$ are located at the ortho position to another $R_i$, they together form -$Z_1$=$Z_2$-$Z_3$=$Z_4$- (wherein $Z_1$ through $Z_4$ each independently represents CH or N), —S—CO—O—, —CH=CH—NH—, —CH=CH—O—, —N=CH—NH—, —CH$_2$—N=N—, —N=N—O—, —N=CH—S— or —O—CH$_2$CH$_2$—O—;
$R_8$ through $R_9$ are each independently hydrogen, $C_{1-4}$ alkyl, $C_{3-6}$ cycloalkyl, $C_{1-3}$ alkoxy, trifluoromethyl, fluoro, chloro, bromo, cyano, acetyl, amino, borono, nitro, carboxyl, $C_{1-4}$ alkoxycarbonyl, phenyl, phenoxy, phenoxycarbonyl, benzyloxy, hydroxyl, hydroxymethyl, —CHO, —CH=NOH, —C=NOHCH$_3$, —SO$_3$H, —SO$_2$CH$_3$, —SO$_2$NH$_2$, or when any two R$_i$s are located at the ortho position to each other, they together form -Z$_1$=Z$_2$-Z$_3$=Z$_4$- (wherein Z$_1$ through Z$_4$ each independently represents CH or N), —S—CO—O—, —CH=CH—NH—, —CH=CH—S—, —CH=CH—O—, —N=CH—NH—, —CH$_2$—N=N—, —N=N—O—, —N=CH—S— or —O—CH$_2$CH$_2$—O—; and X, Y and Z are each independently carbon or nitrogen.

In one particular embodiment of the third embodiment, the present invention relates to compounds represented by formula A(III)

wherein R$_1$ through R$_9$ are each independently (i) when connected to a carbon atom:

hydrogen, C$_{1-6}$ alkyl, C$_{3-6}$ cycloalkyl, C$_{1-3}$ alkoxy, n-butoxy, i-butoxy, sec-butoxy, R$_{13}$R$_{14}$N— (wherein R$_{13}$ and R$_{14}$ are each independently hydrogen or C$_{1-3}$ alkyl), trifluoromethyl, trifluoromethoxy, difluoromethoxy, fluoro, chloro, bromo, cyano, acetyl, amino, borono, nitro, carboxyl, C$_{1-6}$ alkoxycarbonyl, phenyl, phenoxy, phenoxycarbonyl, benzyloxy, hydroxyl, trimethylsilyloxy, diphenyl-t-butylsilyloxy, hydroxymethyl, —CHO, —CH=NOH, —C=NOHCH$_3$, —SO$_3$H, —SO$_2$CH$_3$, —SO$_2$NHR$_{15}$ (wherein R$_{15}$ is hydrogen or C$_{1-3}$ alkyl), or —O(CH$_2$)$_n$OR$_{16}$— (wherein R$_{16}$ is hydrogen or C$_{1-3}$ alkyl, and n is 1, 2 or 3); or when any two R$_i$s are located at the ortho position to each other, they together form -Z$_1$=Z$_2$-Z$_3$=Z$_4$- (wherein Z$_1$ through Z$_4$ each independently represents CH or N), —S—CO—O—, —CH=CH—NH—, —CH=CH—S—, —CH=CH—O—, —N=CH—NH—, —CH$_2$—N=N—, —N=N—O—, —N=CH—S— or —O—CH$_2$CH$_2$—O—; or (ii) when connected to a nitrogen atom:

absent; and

X, Y and Z are each independently carbon or nitrogen;

with the proviso that when R$_1$=R$_3$=R$_4$=R$_5$=R$_6$=R$_7$=R$_8$=R$_9$=hydrogen, and X=Y=Z=carbon; R$_2$ is not NH$_2$, NO$_2$, or H.

In another embodiment of the third embodiment, the invention relates to compounds described by formula A(III) wherein R$_1$, R$_3$ and R$_4$ are each hydrogen;

R$_2$ is hydrogen, fluoro, chloro, bromo, cyano, acetyl, amino, nitro, carboxyl, C$_{1-4}$ alkoxycarbonyl, phenoxycarbonyl, hydroxyl, —CHO, —CH=NOH, —C=NOHCH$_3$, —SO$_3$H, —SO$_2$CH$_3$ and —SO$_2$NH$_2$;

R$_5$ is:

(i) when X is nitrogen:

absent, and (ii) when X is carbon:

hydrogen, C$_{1-4}$ alkyl, C$_{3-6}$ cycloalkyl, C$_{1-3}$ alkoxy, trifluoromethyl, fluoro, chloro, bromo, cyano, acetyl, amino, borono, nitro, carboxyl, C$_{1-4}$ alkoxycarbonyl, phenyl, phenoxy, phenoxycarbonyl, benzyloxy, hydroxyl, hydroxymethyl, —CHO, —CH=NOH, —C=NOHCH$_3$, —SO$_3$H, —SO$_2$CH$_3$, —SO$_2$NH$_2$, or when R$_5$ are located at the ortho position to another R$_i$, they together form -Z$_1$=Z$_2$-Z$_3$=Z$_4$- (wherein Z$_1$ through Z$_4$ each independently represents CH or N), —S—CO—O—, —CH=CH—NH—, —CH=CH—S—, —CH=CH—O—, —N=CH—NH—, —CH$_2$—N=N—, —N=N—O—, —N=CH—S— or —O—CH$_2$CH$_2$—O—;

R$_6$ is:

(i) when Y is nitrogen:

absent, and (ii) when Y is carbon:

hydrogen, C$_{1-4}$ alkyl, C$_{3-6}$ cycloalkyl, C$_{1-3}$ alkoxy, trifluoromethyl, fluoro, chloro, bromo, cyano, acetyl, amino, borono, nitro, carboxyl, C$_{1-4}$ alkoxycarbonyl, phenyl, phenoxy, phenoxycarbonyl, benzyloxy, hydroxyl, hydroxymethyl, —CHO, —CH=NOH, —C=NOHCH$_3$, —SO$_3$H, —SO$_2$CH$_3$, —SO$_2$NH$_2$, or when R$_6$ are located at the ortho position to another R$_i$, they together form -Z$_1$=Z$_2$-Z$_3$=Z$_4$- (wherein Z$_1$ through Z$_4$ each independently represents CH or N), —S—CO—O—, —CH=CH—NH—, —CH=CH—S—, —CH=CH—O—, —N=CH—NH—, —CH$_2$—N=N—, —N=N—O—, —N=CH—S— or —O—CH$_2$CH$_2$—O—;

R$_7$ is:

(i) when Z is nitrogen:

absent, and (ii) when Z is carbon:

hydrogen, C$_{1-4}$ alkyl, C$_{3-6}$ cycloalkyl, C$_{1-3}$ alkoxy, trifluoromethyl, fluoro, chloro, bromo, cyano, acetyl, amino, borono, nitro, carboxyl, C$_{1-4}$ alkoxycarbonyl, phenyl, phenoxy, phenoxycarbonyl, benzyloxy, hydroxyl, hydroxymethyl, —CHO, —CH=NOH, —C=NOHCH$_3$, —SO$_3$H, —SO$_2$CH$_3$, —SO$_2$NH$_2$, or when R$_7$ are located at the ortho position to another R$_i$, they together form -Z$_1$=Z$_2$-Z$_3$=Z$_4$- (wherein Z$_1$ through Z$_4$ each independently represents CH or N), —S—CO—O—, —CH=CH—NH—, —CH=CH—S—, —CH=CH—O—, —N=CH—NH—, —CH$_2$—N=N—, —N=N—O—, —N=CH—S— or —O—CH$_2$CH$_2$—O—;

R$_8$ through R$_9$ are each independently hydrogen, C$_{1-4}$ alkyl, C$_{3-6}$ cycloalkyl, C$_{1-3}$ alkoxy, trifluoromethyl, fluoro, chloro, bromo, cyano, acetyl, amino, borono, nitro, carboxyl, C$_{1-4}$ alkoxycarbonyl, phenyl, phenoxy, phenoxycarbonyl, benzyloxy, hydroxyl, hydroxymethyl, —CHO, —CH=NOH, —C=NOHCH$_3$, —SO$_3$H, —SO$_2$CH$_3$, —SO$_2$NH$_2$, or when any two R$_i$s are located at the ortho position to each other, they together form -Z$_1$=Z$_2$-Z$_3$=Z$_4$- (wherein Z$_1$ through Z$_4$ each independently represents CH or N), —S—CO—O—, —CH=CH—NH—, —CH=CH—S—, —CH=CH—O—, —N=CH—NH—, —CH$_2$—N=N—, —N=N—O—, —N=CH—S— or —O—CH$_2$CH$_2$—O—; and X, Y and Z are each independently carbon or nitrogen;

with the proviso that when R$_1$=R$_3$=R$_4$=R$_5$=R$_6$=R$_7$=R$_9$=R$_9$=hydrogen, and X=Y=Z=carbon; R$_2$ is not NH$_2$, NO$_2$, or H.

In a fourth embodiment, the compounds of the present invention are represented by formula A(IV):

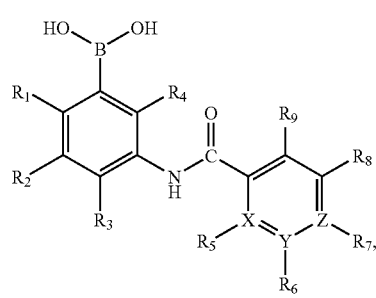

wherein R$_1$ through R$_9$ are each independently (i) when connected to a carbon atom:

hydrogen, C$_{1-6}$ alkyl, C$_{3-6}$ cycloalkyl, C$_{1-3}$ alkoxy, n-butoxy, i-butoxy, sec-butoxy, R$_{13}$R$_{14}$N— (wherein R$_{13}$ and $R_{14}$ are each independently hydrogen or $C_{1-3}$ alkyl), trifluoromethyl, trifluoromethoxy, difluoromethoxy, fluoro, chloro, bromo, cyano, acetyl, amino, borono, nitro, carboxyl, $C_{1-6}$ alkoxycarbonyl, phenyl, phenoxy, phenoxycarbonyl, benzyloxy, hydroxyl, trimethylsilyloxy, diphenyl-t-butylsilyloxy, hydroxymethyl, —CHO, —CH=NOH, —C=NOHCH$_3$, —SO$_3$H, —SO$_2$CH$_3$, —SO$_2$NHR$_{15}$ (wherein R$_{15}$ is hydrogen or $C_{1-3}$ alkyl), or —O(CH$_2$)$_n$OR$_{16}$— (wherein R$_{16}$ is hydrogen or $C_{1-3}$ alkyl, and n is 1, 2 or 3); or when any two R$_i$s are located at the ortho position to each other, they together form -Z$_1$-Z$_2$-Z$_3$=Z$_4$- (wherein Z$_1$ through Z$_4$ each independently represents CH or N), —S—CO—O—, —CH=CH—NH—, —CH=CH—S—, —CH=CH—O—, —N=CH—NH—, —CH$_2$—N=N—, —N=N—O—, —N=CH—S— or —O—CH$_2$CH$_2$—O—; or (ii) when connected to a nitrogen atom;
absent;
and X, Y and Z are each independently carbon or nitrogen.

In a preferred embodiment of the fourth embodiment,
$R_1$, $R_3$ and $R_4$ are each hydrogen;

$R_2$ is hydrogen, fluoro, chloro, bromo, cyano, acetyl, amino, nitro, carboxyl, $C_{1-4}$ alkoxycarbonyl, phenoxycarbonyl, hydroxyl, —CHO, —CH=NOH, —C=NOHCH$_3$, —SO$_3$H, —SO$_2$CH$_3$ and —SO$_2$NH$_2$;

$R_5$ is:
(i) when X is nitrogen:
absent, and
(ii) when X is carbon:
hydrogen, $C_{1-4}$ alkyl, $C_{3-6}$ cycloalkyl, $C_{1-3}$ alkoxy, trifluoromethyl, fluoro, chloro, bromo, cyano, acetyl, amino, borono, nitro, carboxyl, $C_{1-4}$ alkoxycarbonyl, phenyl, phenoxy, phenoxycarbonyl, benzyloxy, hydroxyl, hydroxymethyl, —CHO, —CH=NOH, —C=NOHCH$_3$, —SO$_3$H, —SO$_2$CH$_3$, —SO$_2$NH$_2$, or when R$_5$ are located at the ortho position to another R$_i$, they together form -Z$_1$=Z$_2$-Z$_3$=Z$_4$- (wherein Z$_1$ through Z$_4$ each independently represents CH or N), —S—CO—O—, —CH=CH—NH—, —CH=CH—S—, —CH=CH—O—, —N=CH—NH—, —CH$_2$—N=N—, —N=N—O—, —N=CH—S— or —O—CH$_2$CH$_2$—O—;

$R_6$ is:
(i) when Y is nitrogen:
absent, and
(ii) when Y is carbon:
hydrogen, $C_{1-4}$ alkyl, $C_{3-6}$ cycloalkyl, $C_{1-3}$ alkoxy, trifluoromethyl, fluoro, chloro, bromo, cyano, acetyl, amino, borono, nitro, carboxyl, $C_{1-4}$ alkoxycarbonyl, phenyl, phenoxy, phenoxycarbonyl, benzyloxy, hydroxyl, hydroxymethyl, —CHO, —CH=NOH, —C=NOHCH$_3$, —SO$_3$H, —SO$_2$CH$_3$, —SO$_2$NH$_2$, or when R$_6$ are located at the ortho position to another R$_i$, they together form -Z$_1$=Z$_2$-Z$_3$=Z$_4$- (wherein Z$_1$ through Z$_4$ each independently represents CH or N), —S—CO—O—, —CH=CH—NH—, —CH=CH—S—, —CH=CH—O—, —N=CH—NH—, —CH$_2$—N=N—, —N=N—O—, —N=CH—S— or —O—CH$_2$CH$_2$—O—;

$R_7$ is:
(i) when Z is nitrogen:
absent, and
(ii) when Z is carbon:
hydrogen, $C_{1-4}$ alkyl, $C_{3-6}$ cycloalkyl, $C_{1-3}$ alkoxy, trifluoromethyl, fluoro, chloro, bromo, cyano, acetyl, amino, borono, nitro, carboxyl, $C_{1-4}$ alkoxycarbonyl, phenyl, phenoxy, phenoxycarbonyl, benzyloxy, hydroxyl, hydroxymethyl, —CHO, —CH=NOH, —C=NOHCH$_3$, —SO$_3$H, —SO$_2$CH$_3$, —SO$_2$NH$_2$, or when R$_7$ are located at the ortho position to another R$_i$, they together form -Z$_1$=Z$_2$-Z$_3$=Z$_4$- (wherein Z$_1$ through Z$_4$ each independently represents CH or N), —S—CO—O—, —CH=CH—NH—, —CH=CH—S—, —CH=CH—O—, —N=CH—NH—, —CH$_2$—N=N—, —N=N—O—, —N=CH—S— or —O—CH$_2$CH$_2$—O—;

$R_8$ through $R_9$ are each independently hydrogen, $C_{1-4}$ alkyl, $C_{3-6}$ cycloalkyl, $C_{1-3}$ alkoxy, trifluoromethyl, fluoro, chloro, bromo, cyano, acetyl, amino, borono, nitro, carboxyl, $C_{1-4}$ alkoxycarbonyl, phenyl, phenoxy, phenoxycarbonyl, benzyloxy, hydroxyl, hydroxymethyl, —CHO, —CH=NOH, —C=NOHCH$_3$, —SO$_3$H, —SO$_2$CH$_3$, —SO$_2$NH$_2$, or when any two R$_i$s are located at the ortho position to each other, they together form -Z$_1$=Z$_2$-Z$_3$=Z$_4$- (wherein Z$_1$ through Z$_4$ each independently represents CH or N), —S—CO—O—, —CH=CH—NH—, —CH=CH—S—, —CH=CH—O—, —N=CH—NH—, —CH$_2$—N=N—, —N=N—O—, —N=CH—S— or —O—CH$_2$CH$_2$—O—; and X, Y and Z are each independently carbon or nitrogen.

In one particular embodiment of the fourth embodiment, the compounds of the present invention are represented by formula A(IV)

wherein $R_1$ through $R_9$ are each independently
(i) when connected to a carbon atom:
hydrogen, $C_{1-6}$ alkyl, $C_{3-6}$ cycloalkyl, $C_{1-3}$ alkoxy, n-butoxy, i-butoxy, sec-butoxy, $R_{13}R_{14}N$— (wherein $R_{13}$ and $R_{14}$ are each independently hydrogen or $C_{1-3}$ alkyl), trifluoromethyl, trifluoromethoxy, difluoromethoxy, fluoro, chloro, bromo, cyano, acetyl, amino, borono, nitro, carboxyl, $C_{1-6}$ alkoxycarbonyl, phenyl, phenoxy, phenoxycarbonyl, benzyloxy, hydroxyl, trimethylsilyloxy, diphenyl-t-butylsilyloxy, hydroxymethyl, —CHO, —CH=NOH, —C=NOHCH$_3$, —SO$_3$H, —SO$_2$CH$_3$, —SO$_2$NHR$_{15}$ (wherein R$_{15}$ is hydrogen or $C_{1-3}$ alkyl), or —O(CH$_2$)$_n$OR$_{16}$— (wherein R$_{16}$ is hydrogen or $C_{1-3}$ alkyl, and n is 1, 2 or 3); or when any two R$_i$s are located at the ortho position to each other, they together form -Z$_1$-Z$_2$-Z$_3$=Z$_4$- (wherein Z$_1$ through Z$_4$ each independently represents CH or N), —S—CO—O—, —CH=CH—NH—, —CH=CH—S—, —CH=CH—O—, —N=CH—NH—, —CH$_2$—N=N—, —N=N—O—, —N=CH—S— or —O—CH$_2$CH$_2$—O—; or (ii) when connected to a nitrogen atom;
absent; and X, Y and Z are each independently carbon or nitrogen; with the proviso that when $R_1=R_2=R_3=R_4=R_5=R_6=R_8=R_9$=hydrogen, and X=Y=Z=carbon; R$_7$ is not Cl, CN, OCH$_3$, NO$_2$, CF$_3$, H, or COOCH$_3$;

when $R_1=R_2=R_3=R_4=R_5=R_7=R_8=R_9$=hydrogen, and X=Y=Z=carbon; R$_6$ is not CN, NO$_2$, or CF$_3$;

when $R_1=R_2=R_3=R_4=R_5=R_8=R_9$=hydrogen, and X=Y=Z=carbon; R$_6$ and R$_7$ together is not —CH=CH—CH=CH—;

when $R_1=R_2=R_3=R_4=R_6=R_7=R_8=R_9$=hydrogen, and X=Y=Z=carbon; R$_5$ is not OCOCH$_3$;

when $R_1=R_3=R_4=R_5=R_6=R_7=R_8=R_9$=hydrogen, and X=Y=Z=carbon; R$_2$ is not COOH; and when $R_1=R_2=R_3=R_4=R_5=R_8=R_9$=hydrogen, Rr=Cl, and X=Y=Z=carbon; R$_7$ is not Cl.

In a preferred embodiment of the fourth embodiment, the compounds of the present invention are represented by formula A(IV) wherein $R_1$, $R_3$ and $R_4$ are each hydrogen;

$R_2$ is hydrogen, fluoro, chloro, bromo, cyano, acetyl, amino, nitro, carboxyl, $C_{1-4}$ alkoxycarbonyl, phenoxycarbonyl, hydroxyl, —CHO, —CH=NOH, —C=NOHCH$_3$, —SO$_3$H, —SO$_2$CH$_3$ and —SO$_2$NH$_2$;

$R_5$ is:
  (i) when X is nitrogen:
    absent, and
  (ii) when X is carbon:
    hydrogen, $C_{1-4}$ alkyl, $C_{3-6}$ cycloalkyl, $C_{1-3}$ alkoxy, trifluoromethyl, fluoro, chloro, bromo, cyano, acetyl, amino, borono, nitro, carboxyl, $C_{1-4}$ alkoxycarbonyl, phenyl, phenoxy, phenoxycarbonyl, benzyloxy, hydroxyl, hydroxymethyl, —CHO, —CH=NOH, —C=NOHCH$_3$, —SO$_3$H, —SO$_2$CH$_3$, —SO$_2$NH$_2$, or when $R_5$ are located at the ortho position to another $R_i$, they together form -$Z_1$=$Z_2$-$Z_3$=$Z_4$- (wherein $Z_1$ through $Z_4$ each independently represents CH or N), —S—CO—O—, —CH=CH—NH—, —CH=CH—S—, —CH=CH—O—, —N=CH—NH—, —CH$_2$—N=N—, —N=N—O—, —N=CH—S— or —O—CH$_2$CH$_2$—O—;

$R_6$ is:
  (i) when Y is nitrogen:
    absent, and
  (ii) when Y is carbon:
    hydrogen, $C_{1-4}$ alkyl, $C_{3-6}$ cycloalkyl, $C_{1-3}$ alkoxy, trifluoromethyl, fluoro, chloro, bromo, cyano, acetyl, amino, borono, nitro, carboxyl, $C_{1-4}$ alkoxycarbonyl, phenyl, phenoxy, phenoxycarbonyl, benzyloxy, hydroxyl, hydroxymethyl, —CHO, —CH=NOH, —C=NOHCH$_3$, —SO$_3$H, —SO$_2$CH$_3$, —SO$_2$NH$_2$, or when $R_6$ are located at the ortho position to another $R_i$, they together form -$Z_1$=$Z_2$-$Z_3$=$Z_4$- (wherein $Z_1$ through $Z_4$ each independently represents CH or N), —S—CO—O—, —CH=CH—NH—, —CH=CH—S—, —CH=CH—O—, —N=CH—NH—, —CH$_2$—N=N—, —N=N—O—, —N=CH—S— or —O—CH$_2$CH$_2$—O—;

$R_7$ is:
  (i) when Z is nitrogen:
    absent, and
  (ii) when Z is carbon:
    hydrogen, $C_{1-4}$ alkyl, $C_{3-6}$ cycloalkyl, $C_{1-3}$ alkoxy, trifluoromethyl, fluoro, chloro, bromo, cyano, acetyl, amino, borono, nitro, carboxyl, $C_{1-4}$ alkoxycarbonyl, phenyl, phenoxy, phenoxycarbonyl, benzyloxy, hydroxyl, hydroxymethyl, —CHO, —CH=NOH, —C=NOHCH$_3$, —SO$_3$H, —SO$_2$CH$_3$, —SO$_2$NH$_2$, or when $R_7$ are located at the ortho position to another $R_i$, they together form -$Z_1$=$Z_2$-$Z_3$=$Z_4$- (wherein $Z_1$ through $Z_4$ each independently represents CH or N), —S—CO—O—, —CH=CH—NH—, —CH=CH—S—, —CH=CH—O—, —N=CH—NH—, —CH$_2$—N=N—, —N=N—O—, —N=CH—S— or —O—CH$_2$CH$_2$—O—;

$R_8$ through $R_9$ are each independently hydrogen, $C_{1-4}$ alkyl, $C_{3-6}$ cycloalkyl, $C_{1-3}$ alkoxy, trifluoromethyl, fluoro, chloro, bromo, cyano, acetyl, amino, borono, nitro, carboxyl, $C_{1-4}$ alkoxycarbonyl, phenyl, phenoxy, phenoxycarbonyl, benzyloxy, hydroxyl, hydroxymethyl, —CHO, —CH=NOH, —C=NOHCH$_3$, —SO$_3$H, —SO$_2$CH$_3$, —SO$_2$NH$_2$, or when any two $R_i$s are located at the ortho position to each other, they together form -$Z_1$=$Z_2$-$Z_3$=$Z_4$- (wherein $Z_1$ through $Z_4$ each independently represents CH or N), —S—CO—O—, —CH=CH—NH—, —CH=CH—S—, —CH=CH—O—, —N=CH—NH—, —CH$_2$—N=N—, —N=N—O—, —N=CH—S— or —O—CH$_2$CH$_2$—O—; and X, Y and Z are each independently carbon or nitrogen; with the proviso that
  when $R_1$=$R_2$=$R_3$=$R_4$=$R_5$=$R_6$=$R_8$=$R_9$=hydrogen, and X=Y=Z=carbon; $R_7$ is not Cl, CN, OCH$_3$, NO$_2$, CF$_3$, H, or COOCH$_3$;
  when $R_1$=$R_2$=$R_3$=$R_4$=$R_5$=$R_7$=$R_8$=$R_9$=hydrogen, and X=Y=Z=carbon; $R_6$ is not CN, NO$_2$, or CF$_3$;
  when $R_1$=$R_2$=$R_3$=$R_4$=$R_5$=$R_8$=$R_9$=hydrogen, and X=Y=Z=carbon; $R_6$ and $R_7$ together is not —CH=CH—CH=CH—;
  when $R_1$=$R_2$=$R_3$=$R_4$=$R_6$=$R_7$=$R_8$=$R_9$=hydrogen, and X=Y=Z=carbon; $R_5$ is not OCOCH$_3$;
  when $R_1$=$R_3$=$R_4$=$R_5$=$R_6$=$R_7$=$R_8$=$R_9$=hydrogen, and X=Y=Z=carbon; $R_2$ is not COOH; and
  when $R_1$=$R_2$=$R_3$=$R_4$=$R_5$=$R_8$=$R_9$=hydrogen, $R_6$=Cl, and X=Y=Z=carbon; $R_7$ is not Cl.

In a fifth embodiment, the compounds of the present invention are represented by formula A(V):

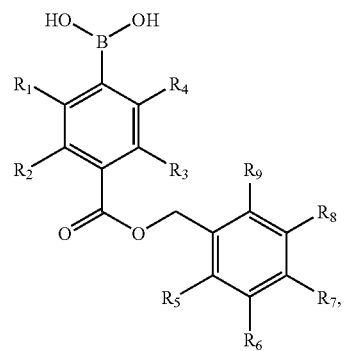

A(V)

wherein $R_1$ through $R_9$ are each independently hydrogen, $C_{1-6}$ alkyl, $C_{3-6}$ cycloalkyl, $C_{1-3}$ alkoxy, n-butoxy, i-butoxy, sec-butoxy, $R_{13}R_{14}N$— (wherein $R_{13}$ and $R_{14}$ each independently represents hydrogen or $C_{1-3}$ alkyl), trifluoromethyl, trifluoromethoxy, difluoromethoxy, fluoro, chloro, bromo, cyano, acetyl, nitro, amino, borono, carboxyl, $C_{1-6}$ alkoxycarbonyl, phenyl, phenoxy, phenoxycarbonyl, benzyloxy, hydroxyl, trimethylsilyloxy, diphenyl-t-butylsilyloxy, hydroxymethyl, —SO$_3$H, —SO$_2$CH$_3$, —SO$_2$NHR$_{15}$ (wherein $R_{15}$ is hydrogen or $C_{1-3}$ alkyl), or —O(CH$_2$)$_n$OR$_{16}$— (wherein $R_{16}$ is hydrogen or $C_{1-3}$ alkyl, and n is 1, 2 or 3); or when any two $R_i$s are located at the ortho position to each other, they together form -$Z_1$=$Z_2$-$Z_3$=$Z_4$- (wherein $Z_1$ through $Z_4$ each independently represents CH or N), —S—CO—O—, —CH=CH—NH—, —CH=CH—S—, —CH=CH—O—, —N=CH—NH—, —CH$_2$—N=N—, —N=N—O—, —N=CH—S— or —O—CH$_2$CH$_2$—O—.

In a preferred embodiment of the fifth embodiment,
$R_1$ and $R_4$ are each hydrogen;
$R_2$ and $R_3$ are each independently hydrogen, fluoro, chloro, bromo, cyano, acetyl, amino, borono, nitro, carboxyl, $C_{1-4}$ alkoxycarbonyl, phenoxycarbonyl, hydroxyl, —SO$_3$H, —SO$_2$CH$_3$ and —SO$_2$NH$_2$;
$R_5$ through $R_9$ are each independently hydrogen, $C_{1-4}$ alkyl, $C_{3-6}$ cycloalkyl, $C_{1-3}$ alkoxy, trifluoromethyl, fluoro, chloro, bromo, cyano, acetyl, amino, borono, nitro, carboxyl, $C_{1-4}$ alkoxycarbonyl, phenyl, phenoxy, phenoxycarbonyl, benzyloxy, hydroxyl, hydroxymethyl, —SO$_3$H, —SO$_2$CH$_3$, —SO$_2$NH$_2$, or when any two $R_i$s are located at the ortho position to each other, they together form -$Z_1$=$Z_2$-$Z_3$=$Z_4$- (wherein $Z_1$ through $Z_4$ each independently represents CH or N), —S—CO—O—, —CH=CH—NH—, —CH=CH—S—, —CH=CH—O—, —N=CH—NH—, —CH$_2$—N=N—, —N=N—O—, —N=CH—S— or —O—CH$_2$CH$_2$—O—.

In one particular embodiment of the fifth embodiment, the compounds of the present invention are represented by formula A(V):

wherein R$_1$ through R$_9$ are each independently hydrogen, C$_{1-6}$ alkyl, C$_{3-6}$ cycloalkyl, C$_{1-3}$ alkoxy, n-butoxy, i-butoxy, sec-butoxy, R$_{13}$R$_{14}$N— (wherein R$_{13}$ and R$_{14}$ each independently represents hydrogen or C$_{1-3}$ alkyl), trifluoromethyl, trifluoromethoxy, difluoromethoxy, fluoro, chloro, bromo, cyano, acetyl, nitro, amino, borono, carboxyl, C$_{1-6}$ alkoxycarbonyl, phenyl, phenoxy, phenoxycarbonyl, benzyloxy, hydroxyl, trimethylsilyloxy, diphenyl-t-butylsilyloxy, hydroxymethyl, —SO$_3$H, —SO$_2$CH$_3$, —SO$_2$NHR$_{15}$ (wherein R$_{15}$ is hydrogen or C$_{1-3}$ alkyl), or —O(CH$_2$)$_n$ OR$_{16}$— (wherein R$_{16}$ is hydrogen or C$_{1-3}$ alkyl, and n is 1, 2 or 3); or when any two R$_i$s are located at the ortho position to each other, they together form -Z$_1$=Z$_2$-Z$_3$=Z$_4$- (wherein Z$_1$ through Z$_4$ each independently represents CH or N), —S—CO—O—, —CH=CH—NH—, —CH=CH—S—, —CH=CH—O—, —N=CH—NH—, —CH$_2$—N=N—, —N=N—O—, —N=CH—S— or —O—CH$_2$CH$_2$—O—;

with the proviso that when R$_1$=R$_2$=R$_3$=R$_4$=R$_5$=R$_6$=R$_9$=hydrogen; R$_7$ is not H, OH or C(CH$_3$)$_3$.

In another embodiment of the fifth embodiment,

R$_1$ and R$_4$ are each hydrogen;

R$_2$ and R$_3$ are each independently hydrogen, fluoro, chloro, bromo, cyano, acetyl, amino, borono, nitro, carboxyl, C$_{1-4}$ alkoxycarbonyl, phenoxycarbonyl, hydroxyl, —SO$_3$H, —SO$_2$CH$_3$ and —SO$_2$NH$_2$;

R$_5$ through R$_9$ are each independently hydrogen, C$_{1-4}$ alkyl, C$_{3-6}$ cycloalkyl, C$_{1-3}$ alkoxy, trifluoromethyl, fluoro, chloro, bromo, cyano, acetyl, amino, borono, nitro, carboxyl, C$_{1-4}$ alkoxycarbonyl, phenyl, phenoxy, phenoxycarbonyl, benzyloxy, hydroxyl, hydroxymethyl, —SO$_3$H, —SO$_2$CH$_3$, —SO$_2$NH$_2$, or when any two R$_i$s are located at the ortho position to each other, they together form -Z$_1$=Z$_2$-Z$_3$=Z$_4$- (wherein Z$_1$ through Z$_4$ each independently represents CH or N), —S—CO—O—, —CH=CH—NH—, —CH=CH—S—, —CH=CH—O—, —N=CH—NH—, —CH$_2$—N=N—, —N=N—O—, —N=CH—S— or —O—CH$_2$CH$_2$—O—;

with the proviso that when R$_1$=R$_2$=R$_3$=R$_4$=R$_5$=R$_6$=R$_8$=R$_9$=hydrogen; R$_7$ is not H, OH or C(CH$_3$)$_3$.

In a sixth embodiment, the compounds of the present invention are represented by formula A(VI):

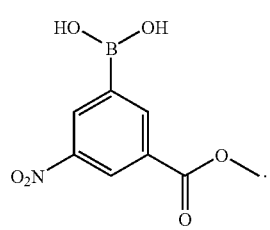

A(VI)

In a seventh embodiment, the compounds of the present invention are represented by formula A(VII):

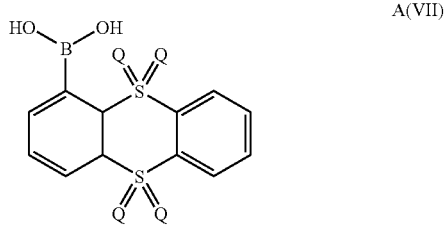

A(VII)

wherein Q is oxygen or lone-pair electrons.

In an eighth embodiment, the compounds of the present invention are represented by formula A(VIII):

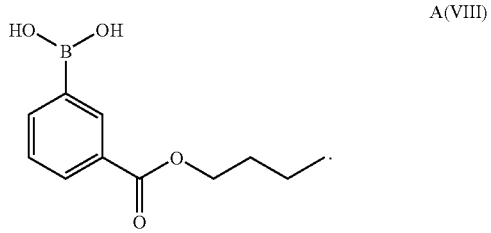

A(VIII)

In a ninth embodiment, the compounds of the present invention are represented by formula A(IX):

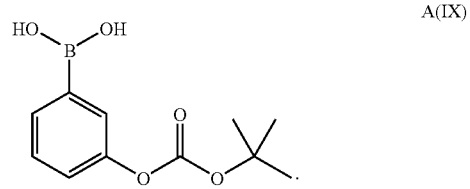

A(IX)

In a tenth embodiment, the compounds of the present invention are represented by formula A(X):

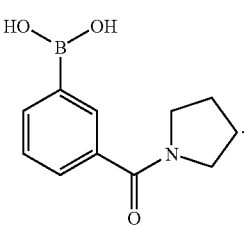

A(X)

In an eleventh embodiment, the compounds of the present invention are represented by formula A(XI):

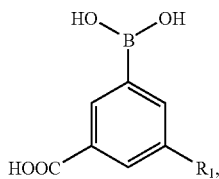

A(XI)

wherein $R_1$ is hydrogen, $C_{1-6}$ alkyl, $C_{3-6}$ cycloalkyl, $C_{1-3}$ alkoxy, n-butoxy, i-butoxy, sec-butoxy, $R_{13}R_{14}N$— (wherein $R_{13}$ and $R_{14}$ are each independently hydrogen or $C_{1-3}$ alkyl), trifluoromethyl, trifluoromethoxy, difluoromethoxy, fluoro, chloro, bromo, cyano, acetyl, amino, borono, nitro, carboxyl, $C_{1-6}$ alkoxycarbonyl, phenyl, phenoxy, phenoxycarbonyl, benzyloxy, hydroxyl, trimethylsilyloxy, diphenyl-t-butylsilyloxy, hydroxymethyl, —$SO_3H$, —$SO_2CH_3$, —$SO_2NHR_{15}$ (wherein $R_{15}$ is hydrogen or $C_{1-3}$ alkyl), or —$O(CH_2)_nOR_{16}$— (wherein $R_{16}$ is hydrogen or $C_{1-3}$ alkyl, and n is 1, 2 or 3).

In a preferred embodiment of the eleventh embodiment, $R_1$ is hydrogen, fluoro, chloro, bromo, cyano, acetyl, amino, borono, nitro, carboxyl, $C_{1-4}$ alkoxycarbonyl, phenoxycarbonyl, hydroxyl, —$SO_3H$, —$SO_2CH_3$ and —$SO_2NH_2$.

In one particular embodiment of the eleventh embodiment, the compounds of the present invention are represented by formula A(XI),
wherein $R_1$ is $C_{1-6}$ alkyl, $C_{3-6}$ cycloalkyl, $C_{1-3}$ alkoxy, n-butoxy, i-butoxy, sec-butoxy, $R_{13}R_{14}N$— (wherein $R_{13}$ and $R_{14}$ are each independently hydrogen or $C_{1-3}$ alkyl), trifluoromethyl, trifluoromethoxy, difluoromethoxy, fluoro, chloro, bromo, cyano, acetyl, carboxyl, $C_{1-6}$ alkoxycarbonyl, phenyl, phenoxy, phenoxycarbonyl, benzyloxy, hydroxyl, trimethylsilyloxy, diphenyl-t-butylsilyloxy, hydroxymethyl, —$SO_3H$, —$SO_2CH_3$, —$SO_2NHR_{15}$ (wherein $R_{15}$ is hydrogen or $C_{1-3}$ alkyl), or —$O(CH_2)_nOR_{16}$— (wherein $R_{16}$ is hydrogen or $C_{1-3}$ alkyl, and n is 1, 2 or 3).

In another embodiment of the eleventh embodiment,
$R_1$ is fluoro, chloro, bromo, cyano, acetyl, carboxyl, $C_{1-4}$ alkoxycarbonyl, phenoxycarbonyl, hydroxyl, —$SO_3H$, —$SO_2CH_3$ and —$SO_2NH_2$.

In a twelfth embodiment, the compounds of the present invention are represented by formula A(XII):

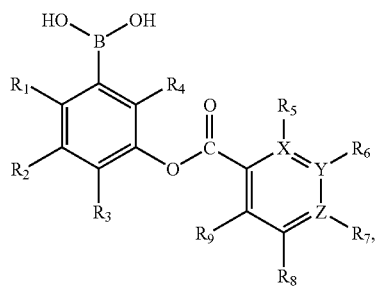

A(XII)

wherein $R_1$ through $R_9$ are each independently
(i) when connected to a carbon atom:
hydrogen, $C_{1-6}$ alkyl, $C_{3-6}$ cycloalkyl, $C_{1-3}$ alkoxy, n-butoxy, i-butoxy, sec-butoxy, $R_{13}R_{14}N$— (wherein $R_{13}$ and $R_{14}$ are each independently hydrogen or $C_{1-3}$ alkyl), trifluoromethyl, trifluoromethoxy, difluoromethoxy, fluoro, chloro, bromo, cyano, acetyl, amino, borono, nitro, carboxyl, $C_{1-6}$ alkoxycarbonyl, phenyl, phenoxy, phenoxycarbonyl, benzyloxy, hydroxyl, trimethylsilyloxy, diphenyl-t-butylsilyloxy, hydroxymethyl, —CHO, —CH=NOH, —C=NOHCH_3, —$SO_3H$, —$SO_2CH_3$, —$SO_2NHR_{15}$ (wherein $R_{15}$ is hydrogen or $C_{1-3}$ alkyl), or —$O(CH_2)_nOR_{16}$— (wherein $R_{16}$ is hydrogen or $C_{1-3}$ alkyl, and n is 1, 2 or 3); or when any two $R_i$s are located at the ortho position to each other, they together form -$Z_1$=$Z_2$-$Z_3$=$Z_4$- (wherein $Z_1$ through $Z_4$ each independently represents CH or N), —S—CO—O—, —CH=CH—NH—, —CH=CH—S—, —CH=CH—O—, —N=CH—NH—, —CH_{S2}—N=N—, —N=N—O—, —N=CH—S— or —O—CH_2CH_2—O—; or
(ii) when connected to a nitrogen atom;
absent;
and
X, Y and Z are each independently carbon or nitrogen.

In a preferred embodiment of the twelveth embodiment, $R_1$, $R_3$ and $R_4$ are each hydrogen;
$R_2$ is hydrogen, fluoro, chloro, bromo, cyano, acetyl, amino, nitro, carboxyl, $C_{1-4}$ alkoxycarbonyl, phenoxycarbonyl, hydroxyl, —CHO, —CH=NOH, —C=NOHCH_3, —$SO_3H$, —$SO_2CH_3$ and —$SO_2NH_2$;
$R_5$ is:
(i) when X is nitrogen:
absent, and
(ii) when X is carbon:
hydrogen, $C_{1-4}$ alkyl, $C_{3-6}$ cycloalkyl, $C_{1-3}$ alkoxy, trifluoromethyl, fluoro, chloro, bromo, cyano, acetyl, amino, borono, nitro, carboxyl, $C_{1-4}$ alkoxycarbonyl, phenyl, phenoxy, phenoxycarbonyl, benzyloxy, hydroxyl, hydroxymethyl, —CHO, —CH=NOH, —C=NOHCH_3, —$SO_3H$, —$SO_2CH_3$, —$SO_2NH_2$, or when $R_5$ are located at the ortho position to another $R_i$, they together form -$Z_1$=$Z_2$-$Z_3$=$Z_4$- (wherein $Z_1$ through $Z_4$ each independently represents CH or N), —S—CO—O—, —CH=CH—NH—, —CH=CH—S—, —CH=CH—O—, —N=CH—NH—, —CH_2—N=N—, —N=N—O—, —N=CH—S— or —O—CH_2CH_2—O—;
$R_6$ is:
(i) when Y is nitrogen:
absent, and
(ii) when Y is carbon:
hydrogen, $C_{1-4}$ alkyl, $C_{3-6}$ cycloalkyl, $C_{1-3}$ alkoxy, trifluoromethyl, fluoro, chloro, bromo, cyano, acetyl, amino, borono, nitro, carboxyl, $C_{1-4}$ alkoxycarbonyl, phenyl, phenoxy, phenoxycarbonyl, benzyloxy, hydroxyl, hydroxymethyl, —CHO, —CH=NOH, —C=NOHCH_3, —$SO_3H$, —$SO_2CH_3$, —$SO_2NH_2$, or when $R_6$ are located at the ortho position to another $R_i$, they together form -$Z_1$=$Z_2$-$Z_3$=$Z_4$- (wherein $Z_1$ through $Z_4$ each independently represents CH or N), —S—CO—O—, —CH=CH—NH—, —CH=CH—S—, —CH=CH—O—, —N=CH—NH—, —CH_2—N=N—, —N=N—O—, —N=CH—S— or —O—CH_2CH_2—O—;
$R_7$ is:
(i) when Z is nitrogen:
absent, and (ii) when Z is carbon:

hydrogen, $C_{1-4}$ alkyl, $C_{3-6}$ cycloalkyl, $C_{1-3}$ alkoxy, trifluoromethyl, fluoro, chloro, bromo, cyano, acetyl, amino, borono, nitro, carboxyl, $C_{1-4}$ alkoxycarbonyl, phenyl, phenoxy, phenoxycarbonyl, benzyloxy, hydroxyl, hydroxymethyl, —CHO, —CH=NOH, —C=NOHCH$_3$, —SO$_3$H, —SO$_2$CH$_3$, —SO$_2$NH$_2$, or when $R_7$ are located at the ortho position to another $R_i$, they together form -$Z_1$=$Z_2$-$Z_3$=$Z_4$- (wherein $Z_1$ through $Z_4$ each independently represents CH or N), —S—CO—O—, —CH=CH—NH—, —CH=CH—S—, —CH=CH—O—, —N=CH—NH—, —CH$_2$—N=N—, —N=N—O—, —N=CH—S— or —O—CH$_2$CH$_2$—O—;

$R_8$ through $R_9$ are each independently hydrogen, $C_{1-4}$ alkyl, $C_{3-6}$ cycloalkyl, $C_{1-3}$ alkoxy, trifluoromethyl, fluoro, chloro, bromo, cyano, acetyl, amino, borono, nitro, carboxyl, $C_{1-4}$ alkoxycarbonyl, phenyl, phenoxy, phenoxycarbonyl, benzyloxy, hydroxyl, hydroxymethyl, —CHO, —CH=NOH, —C=NOHCH$_3$, —SO$_3$H, —SO$_2$CH$_3$, —SO$_2$NH$_2$, or when any two $R_i$s are located at the ortho position to each other, they together form -$Z_1$=$Z_2$-$Z_3$=$Z_4$- (wherein $Z_1$ through $Z_4$ each independently represents CH or N), —S—CO—O—, —CH=CH—NH—, —CH=CH—S—, —CH=CH—O—, —N=CH—NH—, —CH$_2$—N=N—, —N=N—O—, —N=CH—S— or —O—CH$_2$CH$_2$—O—; and X, Y and Z are each independently carbon or nitrogen.

In a thirteenth embodiment, the compounds of the present invention are represented by formula A(XIII):

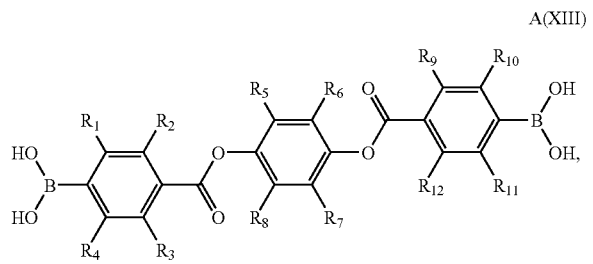

A(XIII)

wherein $R_1$ through $R_{12}$ are each independently hydrogen, $C_{1-6}$ alkyl, $C_{3-6}$ cycloalkyl, $C_{1-3}$ alkoxy, n-butoxy, i-butoxy, sec-butoxy, $R_{13}R_{14}N$— (wherein $R_{13}$ and $R_{14}$ are each independently hydrogen or $C_{1-3}$ alkyl), trifluoromethyl, trifluoromethoxy, difluoromethoxy, fluoro, chloro, bromo, cyano, acetyl, amino, borono, nitro, carboxyl, $C_{1-6}$ alkoxycarbonyl, phenyl, phenoxy, phenoxycarbonyl, benzyloxy, hydroxyl, trimethylsilyloxy, diphenyl-t-butylsilyloxy, hydroxymethyl, —SO$_3$H, —SO$_2$CH$_3$, —SO$_2$NHR$_{15}$ (wherein $R_{15}$ is hydrogen or $C_{1-3}$ alkyl), or —O(CH$_2$)$_n$OR$_{16}$— (wherein $R_{16}$ is hydrogen or $C_{1-3}$ alkyl, and n is 1, 2 or 3); or when any two $R_i$s are located at the ortho position to each other, they together form -$Z_1$=$Z_2$-$Z_3$=$Z_4$- (wherein $Z_1$ through $Z_4$ each independently represents CH or N), —S—CO—O—, —CH=CH—NH—, —CH=CH—S—, —CH=CH—O—, —N=CH—NH—, —CH$_2$—N=N—, —N=N—O—, —N=CH—S— or —O—CH$_2$CH$_2$—O—.

In a preferred embodiment of the thirteenth embodiment, $R_1$, $R_3$, $R_4$, $R_9$, $R_{11}$ and $R_{12}$ are each hydrogen;

$R_2$ and $R_{10}$ are each independently hydrogen, fluoro, chloro, bromo, cyano, acetyl, nitro, amino, borono, carboxyl, $C_{1-4}$ alkoxycarbonyl, phenoxycarbonyl, hydroxyl, —SO$_3$H, —SO$_2$CH$_3$ and —SO$_2$NH$_2$;

$R_5$ through $R_8$ are each independently hydrogen, $C_{1-4}$ alkyl, $C_{3-6}$ cycloalkyl, $C_{1-3}$ alkoxy, trifluoromethyl, fluoro, chloro, bromo, cyano, acetyl, amino, borono, nitro, carboxyl, $C_{1-4}$ alkoxycarbonyl, phenyl, phenoxy, phenoxycarbonyl, benzyloxy, hydroxyl, hydroxymethyl, —SO$_3$H, —SO$_2$CH$_3$, —SO$_2$NH$_2$, or when any two $R_i$s are located at the ortho position to each other, they together form -$Z_1$=$Z_2$-$Z_3$=$Z_4$- (wherein $Z_1$ through $Z_4$ each independently represents CH or N), —S—CO—O—, —CH=CH—NH—, —CH=CH—S—, —CH=CH—O—, —N=CH—NH—, —CH$_2$—N=N—, —N=N—O—, —N=CH—S— or —O—CH$_2$CH$_2$—O—.

In a fourteenth embodiment, the compounds of the present invention are represented by formula A(XIV):

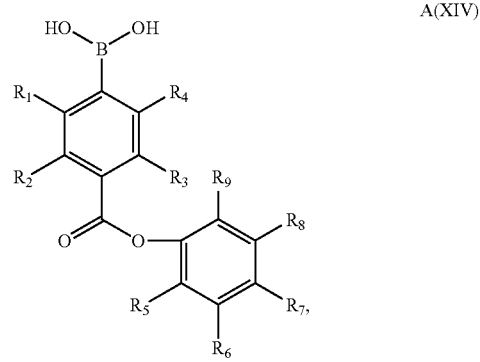

A(XIV)

wherein $R_1$ through $R_9$ are each independently hydrogen, $C_{1-6}$ alkyl, $C_{3-6}$ cycloalkyl, $C_{1-3}$ alkoxy, n-butoxy, i-butoxy, sec-butoxy, $R_{13}R_{14}N$— (wherein $R_{13}$ and $R_{14}$ each independently represents hydrogen or $C_{1-3}$ alkyl), trifluoromethyl, trifluoromethoxy, difluoromethoxy, fluoro, chloro, bromo, cyano, acetyl, nitro, amino, borono, carboxyl, $C_{1-6}$ alkoxycarbonyl, phenyl, phenoxy, phenoxycarbonyl, benzyloxy, hydroxyl, trimethylsilyloxy, diphenyl-t-butylsilyloxy, hydroxymethyl, —SO$_3$H, —SO$_2$CH$_3$, —SO$_2$NHR$_{15}$ (wherein $R_{15}$ is hydrogen or $C_{1-3}$ alkyl), or —O(CH$_2$)$_n$OR$_{16}$— (wherein $R_{16}$ is hydrogen or $C_{1-3}$ alkyl, and n is 1, 2 or 3); or when any two $R_i$s are located at the ortho position to each other, they together form -$Z_1$=$Z_2$-$Z_3$=$Z_4$- (wherein $Z_1$ through $Z_4$ each independently represents CH or N), —S—CO—O—, —CH=CH—NH—, —CH=CH—S—, —CH=CH—O—, —N=CH—NH—, —CH$_2$—N=N—, —N=N—O—, —N=CH—S— or —CH$_2$CH$_2$—O—.

In a preferred embodiment of the fourteenth embodiment, $R_1$ and $R_4$ are each hydrogen;

$R_2$ and $R_3$ are each independently hydrogen, fluoro, chloro, bromo, cyano, acetyl, amino, borono, nitro, carboxyl, $C_{1-4}$ alkoxycarbonyl, phenoxycarbonyl, hydroxyl, —SO$_3$H, —SO$_2$CH$_3$ and —SO$_2$NH$_2$;

$R_5$ through $R_9$ are each independently hydrogen, $C_{1-4}$ alkyl, $C_{3-6}$ cycloalkyl, $C_{1-3}$ alkoxy, trifluoromethyl, fluoro, chloro, bromo, cyano, acetyl, amino, borono, nitro, carboxyl, $C_{1-4}$ alkoxycarbonyl, phenyl, phenoxy, phenoxycarbonyl, benzyloxy, hydroxyl, hydroxymethyl, —SO$_3$H, —SO$_2$CH$_3$, —SO$_2$NH$_2$, or when any two $R_i$s are located at the ortho position to each other, they together form -$Z_1$=$Z_2$-$Z_3$=$Z_4$- (wherein $Z_1$ through $Z_4$ each independently represents CH or N), —S—CO—O—, —CH=CH—NH—, —CH=CH—S—, —CH=CH—O—, —N=CH—NH—, —CH$_2$—N=N—, —N=N—O—, —N=CH—S— or —O—CH$_2$CH$_2$—O—.

In a fifteenth embodiment, the compounds of the present invention are represented by formula A(XV):

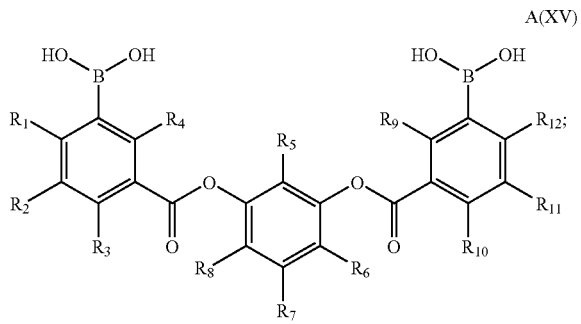

A(XV)

In certain embodiments, the invention is directed to compounds represented by formula A(XVI):

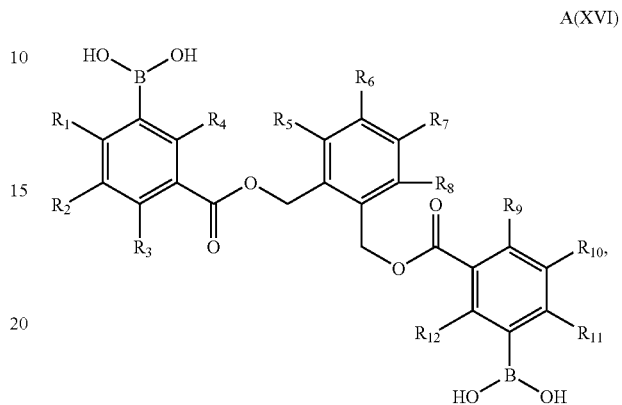

A(XVI)

wherein $R_1$ through $R_{12}$ are each independently hydrogen, $C_{1-6}$ alkyl, $C_{3-6}$ cycloalkyl, $C_{1-3}$ alkoxy, n-butoxy, i-butoxy, sec-butoxy, $R_{13}R_{14}N$— (wherein $R_{13}$ and $R_{14}$ are each independently hydrogen or $C_{1-3}$ alkyl), trifluoromethyl, trifluoromethoxy, difluoromethoxy, fluoro, chloro, bromo, cyano, acetyl, amino, borono, nitro, carboxyl, $C_{1-6}$ alkoxycarbonyl, phenyl, phenoxy, phenoxycarbonyl, benzyloxy, hydroxyl, trimethylsilyloxy, diphenyl-t-butylsilyloxy, hydroxymethyl, —$SO_3H$, —$SO_2CH_3$, —$SO_2NHR_{15}$ (wherein $R_{15}$ is hydrogen or $C_{1-3}$ alkyl), or —$O(CH_2)_n$$OR_{16}$— (wherein $R_{16}$ is hydrogen or $C_{1-3}$ alkyl, and n is 1, 2 or 3); or when any two $R_i$s are located at the ortho position to each other, they together form -$Z_1$=$Z_2$-$Z_3$=$Z_4$- (wherein $Z_1$ through $Z_4$ each independently represents CH or N), —S—CO—O—, —CH=CH—NH—, —CH=CH—S—, —CH=CH—O—, —N=CH—NH—, —$CH_2$—N=N—, —N=N—O—, —N=CH—S— or —O—$CH_2CH_2$—O—.

In a preferred embodiment of the fifteenth embodiment, $R_1$, $R_3$, $R_4$, $R_9$, $R_{11}$ and $R_{12}$ are each hydrogen;

$R_2$ and $R_{10}$ are each independently hydrogen, fluoro, chloro, bromo, cyano, acetyl, nitro, amino, borono, carboxyl, $C_{1-4}$ alkoxycarbonyl, phenoxycarbonyl, hydroxyl, —$SO_3H$, —$SO_2CH_3$ and —$SO_2NH_2$;

$R_5$ through $R_8$ are each independently hydrogen, $C_{1-4}$ alkyl, $C_{3-6}$ cycloalkyl, $C_{1-3}$ alkoxy, trifluoromethyl, fluoro, chloro, bromo, cyano, acetyl, amino, borono, nitro, carboxyl, $C_{1-4}$ alkoxycarbonyl, phenyl, phenoxy, phenoxycarbonyl, benzyloxy, hydroxyl, hydroxymethyl, —$SO_3H$, —$SO_2CH_3$, —$SO_2NH_2$, or when any two $R_i$s are located at the ortho position to each other, they together form -$Z_1$=$Z_2$-$Z_3$=$Z_4$- (wherein $Z_1$ through $Z_4$ each independently represents CH or N), —S—CO—O—, —CH=CH—NH—, —CH=CH—S—, —CH=CH—O—, —N=CH—NH—, —$CH_2$—N=N—, —N=N—O—, —N=CH—S— or —O—$CH_2CH_2$—O—.

In certain embodiments, the invention is directed to compounds represente by formula A(XVI) wherein, $R_1$, $R_3$, $R_4$, $R_9$, $R_{11}$ and $R_{12}$ are each hydrogen;

$R_2$ and $R_{10}$ are each independently hydrogen, fluoro, chloro, bromo, cyano, acetyl, nitro, amino, borono, carboxyl, $C_{1-4}$ alkoxycarbonyl, phenoxycarbonyl, hydroxyl, —$SO_3H$, —$SO_2CH_3$ and —$SO_2NH_2$;

$R_5$ through $R_8$ are each independently hydrogen, $C_{1-4}$ alkyl, $C_{3-6}$ cycloalkyl, $C_{1-3}$ alkoxy, trifluoromethyl, fluoro, chloro, bromo, cyano, acetyl, amino, borono, nitro, carboxyl, $C_{1-4}$ alkoxycarbonyl, phenyl, phenoxy, phenoxycarbonyl, benzyloxy, hydroxyl, hydroxymethyl, —$SO_3H$, —$SO_2CH_3$, —$SO_2NH_2$, or when any two $R_i$s are located at the ortho position to each other, they together form -$Z_1$=$Z_2$-$Z_3$=$Z_4$- (wherein $Z_1$ through $Z_4$ each independently represents CH or N), —S—CO—O—, —CH=CH—NH—, —CH=CH—S—, —CH=CH—O—, —N=CH—NH—, —$CH_2$—N=N—, —N=N—O—, —N=CH—S— or —O—$CH_2CH_2$—O—.

In certain embodiments, the invention is directed to compounds represented by formula A(XVII):

wherein $R_1$ through $R_{12}$ are each independently hydrogen, $C_{1-6}$ alkyl, $C_{3-6}$ cycloalkyl, $C_{1-3}$ alkoxy, n-butoxy, i-butoxy, sec-butoxy, $R_{13}R_{14}N-$ (wherein $R_{13}$ and $R_{14}$ are each independently hydrogen or $C_{1-3}$ alkyl), trifluoromethyl, trifluoromethoxy, difluoromethoxy, fluoro, chloro, bromo, cyano, acetyl, amino, borono, nitro, carboxyl, $C_{1-6}$ alkoxycarbonyl, phenyl, phenoxy, phenoxycarbonyl, benzyloxy, hydroxyl, trimethylsilyloxy, diphenyl-t-butylsilyloxy, hydroxymethyl, $-SO_3H$, $-SO_2CH_3$, $-SO_2NHR_{15}$ (wherein $R_{15}$ is hydrogen or $C_{1-3}$ alkyl), or $-O(CH_2)_n OR_{16}-$ (wherein $R_{16}$ is hydrogen or $C_{1-3}$ alkyl, and n is 1, 2 or 3); or when any two $R_is$ are located at the ortho position to each other, they together form $-Z_1=Z_2-Z_3=Z_4-$ (wherein $Z_1$ through $Z_4$ each independently represents CH or N), $-S-CO-O-$, $-CH=CH-NH-$, $-CH=CH-S-$, $-CH=CH-O-$, $-N=CH-NH-$, $-CH_2-N=N-$, $-N=N-O-$, $-N=CH-S-$ or $-O-CH_2CH_2-O-$.

In ertain preferred embodiments the invention is directed to compounds represented by formula A(XVII) wherein, $R_1$, $R_3$, $R_4$, $R_9$, $R_{11}$ and $R_{12}$ are each hydrogen;

$R_2$ and $R_{10}$ are each independently hydrogen, fluoro, chloro, bromo, cyano, acetyl, nitro, amino, borono, carboxyl, $C_{1-4}$ alkoxycarbonyl, phenoxycarbonyl, hydroxyl, $-SO_3H$, $-SO_2CH_3$ and $-SO_2NH_2$;

$R_5$ through $R_8$ are each independently hydrogen, $C_{1-4}$ alkyl, $C_{3-6}$ cycloalkyl, $C_{1-3}$ alkoxy, trifluoromethyl, fluoro, chloro, bromo, cyano, acetyl, amino, borono, nitro, carboxyl, $C_{1-4}$ alkoxycarbonyl, phenyl, phenoxy, phenoxycarbonyl, benzyloxy, hydroxyl, hydroxymethyl, $-SO_3H$, $-SO_2CH_3$, $-SO_2NH_2$, or when any two $R_is$ are located at the ortho position to each other, they together form $-Z_1=Z_2-Z_3=Z_4-$ (wherein $Z_1$ through $Z_4$ each independently represents CH or N), $-S-CO-O-$, $-CH=CH-NH-$, $-CH=CH-S-$, $-CH=CH-O-$, $-N=CH-NH-$, $-CH_2-N=N-$, $-N=N-O-$, $-N=CH-S-$ or $-O-CH_2CH_2-O-$.

In a certain embodiments, the invention is directed to compounds represented by formula A(XVIII):

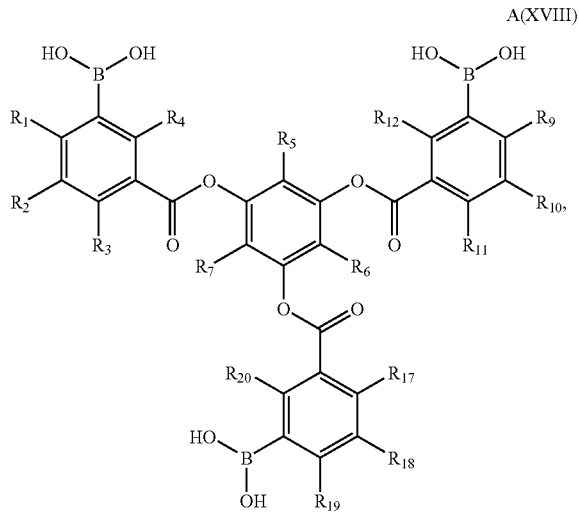

A(XVIII)

wherein $R_1$ through $R_{20}$ are each independently hydrogen, $C_{1-6}$ alkyl, $C_{3-6}$ cycloalkyl, $C_{1-3}$ alkoxy, n-butoxy, i-butoxy, sec-butoxy, $R_{13}R_{14}N-$ (wherein $R_{13}$ and $R_{14}$ are each independently hydrogen or $C_{1-3}$ alkyl), trifluoromethyl, trifluoromethoxy, difluoromethoxy, fluoro, chloro, bromo, cyano, acetyl, amino, borono, nitro, carboxyl, $C_{1-6}$ alkoxycarbonyl, phenyl, phenoxy, phenoxycarbonyl, benzyloxy, hydroxyl, trimethylsilyloxy, diphenyl-t-butylsilyloxy, hydroxymethyl, $-SO_3H$, $-SO_2CH_3$, $-SO_2NHR_{15}$ (wherein $R_{15}$ is hydrogen or $C_{1-3}$ alkyl), or $-O(CH_2)_n OR_{16}-$ (wherein $R_{16}$ is hydrogen or $C_{1-3}$ alkyl, and n is 1, 2 or 3); or when any two $R_is$ are located at the ortho position to each other, they together form $-Z_1=Z_2-Z_3=Z_4-$ (wherein $Z_1$ through $Z_4$ each independently represents CH or N), $-S-CO-O-$, $-CH=CH-NH-$, $-CH=CH-S-$, $-CH=CH-O-$, $-N=CH-NH-$, $-CH_2-N=N-$, $-N=N-O-$, $-N=CH-S-$ or $-O-CH_2CH_2-O-$.

In ertain preferred embodiments the invention is directed to compounds represented by formula A(XVIII) wherein, $R_1$, $R_3$, $R_4$, $R_9$, $R_{11}$, $R_{12}$, $R_{17}$, $R_{19}$ and $R_{20}$ are each hydrogen;

$R_2$, $R_{10}$ and $R_{18}$ are each independently hydrogen, fluoro, chloro, bromo, cyano, acetyl, nitro, amino, borono, carboxyl, $C_{1-4}$ alkoxycarbonyl, phenoxycarbonyl, hydroxyl, $-SO_3H$, $-SO_2CH_3$ and $-SO_2NH_2$;

$R_5$ through $R_7$ are each independently hydrogen, $C_{1-4}$ alkyl, $C_{3-6}$ cycloalkyl, $C_{1-3}$ alkoxy, trifluoromethyl, fluoro, chloro, bromo, cyano, acetyl, amino, borono, nitro, carboxyl, $C_{1-4}$ alkoxycarbonyl, phenyl, phenoxy, phenoxycarbonyl, benzyloxy, hydroxyl, hydroxymethyl, $-SO_3H$, $-SO_2CH_3$, $-SO_2NH_2$.

The invention relates to a method of inhibiting β-lactamase comprising contacting the β-lactamase with an effective amount of one or more compounds of formula A(I), A(II), A(III), A(IV), A(V), A(VI), A(VII), A(VIII), A(IX), A(X), A(XI), A(XII), A(XIII), A(XIV), A(XV), A(XVI), A(XVII) or A(XVIII).

The invention provides a method of treating bacterial infection, particularly β-lactam-antibiotic-resistant bacterial infection. The method comprises administering to a subject suffering from such an infection an effective amount of one or more compounds of formula A(I), A(II), A(III), A(IV), A(V), A(VI), A(VII), A(VIII), A(IX), A(X), A(XI), A(XII), A(XIII), A(XIV), A(XV), A(XVI), A(XVII), or A(XVIII).

The invention also provides a method of treating bacterial infection, particularly β-lactam-antibiotic-resistant bacterial infection. The method comprises administering a subject suffering from such an infection an effective amount of one or more compounds of formula A(I), A(II), A(III), A(IV), A(V), A(VI), A(VII), A(VIII), A(IX), A(X), A(XI), A(XII), A(XIII), A(XIV), A(XV), A(XVI), A(XVII), or A(XVIII); and an effective amount of β-lactam-antibiotic, with or without one or more other antibacterial agent.

The invention further provides a method of overcoming bacterial resistances, particularly resistance to β-lactam-antibiotic. The method comprises administering a subject an effective amount of one or more compounds of formula A(I), A(II), A(III), A(IV), A(V), A(VI), A(VII), A(VIII), A(IX), A(X), A(XI), A(XII), A(XIII), A(XIV), A(XV), A(XVI), A(XVII), or A(XVIII); and an effective amount of β-lactam-antibiotic, with or without one or more other antibacterial agent.

The invention also provides a pharmaceutical composition comprising one or more compounds of formula A(I), A(II), A(III), A(IV), A(V), A(VI), A(VII), A(VIII), A(IX), A(X), A(XI), A(XII), A(XIII), A(XIV), A(XV), A(XVI), A(XVII), or A(XVIII) and a pharmaceutically acceptable carrier.

The invention further provides a pharmaceutical composition comprising one or more compounds of formula A(I), A(II), A(III), A(IV), A(V), A(VI), A(VII), A(VIII), A(IX), A(X), A(XI), A(XII), A(XIII), A(XIV), A(XV), A(XVI), A(XVII), or A(XVIII); a β-lactam-antibiotic, and optionally comprising one or more other antibacterial agent; and a pharmaceutically acceptable carrier.

DETAILED DESCRIPTION

The present invention provides compounds having the formula:

$$(HO)_2\text{—B-T} \quad (A)$$

wherein B stands for boron, and
T has one of the following structures:

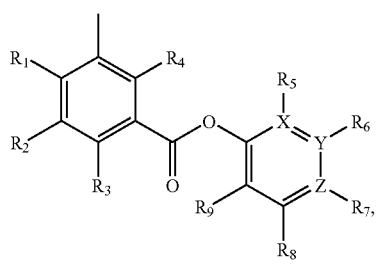
(I)

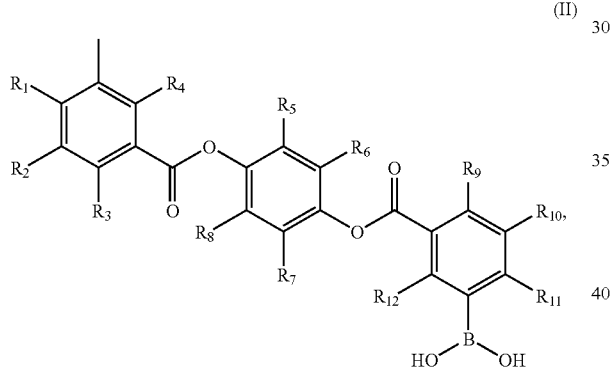
(II)

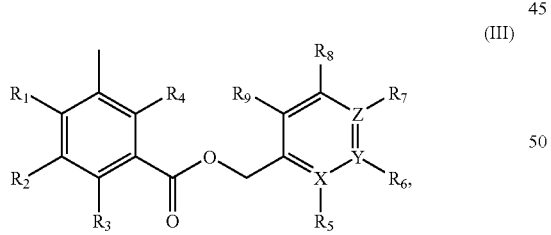
(III)

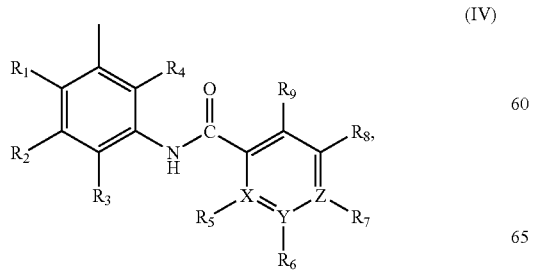
(IV)

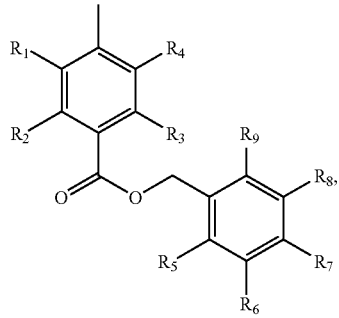
(V)

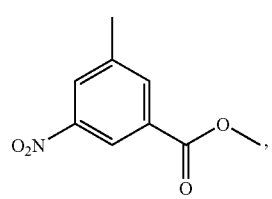
(VI)

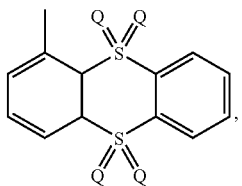
(VII)

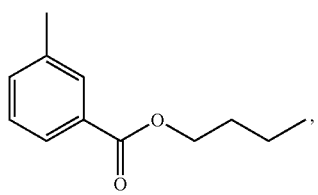
(VIII)

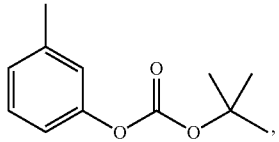
(IX)

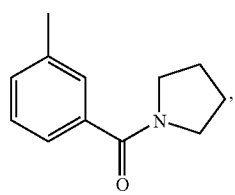
(X)

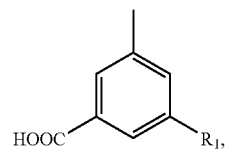
(XI)

-continued

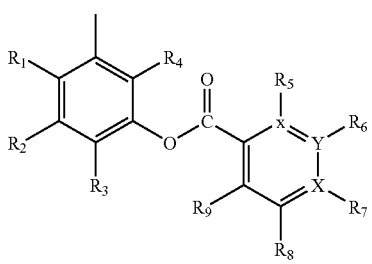
(XII)

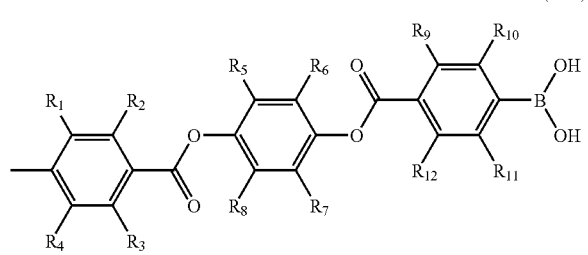
(XIII)

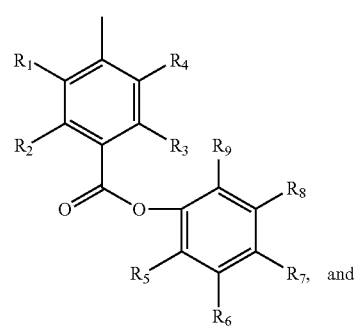
(XIV)

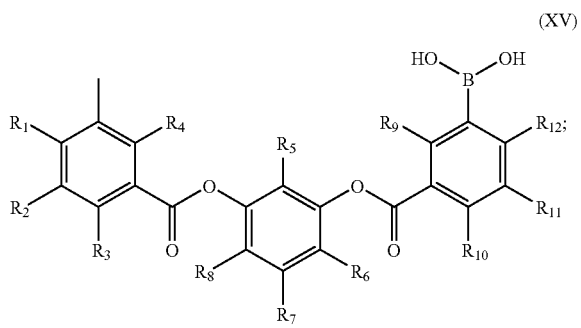
(XV)

wherein $R_1$ through $R_{12}$ are each independently
(i) when connected to a carbon atom:
hydrogen, $C_{1-6}$ alkyl, $C_{3-6}$ cycloalkyl, $C_{1-3}$ alkoxy, n-butoxy, i-butoxy, sec-butoxy, $R_{13}R_{14}N$— (wherein $R_{13}$ and $R_{14}$ are each independently hydrogen or $C_{1-3}$ alkyl), trifluoromethyl, trifluoromethoxy, difluoromethoxy, fluoro, chloro, bromo, cyano, acetyl, amino, borono, nitro, carboxyl, $C_{1-6}$ alkoxycarbonyl, phenyl, phenoxy, phenoxycarbonyl, benzyloxy, hydroxyl, trimethylsilyloxy, diphenyl-t-butylsilyloxy, hydroxymethyl, —CHO, —CH=NOH, —C=NOHCH$_3$, —SO$_3$H, —SO$_2$CH$_3$, —SO$_2$NHR$_{15}$ (wherein $R_{15}$ is hydrogen or $C_{1-3}$ alkyl), or —O(CH$_2$)$_n$OR$_{16}$— (wherein $R_{16}$ is hydrogen or $C_{1-3}$ alkyl, and n is 1, 2 or 3); or when any two $R_i$s are located at the ortho position to each other, they together form -$Z_1$=$Z_2$-$Z_3$=$Z_4$- (wherein $Z_1$ through $Z_4$ each independently represents CH or N), —S—CO—O—, —CH=CH—NH—, —CH=CH—S—, —CH=CH—O—, —N=CH—NH—, —CH$_2$—N=N—, —N=N—O—, —N=CH—S— or —O—CH$_2$CH$_2$—O—;

or (ii) when connected to a nitrogen atom:
absent;
and

X, Y and Z are each independently carbon or nitrogen.

The compounds of the present invention are specifically described by formula A(I), A(II), A(III), A(IV), A(V), A(VI), A(VII), A(VIII), A(IX), A(X), A(XI), A(XII), A(XIII), A(XIV), A(XV), A(XVI), A(XVII) and/or A(XVIII) below.

The invention relates to a method of inhibiting β-lactamase comprising contacting the β-lactamase with an effective amount of one or more compounds of formula A(I), A(II), A(III), A(IV), A(V), A(VI), A(VII), A(VIII), A(IX), A(X), A(XI), A(XII), A(XIII), A(XIV), A(XV), A(XVI), A(XVII) or A(XVIII).

The invention provides a method of treating bacterial infection, particularly β-lactam-antibiotic-resistant bacterial infection. The method comprises administering to a subject suffering from such an infection an effective amount of one or more compounds of formula A(I), A(II), A(III), A(IV), A(V), A(VI), A(VII), A(VIII), A(IX), A(X), A(XI), A(XII), A(XIII), A(XIV), A(XV), A(XVI), A(XVII) or A(XVIII).

The invention also provides a method of treating bacterial infection, particularly β-lactam-antibiotic-resistant bacterial infection. The method comprises administering a subject suffering from such an infection an effective amount of one or more compounds of formula A(I), A(II), A(III), A(IV), A(V), A(VI), A(VII), A(VIII), A(IX), A(X), A(XI), A(XII), A(XIII), A(XIV), A(XV), A(XVI), A(XVII) or A(XVIII); and an effective amount of β-lactam-antibiotic.

The invention further provides a method of overcoming bacterial resistances, particularly resistance to β-lactam-antibiotic. The method comprises administering a subject an effective amount of one or more compounds of formula A(I), A(II), A(III), A(IV), A(V), A(VI), A(VII), A(VIII), A(IX), A(X), A(XI), A(XII), A(XIII), A(XIV), A(XV), A(XVI), A(XVII) or A(XVIII); and an effective amount of β-lactam-antibiotic or other antibacterial agent.

The invention also provides a pharmaceutical composition comprising one or more compounds of formula A(I), A(II), A(III), A(IV), A(V), A(VI), A(VII), A(VIII), A(IX), A(X), A(XI), A(XII), A(XIII), A(XIV), A(XV), A(XVI), A(XVII) or A(XVIII); and a pharmaceutically acceptable carrier.

The invention further provides a pharmaceutical composition comprising one or more compounds of formula A(I), A(II), A(III), A(IV), A(V), A(VI), A(VII), A(VIII), A(IX), A(X), A(XI), A(XII), A(XIII), A(XIV), A(XV), A(XVI), A(XVII) or A(XVIII); a β-lactam-antibiotic or other antibacterial agent; and a pharmaceutically acceptable carrier.

Formula A(I)

In a first embodiment, the compounds of the present invention are represented by formula A(I):

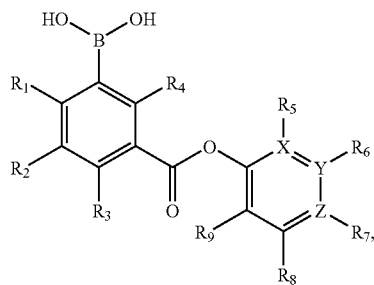

A(I)

wherein $R_1$ through $R_9$ are each independently (i) when connected to a carbon atom:

hydrogen, $C_{1-6}$ alkyl, $C_{3-6}$ cycloalkyl, $C_{1-3}$ alkoxy, n-butoxy, i-butoxy, sec-butoxy, $R_{13}R_{14}N$— (wherein $R_{13}$ and $R_{14}$ are each independently hydrogen or $C_{1-3}$ alkyl), trifluoromethyl, trifluoromethoxy, difluoromethoxy, fluoro, chloro, bromo, cyano, acetyl, amino, borono, nitro, carboxyl, $C_{1-6}$ alkoxycarbonyl, phenyl, phenoxy, phenoxycarbonyl, benzyloxy, hydroxyl, trimethylsilyloxy, diphenyl-t-butylsilyloxy, hydroxymethyl, —CHO, —CH=NOH, —C=NOHCH$_3$, —SO$_3$H, —SO$_2$CH$_3$, —SO$_2$NHR$_{15}$ (wherein $R_{15}$ is hydrogen or $C_{1-3}$ alkyl), or —O(CH$_2$)$_n$OR$_{16}$— (wherein $R_{16}$ is hydrogen or $C_{1-3}$ alkyl, and n is 1, 2 or 3); or when any two $R_i$s are located at the ortho position to each other, they together form -Z$_1$=Z$_2$-Z$_3$=Z$_4$- (wherein $Z_1$ through $Z_4$ each independently represents CH or N), —S—CO—O—, —CH=CH—NH—, —CH=CH—S—, —CH=CH—O—, —N=CH—NH—, —CH$_2$—N=N—, —N=N—O—, —N=CH—S— or —O—CH$_2$CH$_2$—O—; or (ii) when connected to a nitrogen atom;

absent;

and

X, Y and Z are each independently carbon or nitrogen.

In a preferred embodiment of the first embodiment, $R_1$, $R_3$ and $R_4$ are each hydrogen;

$R_2$ is hydrogen, fluoro, chloro, bromo, cyano, acetyl, amino, nitro, carboxyl, $C_{1-4}$ alkoxycarbonyl, phenoxycarbonyl, hydroxyl, —CHO, —CH=NOH, —C=NOHCH$_3$, —SO$_3$H, —SO$_2$CH$_3$ and —SO$_2$NH$_2$;

$R_5$ is:

(i) when X is nitrogen:

absent, and (ii) when X is carbon:

hydrogen, $C_{1-4}$ alkyl, $C_{3-6}$ cycloalkyl, $C_{1-3}$ alkoxy, trifluoromethyl, fluoro, chloro, bromo, cyano, acetyl, amino, borono, nitro, carboxyl, $C_{1-4}$ alkoxycarbonyl, phenyl, phenoxy, phenoxycarbonyl, benzyloxy, hydroxyl, hydroxymethyl, —CHO, —CH=NOH, —C=NOHCH$_3$, —SO$_3$H, —SO$_2$CH$_3$, —SO$_2$NH$_2$, or when $R_5$ are located at the ortho position to another $R_i$, they together form -Z$_1$=Z$_2$-Z$_3$=Z$_4$- (wherein $Z_1$ through $Z_4$ each independently represents CH or N), —S—CO—O—, —CH=CH—NH—, —CH=CH—S—, —CH=CH—O—, —N=CH—NH—, —CH$_2$—N=N—, —N=N—O—, —N=CH—S— or —O—CH$_2$CH$_2$—O—;

$R_6$ is:

(i) when Y is nitrogen:

absent, and (ii) when Y is carbon:

hydrogen, $C_{1-4}$ alkyl, $C_{3-6}$ cycloalkyl, $C_{1-3}$ alkoxy, trifluoromethyl, fluoro, chloro, bromo, cyano, acetyl, amino, borono, nitro, carboxyl, $C_{1-4}$ alkoxycarbonyl, phenyl, phenoxy, phenoxycarbonyl, benzyloxy, hydroxyl, hydroxymethyl, —CHO, —CH=NOH, —C=NOHCH$_3$, —SO$_3$H, —SO$_2$CH$_3$, —SO$_2$NH$_2$, or when $R_6$ are located at the ortho position to another $R_i$, they together form -Z$_1$=Z$_2$-Z$_3$=Z$_4$- (wherein $Z_1$ through $Z_4$ each independently represents CH or N), —S—CO—O—, —CH=CH—NH—, —CH=CH—S—, —CH=CH—O—, —N=CH—NH—, —CH$_2$—N=N—, —N=N—O—, —N=CH—S— or —O—CH$_2$CH$_2$—O—;

$R_7$ is:

(i) when Z is nitrogen:

absent, and (ii) when Z is carbon:

hydrogen, $C_{1-4}$ alkyl, $C_{3-6}$ cycloalkyl, $C_{1-3}$ alkoxy, trifluoromethyl, fluoro, chloro, bromo, cyano, acetyl, amino, borono, nitro, carboxyl, $C_{1-4}$ alkoxycarbonyl, phenyl, phenoxy, phenoxycarbonyl, benzyloxy, hydroxyl, hydroxymethyl, —CHO, —CH=NOH, —C=NOHCH$_3$, —SO$_3$H, —SO$_2$CH$_3$, —SO$_2$NH$_2$, or when $R_7$ are located at the ortho position to another $R_i$, they together form -Z$_1$=Z$_2$-Z$_3$=Z$_4$- (wherein $Z_1$ through $Z_4$ each independently represents CH or N), —S—CO—O—, —CH=CH—NH—, —CH=CH—O—, —N=CH—NH—, —CH$_2$—N=N—, —N=N—O—, —N=CH—S— or —O—CH$_2$CH$_2$—O—;

$R_8$ through $R_9$ are each independently hydrogen, $C_{1-4}$ alkyl, $C_{3-6}$ cycloalkyl, $C_{1-3}$ alkoxy, trifluoromethyl, fluoro, chloro, bromo, cyano, acetyl, amino, borono, nitro, carboxyl, $C_{1-4}$ alkoxycarbonyl, phenyl, phenoxy, phenoxycarbonyl, benzyloxy, hydroxyl, hydroxymethyl, —CHO, —CH=NOH, —C=NOHCH$_3$, —SO$_3$H, —SO$_2$CH$_3$, —SO$_2$NH$_2$, or when any two $R_i$s are located at the ortho position to each other, they together form -Z$_1$=Z$_2$-Z$_3$=Z$_4$- (wherein $Z_1$ through $Z_4$ each independently represents CH or N), —S—CO—O—, —CH=CH—NH—, —CH=CH—S—, —CH=CH—O—, —N=CH—NH—, —CH$_2$—N=N—, —N=N—O—, —N=CH—S— or —O—CH$_2$CH$_2$—O—; and X, Y and Z are each independently carbon or nitrogen.

Non-limiting specific compounds described by formula A(I) are listed in Table 1.

TABLE 1

Representative Compounds in Formula A(I):

| $R_1$ | $R_2$ | $R_3$ | $R_4$ | $R_5$ | $R_6$ | $R_7$ | $R_8$ | $R_9$ | X | Y | Z |
|---|---|---|---|---|---|---|---|---|---|---|---|
| H | NO$_2$ | H | H | H | H | NO$_2$ | H | H | C | C | C |
| H | NO$_2$ | H | H | NO$_2$ | H | H | H | H | C | C | C |

TABLE 1-continued

Representative Compounds in Formula A(I):

| $R_1$ | $R_2$ | $R_3$ | $R_4$ | $R_5$ | $R_6$ | $R_7$ | $R_8$ | $R_9$ | X | Y | Z |
|---|---|---|---|---|---|---|---|---|---|---|---|
| H | $NO_2$ | H | H | H | $NO_2$ | H | H | H | C | C | C |
| H | $NO_2$ | H | H | H | H | $OCH_3$ | H | H | C | C | C |
| H | $NO_2$ | H | H | H | H | $COOCH_2CH_3$ | H | H | C | C | C |
| H | $NO_2$ | H | H | H | [1,3]oxathiol-2-one | | H | H | C | C | C |
| H | $NO_2$ | H | H | CN | H | H | H | H | C | C | C |
| H | $NO_2$ | H | H | Cl | H | H | H | $NO_2$ | C | C | C |
| H | $NO_2$ | H | H | $COOCH_2CH_3$ | H | H | H | H | C | C | C |
| H | $NO_2$ | H | H | Cl | H | H | H | H | C | C | C |
| H | $NO_2$ | H | H | $CH_3$ | H | H | H | H | C | C | C |
| H | $NO_2$ | H | H | $OCH_3$ | H | H | H | H | C | C | C |
| H | $NO_2$ | H | H | H | $CH_3$ | H | H | H | C | C | C |
| H | $NO_2$ | H | H | Cl | H | H | H | Cl | C | C | C |
| H | $NO_2$ | H | H | F | H | H | H | H | C | C | C |
| H | $NO_2$ | H | H | F | H | H | H | F | C | C | C |
| H | $NO_2$ | H | H | H | H | F | H | H | C | C | C |
| H | $NO_2$ | H | H | H | H | — | H | H | C | C | N |
| H | $NO_2$ | H | H | Cl | — | H | H | H | C | N | C |
| H | $NO_2$ | H | H | H | H | H | H | H | C | C | C |
| H | $NO_2$ | H | H | Br | H | H | H | H | C | C | C |
| H | $NO_2$ | H | H | H | $B(OH)_2$ | H | H | H | C | C | C |
| H | $NO_2$ | H | H | Cl | H | Cl | H | $NO_2$ | C | C | C |
| H | COOH | H | H | Cl | H | H | H | Cl | C | C | C |
| H | $NO_2$ | H | H | $COCH_3$ | H | H | H | H | C | C | C |
| H | $NO_2$ | H | H | H | —CH=CH—CH=CH— | | H | H | C | C | C |
| H | $NO_2$ | H | H | H | H | COOH | H | H | C | C | C |
| H | $NO_2$ | H | H | OH | H | H | H | H | C | C | C |
| H | $NO_2$ | H | H | $NH_2$ | H | H | H | H | C | C | C |
| H | $NO_2$ | H | H | CHO | H | H | H | H | C | C | C |
| H | $NO_2$ | H | H | CH=NOH | H | H | H | H | C | C | C |
| H | $NO_2$ | H | H | C=NOHCH_3 | H | H | H | H | C | C | C |
| H | H | $NO_2$ | H | Cl | H | H | H | Cl | C | C | C |
| H | H | Cl | H | Cl | H | H | H | Cl | C | C | C |
| H | H | H | H | Cl | H | H | H | Cl | C | C | C |
| H | $NO_2$ | H | H | 2,4-dichlorophenoxyl | H | H | Cl | H | C | C | C |
| H | $NO_2$ | H | H | Cl | H | Cl | H | Cl | C | C | C |

Formula A(II)

In a second embodiment, the compounds of the present invention are represented by formula A(II):

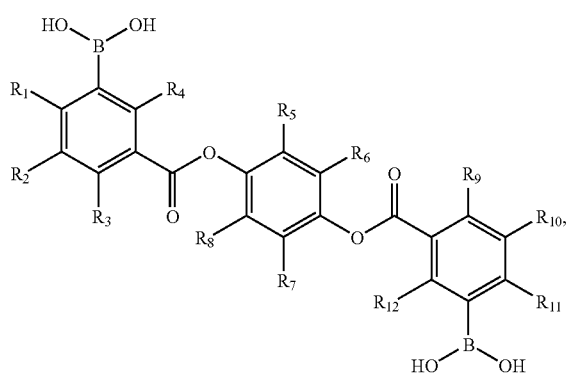

A(II)

wherein $R_1$ through $R_{12}$ are each independently hydrogen, $C_{1-6}$ alkyl, $C_{3-6}$ cycloalkyl, $C_{1-3}$ alkoxy, n-butoxy, i-butoxy, sec-butoxy, $R_{13}R_{14}N$— (wherein $R_{13}$ and $R_{14}$ are each independently hydrogen or $C_{1-3}$ alkyl), trifluoromethyl, trifluoromethoxy, difluoromethoxy, fluoro, chloro, bromo, cyano, acetyl, amino, borono, nitro, carboxyl, $C_{1-6}$ alkoxycarbonyl, phenyl, phenoxy, phenoxycarbonyl, benzyloxy, hydroxyl, trimethylsilyloxy, diphenyl-t-butylsilyloxy, hydroxymethyl, —$SO_3H$, —$SO_2CH_3$, —$SO_2NHR_{15}$ (wherein $R_{15}$ is hydrogen or $C_{1-3}$ alkyl), or —$O(CH_2)_n$ $OR_{16}$— (wherein $R_{16}$ is hydrogen or $C_{1-3}$ alkyl, and n is 1, 2 or 3); or when any two $R_i$s are located at the ortho position to each other, they together form -$Z_1$=$Z_2$-$Z_3$=$Z_4$- (wherein $Z_1$ through $Z_4$ each independently represents CH or N), —S—CO—O—, —CH=CH—NH—, —CH=CH—S—, —CH=CH—O—, —N=CH—NH—, —$CH_2$—N=N—, —N=N—O—, —N=CH—S— or —O—$CH_2CH_2$—O—.

In a preferred embodiment of the second embodiment, $R_1$, $R_3$, $R_4$, $R_9$, $R_{11}$ and $R_{12}$ are each hydrogen;

$R_2$ and $R_{10}$ are each independently hydrogen, fluoro, chloro, bromo, cyano, acetyl, nitro, amino, borono, carboxyl, $C_{1-4}$ alkoxycarbonyl, phenoxycarbonyl, hydroxyl, —$SO_3H$, —$SO_2CH_3$ and —$SO_2NH_2$;

$R_5$ through $R_8$ are each independently hydrogen, $C_{1-4}$ alkyl, $C_{3-6}$ cycloalkyl, $C_{1-3}$ alkoxy, trifluoromethyl, fluoro, chloro, bromo, cyano, acetyl, amino, borono, nitro, carboxyl, $C_{1-4}$ alkoxycarbonyl, phenyl, phenoxy, phenoxycarbonyl, benzyloxy, hydroxyl, hydroxymethyl, —$SO_3H$, —$SO_2CH_3$, —$SO_2NH_2$, or when any two $R_i$s are located at the ortho position to each other, they together form -$Z_1$=$Z_2$-$Z_3$=$Z_4$- (wherein $Z_1$ through $Z_4$ each independently represents CH or N), —S—CO—O—, —CH=CH—NH—, —CH=CH—S—, —CH=CH—O—, —N=CH—NH—, —$CH_2$—N=N—, —N=N—O—, —N=CH—S— or —O—$CH_2CH_2$—O—.

Non-limiting specific compounds described by formula A(II) are listed in Table 2.

TABLE 2

Representative Compounds in Formula A(II):

| $R_1$ | $R_2$ | $R_3$ | $R_4$ | $R_5$ | $R_6$ | $R_7$ | $R_8$ | $R_9$ | $R_{10}$ | $R_{11}$ | $R_{12}$ |
|---|---|---|---|---|---|---|---|---|---|---|---|
| H | $NO_2$ | H | H | H | H | H | H | H | $NO_2$ | H | H |
| H | $NO_2$ | H | H | Cl | H | H | H | H | $NO_2$ | H | H |
| H | H | $NO_2$ | H | Cl | H | H | H | $NO_2$ | H | H | H |
| H | H | H | H | Cl | H | H | H | H | H | H | H |
| H | $NO_2$ | H | H | Cl | Cl | Cl | Cl | H | $NO_2$ | H | H |
| H | $NO_2$ | H | H | t-butyl | H | H | H | H | $NO_2$ | H | H |

Formula A(III)

In a third embodiment, the compounds of the present invention are represented by formula A(III):

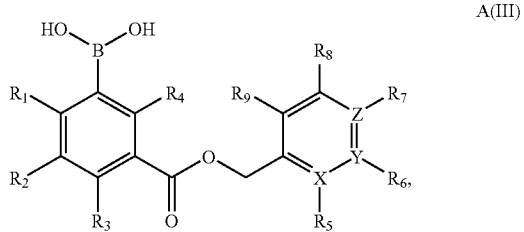

A(III)

wherein $R_1$ through $R_9$ are each independently (i) when connected to a carbon atom:
hydrogen, $C_{1-6}$ alkyl, $C_{3-6}$ cycloalkyl, $C_{1-3}$ alkoxy, n-butoxy, i-butoxy, sec-butoxy, $R_{13}R_{14}N$— (wherein $R_{13}$ and $R_4$ are each independently hydrogen or $C_{1-3}$ alkyl), trifluoromethyl, trifluoromethoxy, difluoromethoxy, fluoro, chloro, bromo, cyano, acetyl, amino, borono, nitro, carboxyl, $C_{1-6}$ alkoxycarbonyl, phenyl, phenoxy, phenoxycarbonyl, benzyloxy, hydroxyl, trimethylsilyloxy, diphenyl-t-butylsilyloxy, hydroxymethyl, —CHO, —CH=NOH, —C=NOHCH$_3$, —SO$_3$H, —SO$_2$CH$_3$, —SO$_2$NHR$_{15}$ (wherein $R_{15}$ is hydrogen or $C_{1-3}$ alkyl), or —O(CH$_2$)$_n$OR$_{16}$— (wherein $R_{16}$ is hydrogen or $C_{1-3}$ alkyl, and n is 1, 2 or 3); or when any two $R_i$s are located at the ortho position to each other, they together form -$Z_1$=$Z_2$-$Z_3$=$Z_4$- (wherein $Z_1$ through $Z_4$ each independently represents CH or N), —S—CO—O—, —CH=CH—NH—, —CH=CH—S—, —CH=CH—O—, —N=CH—NH—, —CH$_2$—N=N—, —N=N—O—, —N=CH—S— or —O—CH$_2$CH$_2$—O—; or (ii) when connected to a nitrogen atom;
absent;
and X, Y and Z are each independently carbon or nitrogen.

In a preferred embodiment of the third embodiment, $R_1$, $R_3$ and $R_4$ are each hydrogen;

$R_2$ is hydrogen, fluoro, chloro, bromo, cyano, acetyl, amino, nitro, carboxyl, $C_{1-4}$ alkoxycarbonyl, phenoxycarbonyl, hydroxyl, —CHO, —CH=NOH, —C=NOHCH$_3$, —SO$_3$H, —SO$_2$CH$_3$ and —SO$_2$NH$_2$;

$R_5$ is:

(i) when X is nitrogen:
absent, and (ii) when X is carbon:
hydrogen, $C_{1-4}$ alkyl, $C_{3-6}$ cycloalkyl, $C_{1-3}$ alkoxy, trifluoromethyl, fluoro, chloro, bromo, cyano, acetyl, amino, borono, nitro, carboxyl, $C_{1-4}$ alkoxycarbonyl, phenyl, phenoxy, phenoxycarbonyl, benzyloxy, hydroxyl, hydroxymethyl, —CHO, —CH=NOH, —C=NOHCH$_3$, —SO$_3$H, —SO$_2$CH$_3$, —SO$_2$NH$_2$, or when $R_5$ are located at the ortho position to another $R_i$, they together form -$Z_1$=$Z_2$-$Z_3$=$Z_4$- (wherein $Z_1$ through $Z_4$ each independently represents CH or N), —S—CO—O—, —CH=CH—NH—, —CH=CH—S—, —CH=CH—O—, —N=CH—NH—, —CH$_2$—N=N—, —N=N—O—, —N=CH—S— or —O—CH$_2$CH$_2$—O—;

$R_6$ is:

(i) when Y is nitrogen:
absent, and (ii) when Y is carbon:
hydrogen, $C_{1-4}$ alkyl, $C_{3-6}$ cycloalkyl, $C_{1-3}$ alkoxy, trifluoromethyl, fluoro, chloro, bromo, cyano, acetyl, amino, borono, nitro, carboxyl, $C_{1-4}$ alkoxycarbonyl, phenyl, phenoxy, phenoxycarbonyl, benzyloxy, hydroxyl, hydroxymethyl, —CHO, —CH=NOH, —C=NOHCH$_3$, —SO$_3$H, —SO$_2$CH$_3$, —SO$_2$NH$_2$, or when $R_6$ are located at the ortho position to another $R_i$, they together form -$Z_1$=$Z_2$-$Z_3$=$Z_4$- (wherein $Z_1$ through $Z_4$ each independently represents CH or N), —S—CO—O—, —CH=CH—NH—, —CH=CH—S—, —CH=CH—O—, —N=CH—NH—, —CH$_2$—N=N—, —N=N—O—, —N=CH—S— or —O—CH$_2$CH$_2$—O—;

$R_7$ is:

(i) when Z is nitrogen:
absent, and (ii) when Z is carbon:
hydrogen, $C_{1-4}$ alkyl, $C_{3-6}$ cycloalkyl, $C_{1-3}$ alkoxy, trifluoromethyl, fluoro, chloro, bromo, cyano, acetyl, amino, borono, nitro, carboxyl, $C_{1-4}$ alkoxycarbonyl, phenyl, phenoxy, phenoxycarbonyl, benzyloxy, hydroxyl, hydroxymethyl, —CHO, —CH=NOH, —C=NOHCH$_3$, —SO$_3$H, —SO$_2$CH$_3$, —SO$_2$NH$_2$, or when $R_7$ are located at the ortho position to another $R_i$, they together form -$Z_1$=$Z_2$-$Z_3$=$Z_4$- (wherein $Z_1$ through $Z_4$ each independently represents CH or N), —S—CO—O—, —CH=CH—NH—, —CH=CH—S—, —CH=CH—O—, —N=CH—NH—, —CH$_2$—N=N—, —N=N—O—, —N=CH—S— or —O—CH$_2$CH$_2$—O—;

$R_8$ through $R_9$ are each independently hydrogen, $C_{1-4}$ alkyl, $C_{3-6}$ cycloalkyl, $C_{1-3}$ alkoxy, trifluoromethyl, fluoro, chloro, bromo, cyano, acetyl, amino, borono, nitro, carboxyl, $C_{1-4}$ alkoxycarbonyl, phenyl, phenoxy, phenoxycarbonyl, benzyloxy, hydroxyl, hydroxymethyl, —CHO, —CH=NOH, —C=NOHCH$_3$, —SO$_3$H, —SO$_2$CH$_3$, —SO$_2$NH$_2$, or when any two $R_i$s are located at the ortho position to each other, they together form -$Z_1$=$Z_2$-$Z_3$=$Z_4$- (wherein $Z_1$ through $Z_4$ each independently represents CH or N), —S—CO—O—, —CH=CH—NH—, —CH=CH—S—, —CH=CH—O—, —N=CH—NH—, —CH$_2$—N=N—, —N=N—O—, —N=CH—S— or —O—CH$_2$CH$_2$—O—; and X, Y and Z are each independently carbon or nitrogen.

In one particular embodiment of the third embodiment, the present invention relates to compounds represented by formula A(III)

wherein $R_1$ through $R_9$ are each independently (i) when connected to a carbon atom:
hydrogen, $C_{1-6}$ alkyl, $C_{3-6}$ cycloalkyl, $C_{1-3}$ alkoxy, n-butoxy, i-butoxy, sec-butoxy, $R_{13}R_{14}N$— (wherein $R_{13}$ and $R_{14}$ are each independently hydrogen or $C_{1-3}$ alkyl), trifluoromethyl, trifluoromethoxy, difluoromethoxy, fluoro, chloro, bromo, cyano, acetyl, amino, borono, nitro, carboxyl, $C_{1-6}$ alkoxycarbonyl, phenyl, phenoxy, phenoxycarbonyl, benzyloxy, hydroxyl, trimethylsilyloxy, diphenyl-t-butylsilyloxy, hydroxymethyl, —CHO, —CH=NOH, —C=NOHCH$_3$, —SO$_3$H, —SO$_2$CH$_3$, —SO$_2$NHR$_{15}$ (wherein R$_{15}$ is hydrogen or $C_{1-3}$ alkyl), or —O(CH$_2$)$_n$OR$_{16}$— (wherein R$_{16}$ is hydrogen or $C_{1-3}$ alkyl, and n is 1, 2 or 3); or when any two R$_i$s are located at the ortho position to each other, they together form -Z$_1$=Z$_2$-Z$_3$=Z$_4$- (wherein Z$_1$ through Z$_4$ each independently represents CH or N), —S—CO—O—, —CH=CH—NH—, —CH=CH—S—, —CH=CH—O—, —N=CH—NH—, —CH$_2$—N=N—, —N=N—O—, —N=CH—S— or —O—CH$_2$CH$_2$—O—;
or (ii) when connected to a nitrogen atom:
absent;
and X, Y and Z are each independently carbon or nitrogen;
with the proviso that
when R$_1$=R$_3$=R$_4$=R$_5$=R$_6$=R$_7$=R$_8$=R$_9$=hydrogen, and X=Y=Z=carbon; R$_2$ is not NH$_2$, NO$_2$, or H.

In another embodiment of the third embodiment, the invention relates to compounds described by formula A(III) wherein R$_1$, R$_3$ and R$_4$ are each hydrogen;

R$_2$ is hydrogen, fluoro, chloro, bromo, cyano, acetyl, amino, nitro, carboxyl, $C_{1-4}$ alkoxycarbonyl, phenoxycarbonyl, hydroxyl, —CHO, —CH=NOH, —C=NOHCH$_3$, —SO$_3$H, —SO$_2$CH$_3$ and —SO$_2$NH$_2$;

R$_5$ is:
(i) when X is nitrogen:
absent, and
(ii) when X is carbon:
hydrogen, $C_{1-4}$ alkyl, $C_{3-6}$ cycloalkyl, $C_{1-3}$ alkoxy, trifluoromethyl, fluoro, chloro, bromo, cyano, acetyl, amino, borono, nitro, carboxyl, $C_{1-4}$ alkoxycarbonyl, phenyl, phenoxy, phenoxycarbonyl, benzyloxy, hydroxyl, hydroxymethyl, —CHO, —CH=NOH, —C=NOHCH$_3$, —SO$_3$H, —SO$_2$CH$_3$, —SO$_2$NH$_2$, or when R$_5$ are located at the ortho position to another R$_i$, they together form -Z$_1$=Z$_2$-Z$_3$=Z$_4$- (wherein Z$_1$ through Z$_4$ each independently represents CH or N), —S—CO—O—, —CH=CH—NH—, —CH=CH—S—, —CH=CH—O—, —N=CH—NH—, —CH$_2$—N=N—, —N=N—O—, —N=CH—S— or —O—CH$_2$CH$_2$—O—;

R$_6$ is:
(i) when Y is nitrogen:
absent, and
(ii) when Y is carbon:
hydrogen, $C_{1-4}$ alkyl, $C_{3-6}$ cycloalkyl, $C_{1-3}$ alkoxy, trifluoromethyl, fluoro, chloro, bromo, cyano, acetyl, amino, borono, nitro, carboxyl, $C_{1-4}$ alkoxycarbonyl, phenyl, phenoxy, phenoxycarbonyl, benzyloxy, hydroxyl, hydroxymethyl, —CHO, —CH=NOH, —C=NOHCH$_3$, —SO$_3$H, —SO$_2$CH$_3$, —SO$_2$NH$_2$, or when R$_6$ are located at the ortho position to another R$_i$, they together form -Z$_1$=Z$_2$-Z$_3$=Z$_4$- (wherein Z$_1$ through Z$_4$ each independently represents CH or N), —S—CO—O—, —CH=CH—NH—, —CH=CH—S—, —CH=CH—O—, —N=CH—NH—, —CH$_2$—N=N—, —N=N—O—, —N=CH—S— or —O—CH$_2$CH$_2$—O—;

R$_7$ is:
(i) when Z is nitrogen:
absent, and
(ii) when Z is carbon:
hydrogen, $C_{1-4}$ alkyl, $C_{3-6}$ cycloalkyl, $C_{1-3}$ alkoxy, trifluoromethyl, fluoro, chloro, bromo, cyano, acetyl, amino, borono, nitro, carboxyl, $C_{1-4}$ alkoxycarbonyl, phenyl, phenoxy, phenoxycarbonyl, benzyloxy, hydroxyl, hydroxymethyl, —CHO, —CH=NOH, —C=NOHCH$_3$, —SO$_3$H, —SO$_2$CH$_3$, —SO$_2$NH$_2$, or when R$_7$ are located at the ortho position to another R$_i$, they together form -Z$_1$=Z$_2$-Z$_3$=Z$_4$- (wherein Z$_1$ through Z$_4$ each independently represents CH or N), —S—CO—O—, —CH=CH—NH—, —CH=CH—S—, —CH=CH—O—, —N=CH—NH—, —CH$_2$—N=N—, —N=N—O—, —N=CH—S— or —O—CH$_2$CH$_2$—O—;

R$_8$ through R$_9$ are each independently hydrogen, $C_{1-4}$ alkyl, $C_{3-6}$ cycloalkyl, $C_{1-3}$ alkoxy, trifluoromethyl, fluoro, chloro, bromo, cyano, acetyl, amino, borono, nitro, carboxyl, $C_{1-4}$ alkoxycarbonyl, phenyl, phenoxy, phenoxycarbonyl, benzyloxy, hydroxyl, hydroxymethyl, —CHO, —CH=NOH, —C=NOHCH$_3$, —SO$_3$H, —SO$_2$CH$_3$, —SO$_2$NH$_2$, or when any two R$_i$s are located at the ortho position to each other, they together form -Z$_1$=Z$_2$-Z$_3$=Z$_4$- (wherein Z$_1$ through Z$_4$ each independently represents CH or N), —S—CO—O—, —CH=CH—NH—, —CH=CH—S—, —CH=CH—O—, —N=CH—NH—, —CH$_2$—N=N—, —N=N—O—, —N=CH—S— or —O—CH$_2$CH$_2$—O—; and X, Y and Z are each independently carbon or nitrogen;
with the proviso that
when R$_1$=R$_3$=R$_4$=R$_5$=R$_6$=R$_7$=R$_8$=R$_9$=hydrogen, and X=Y=Z=carbon;

R$_2$ is not NH$_2$, NO$_2$, or H.

Non-limiting specific compounds described by formula A(III) are listed in Table 3.

TABLE 3

Representative Compounds in Formula A(III):

| R$_1$ | R$_2$ | R$_3$ | R$_4$ | R$_5$ | R$_6$ | R$_7$ | R$_8$ | R$_9$ | X | Y | Z |
|---|---|---|---|---|---|---|---|---|---|---|---|
| H | H | H | H | H | H | H | H | H | C | C | C |
| H | NO$_2$ | H | H | H | H | H | H | H | C | C | C |
| H | NO$_2$ | H | H | Cl | H | H | H | Cl | C | C | C |
| H | NO$_2$ | H | H | H | NO$_2$ | H | H | H | C | C | C |
| H | NO$_2$ | H | H | H | Cl | H | H | H | C | C | C |
| H | NO$_2$ | H | H | H | B(OH)$_2$ | H | H | H | C | C | C |
| H | NO$_2$ | H | H | H | COCH3 | H | H | H | C | C | C |
| H | NO$_2$ | H | H | H | OH | H | H | H | C | C | C |
| H | NO$_2$ | H | H | H | COOH | H | H | H | C | C | C |
| H | H | H | H | H | Cl | H | H | H | C | C | C |
| H | NO$_2$ | H | H | —CH=CH—CH=CH— | | H | H | H | C | C | C |

TABLE 3-continued

Representative Compounds in Formula A(III):

| $R_1$ | $R_2$ | $R_3$ | $R_4$ | $R_5$ | $R_6$ | $R_7$ | $R_8$ | $R_9$ | X | Y | Z |
|---|---|---|---|---|---|---|---|---|---|---|---|
| H | $NH_2$ | H | H | H | $B(OH)_2$ | H | H | H | C | C | C |
| H | OH | H | H | H | $B(OH)_2$ | H | H | H | C | C | C |

In a particular preferred embodiment, the compound is

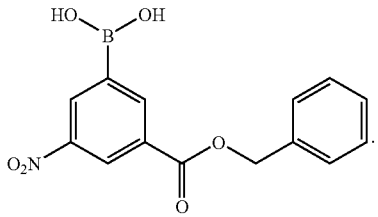

The compound

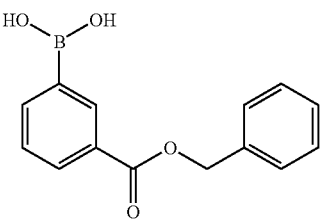

(compound F1001) is available from Combi-Blocks, Inc. (San Diego, Calif., Cat. No. BB-2118).

The compound

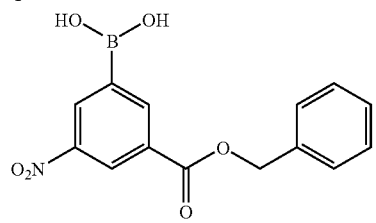

(compound F1201) is also available from Combi-Blocks, Inc. (San Diego, Calif., Cat. No. BB-2188).

Formula A(IV)

In a fourth embodiment, the compounds of the present invention are represented by formula A(IV):

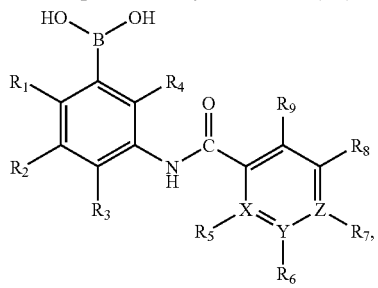

A(IV)

wherein $R_1$ through $R_9$ are each independently (i) when connected to a carbon atom:

hydrogen, $C_{1-6}$ alkyl, $C_{3-6}$ cycloalkyl, $C_{1-3}$ alkoxy, n-butoxy, i-butoxy, sec-butoxy, $R_{13}R_{14}N$— (wherein $R_{13}$ and $R_{14}$ are each independently hydrogen or $C_{1-3}$ alkyl), trifluoromethyl, trifluoromethoxy, difluoromethoxy, fluoro, chloro, bromo, cyano, acetyl, amino, borono, nitro, carboxyl, $C_{1-6}$ alkoxycarbonyl, phenyl, phenoxy, phenoxycarbonyl, benzyloxy, hydroxyl, trimethylsilyloxy, diphenyl-t-butylsilyloxy, hydroxymethyl, —CHO, —CH=NOH, —C=NOHCH$_3$, —SO$_3$H, —SO$_2$CH$_3$, —SO$_2$NHR$_{15}$ (wherein $R_{15}$ is hydrogen or $C_{1-3}$ alkyl), or —O(CH$_2$)$_n$OR$_{16}$— (wherein $R_{16}$ is hydrogen or $C_{1-3}$ alkyl, and n is 1, 2 or 3); or when any two $R_i$s are located at the ortho position to each other, they together form -$Z_1$=$Z_2$-$Z_3$=$Z_4$- (wherein $Z_1$ through $Z_4$ each independently represents CH or N), —S—CO—O—, —CH=CH—NH—, —CH=CH—S—, —CH=CH—O—, —N=CH—NH—, —CH$_2$—N=N—, —N=N—O—, —N=CH—S— or —O—CH$_2$CH$_2$—O—; or (ii) when connected to a nitrogen atom;

absent;

and

X, Y and Z are each independently carbon or nitrogen.

In a preferred embodiment of the fourth embodiment, $R_1$, $R_3$ and $R_4$ are each hydrogen;

$R_2$ is hydrogen, fluoro, chloro, bromo, cyano, acetyl, amino, nitro, carboxyl, $C_{1-4}$ alkoxycarbonyl, phenoxycarbonyl, hydroxyl, —CHO, —CH=NOH, —C=NOHCH$_3$, —SO$_3$H, —SO$_2$CH$_3$ and —SO$_2$NH$_2$;

$R_5$ is:

(i) when X is nitrogen:

absent, and (ii) when X is carbon:

hydrogen, $C_{1-4}$ alkyl, $C_{3-6}$ cycloalkyl, $C_{1-3}$ alkoxy, trifluoromethyl, fluoro, chloro, bromo, cyano, acetyl, amino, borono, nitro, carboxyl, $C_{1-4}$ alkoxycarbonyl, phenyl, phenoxy, phenoxycarbonyl, benzyloxy, hydroxyl, hydroxymethyl, —CHO, —CH=NOH, —C=NOHCH$_3$, —SO$_3$H, —SO$_2$CH$_3$, —SO$_2$NH$_2$, or when $R_5$ are located at the ortho position to another $R_i$, they together form -$Z_1$=$Z_2$-$Z_3$=$Z_4$- (wherein $Z_1$ through $Z_4$ each independently represents CH or N), —S—CO—O—, —CH=CH—NH—, —CH=CH—S—, —CH=CH—O—, —N=CH—NH—, —CH$_2$—N=N—, —N=N—O—, —N=CH—S— or —O—CH$_2$CH$_2$—O—;

$R_6$ is:

(i) when Y is nitrogen:

absent, and (ii) when Y is carbon:

hydrogen, $C_{1-4}$ alkyl, $C_{3-6}$ cycloalkyl, $C_{1-3}$ alkoxy, trifluoromethyl, fluoro, chloro, bromo, cyano, acetyl, amino, borono, nitro, carboxyl, $C_{1-4}$ alkoxycarbonyl, phenyl, phenoxy, phenoxycarbonyl, benzyloxy, hydroxyl, hydroxymethyl, —CHO, —CH=NOH, —C=NOHCH$_3$, —SO$_3$H, —SO$_2$CH$_3$, —SO$_2$NH$_2$, or when $R_6$ are located at the ortho position to another $R_i$, they together form -$Z_1$=$Z_2$-$Z_3$=$Z_4$- (wherein $Z_1$ through $Z_4$ each independently represents CH or N), —S—CO—O—, —CH=CH—NH—, —CH=CH—S—, —CH=CH—O—, —N=CH—NH—, —CH$_2$—N=N—, —N=N—O—, —N=CH—S— or —O—CH$_2$CH$_2$—O—;

$R_7$ is:

(i) when Z is nitrogen:

absent, and (ii) when Z is carbon:

hydrogen, $C_{1-4}$ alkyl, $C_{3-6}$ cycloalkyl, $C_{1-3}$ alkoxy, trifluoromethyl, fluoro, chloro, bromo, cyano, acetyl, amino, borono, nitro, carboxyl, $C_{1-4}$ alkoxycarbonyl, phenyl, phenoxy, phenoxycarbonyl, benzyloxy, hydroxyl, hydroxymethyl, —CHO, —CH=NOH, —C=NOHCH$_3$, —SO$_3$H, —SO$_2$CH$_3$, —SO$_2$NH$_2$, or when $R_7$ are located at the ortho position to another $R_i$, they together form -$Z_1$=$Z_2$-$Z_3$=$Z_4$- (wherein $Z_1$ through $Z_4$ each independently represents CH or N), —S—CO—O—, —CH=CH—NH—, —CH=CH—S—, —CH=CH—O—, —N=CH—NH—, —CH$_2$—N=N—, —N=N—O—, —N=CH—S— or —O—CH$_2$CH$_2$—O—;

$R_8$ through $R_9$ are each independently hydrogen, $C_{1-4}$ alkyl, $C_{3-6}$ cycloalkyl, $C_{1-3}$ alkoxy, trifluoromethyl, fluoro, chloro, bromo, cyano, acetyl, amino, borono, nitro, carboxyl, $C_{1-4}$ alkoxycarbonyl, phenyl, phenoxy, phenoxycarbonyl, benzyloxy, hydroxyl, hydroxymethyl, —CHO, —CH=NOH, —C=NOHCH$_3$, —SO$_3$H, —SO$_2$CH$_3$, —SO$_2$NH$_2$, or when any two $R_i$s are located at the ortho position to each other, they together form -$Z_1$=$Z_2$-$Z_3$=$Z_4$- (wherein $Z_1$ through $Z_4$ each independently represents CH or N), —S—CO—O—, —CH=CH—NH—, —CH=CH—S—, —CH=CH—O—, —N=CH—NH—, —CH$_2$—N=N—, —N=N—O—, —N=CH—S— or —O—CH$_2$CH$_2$—O—; and X, Y and Z are each independently carbon or nitrogen.

In one particular embodiment of the fourth embodiment, the compounds of the present invention are represented by formula A(IV)

wherein $R_1$ through $R_9$ are each independently (i) when connected to a carbon atom:

hydrogen, $C_{1-6}$ alkyl, $C_{3-6}$ cycloalkyl, $C_{1-3}$ alkoxy, n-butoxy, i-butoxy, sec-butoxy, $R_{13}R_{14}N$— (wherein $R_{13}$ and $R_{14}$ are each independently hydrogen or $C_{1-3}$ alkyl), trifluoromethyl, trifluoromethoxy, difluoromethoxy, fluoro, chloro, bromo, cyano, acetyl, amino, borono, nitro, carboxyl, $C_{1-6}$ alkoxycarbonyl, phenyl, phenoxy, phenoxycarbonyl, benzyloxy, hydroxyl, trimethylsilyloxy, diphenyl-t-butylsilyloxy, hydroxymethyl, —CHO, —CH=NOH, —C=NOHCH$_3$, —SO$_3$H, —SO$_2$CH$_3$, —SO$_2$NHR$_{15}$ (wherein $R_{15}$ is hydrogen or $C_{1-3}$ alkyl), or —O(CH$_2$)$_n$OR$_{16}$— (wherein $R_{16}$ is hydrogen or $C_{1-3}$ alkyl, and n is 1, 2 or 3); or when any two $R_i$s are located at the ortho position to each other, they together form -$Z_1$=$Z_2$-$Z_3$=$Z_4$- (wherein $Z_1$ through $Z_4$ each independently represents CH or N), —S—CO—O—, —CH=CH—NH—, —CH=CH—S—, —CH=CH—O—, —N=CH—NH—, —CH$_2$—N=N—, —N=N—O—, —N=CH—S— or —O—CH$_2$CH$_2$—O—; or (ii) when connected to a nitrogen atom;

absent;

and

X, Y and Z are each independently carbon or nitrogen;

with the proviso that when $R_1$=$R_2$=$R_3$=$R_4$=$R_5$=$R_6$=$R_8$=$R_9$=hydrogen, and X=Y=Z=carbon; $R_7$ is not Cl, CN, OCH$_3$, NO$_2$, CF$_3$, H, or COOCH$_3$;

when $R_1$=$R_2$=$R_3$=$R_4$=$R_5$=$R_7$=$R_8$=$R_9$=hydrogen, and X=Y=Z=carbon; $R_6$ is not CN, NO$_2$, or CF$_3$;

when $R_1$=$R_2$=$R_3$=$R_4$=$R_5$=$R_8$=$R_9$=hydrogen, and X=Y=Z=carbon; $R_6$ and $R_7$ together is not —CH=CH—CH=CH—;

when $R_1$=$R_2$=$R_3$=$R_4$=$R_6$=$R_7$=$R_8$=$R_9$=hydrogen, and X=Y=Z=carbon; $R_5$ is not OCOCH$_3$;

when $R_1$=$R_3$=$R_4$=$R_5$=$R_6$=$R_7$=$R_8$=$R_9$=hydrogen, and X=Y=Z=carbon; $R_2$ is not COOH; and when $R_1$=$R_2$=$R_3$=$R_4$=$R_5$=$R_8$=$R_9$=hydrogen, $R_6$=Cl, and X=Y=Z=carbon; $R_7$ is not Cl.

In a preferred embodiment of the fourth embodiment, the compounds of the present invention are represented by formula A(IV) wherein $R_1$, $R_3$ and $R_4$ are each hydrogen;

$R_2$ is hydrogen, fluoro, chloro, bromo, cyano, acetyl, amino, nitro, carboxyl, $C_{1-4}$ alkoxycarbonyl, phenoxycarbonyl, hydroxyl, —CHO, —CH=NOH, —C=NOHCH$_3$, —SO$_3$H, —SO$_2$CH$_3$ and —SO$_2$NH$_2$;

$R_5$ is:

(i) when X is nitrogen:

absent, and (ii) when X is carbon:

hydrogen, $C_{1-4}$ alkyl, $C_{3-6}$ cycloalkyl, $C_{1-3}$ alkoxy, trifluoromethyl, fluoro, chloro, bromo, cyano, acetyl, amino, borono, nitro, carboxyl, $C_{1-4}$ alkoxycarbonyl, phenyl, phenoxy, phenoxycarbonyl, benzyloxy, hydroxyl, hydroxymethyl, —CHO, —CH=NOH, —C=NOHCH$_3$, —SO$_3$H, —SO$_2$CH$_3$, —SO$_2$NH$_2$, or when $R_5$ are located at the ortho position to another $R_i$, they together form -$Z_1$=$Z_2$-$Z_3$=$Z_4$- (wherein $Z_1$ through $Z_4$ each independently represents CH or N), —S—CO—O—, —CH=CH—NH—, —CH=CH—S—, —CH=CH—O—, —N=CH—NH—, —CH$_2$—N=N—, —N=N—O—, —N=CH—S— or —O—CH$_2$CH$_2$—O—;

$R_6$ is:

(i) when Y is nitrogen:

absent, and (ii) when Y is carbon:

hydrogen, $C_{1-4}$ alkyl, $C_{3-6}$ cycloalkyl, $C_{1-3}$ alkoxy, trifluoromethyl, fluoro, chloro, bromo, cyano, acetyl, amino, borono, nitro, carboxyl, $C_{1-4}$ alkoxycarbonyl, phenyl, phenoxy, phenoxycarbonyl, benzyloxy, hydroxyl, hydroxymethyl, —CHO, —CH=NOH, —C=NOHCH$_3$, —SO$_3$H, —SO$_2$CH$_3$, —SO$_2$NH$_2$, or when $R_6$ are located at the ortho position to another $R_i$, they together form -$Z_1$=$Z_2$-$Z_3$=$Z_4$- (wherein $Z_1$ through $Z_4$ each independently represents CH or N), —S—CO—O—, —CH=CH—NH—, —CH=CH—S—, —CH=CH—O—, —N=CH—NH—, —CH$_2$—N=N—, —N=N—O—, —N=CH—S— or —O—CH$_2$CH$_2$—O—;

$R_7$ is:

(i) when Z is nitrogen:

absent, and (ii) when Z is carbon:

hydrogen, $C_{1-4}$ alkyl, $C_{3-6}$ cycloalkyl, $C_{1-3}$ alkoxy, trifluoromethyl, fluoro, chloro, bromo, cyano, acetyl, amino, borono, nitro, carboxyl, $C_{1-4}$ alkoxycarbonyl, phenyl, phenoxy, phenoxycarbonyl, benzyloxy, hydroxyl, hydroxymethyl, —CHO, —CH=NOH, —C=NOHCH$_3$, —SO$_3$H, —SO$_2$CH$_3$, —SO$_2$NH$_2$, or when $R_7$ are located at the ortho position to another $R_i$, they together form -$Z_1$=$Z_2$-$Z_3$=$Z_4$- (wherein $Z_1$ through $Z_4$ each independently represents CH or N), —S—CO—O—, —CH=CH—NH—, —CH=CH—S—, —CH=CH—O—, —N=CH—NH—, —CH$_2$—N=N—, —N=N—O—, —N=CH—S— or —O—CH$_2$CH$_2$—O—;

$R_8$ through $R_9$ are each independently hydrogen, $C_{1-4}$ alkyl, $C_{3-6}$ cycloalkyl, $C_{1-3}$ alkoxy, trifluoromethyl, fluoro, chloro, bromo, cyano, acetyl, amino, borono, nitro, carboxyl, $C_{1-4}$ alkoxycarbonyl, phenyl, phenoxy, phenoxycarbonyl, benzyloxy, hydroxyl, hydroxymethyl, —CHO, —CH=NOH, —C=NOHCH$_3$, —SO$_3$H, —SO$_2$CH$_3$, —SO$_2$NH$_2$, or when any two $R_i$s are located at the ortho position to each other, they together form -$Z_1$=$Z_2$-$Z_3$=$Z_4$- (wherein $Z_1$ through $Z_4$ each independently represents CH or N), —S—CO—O—, —CH=CH—NH—, —CH=CH—S—, —CH=CH—O—, —N=CH—NH—, —CH$_2$—N=N—, —N=N—O—, —N=CH—S— or —O—CH$_2$CH$_2$—O—; and X, Y and Z are each independently carbon or nitrogen;
with the proviso that
when $R_1$=$R_2$=$R_3$=$R_4$=$R_5$=$R_6$=$R_8$=$R_9$=hydrogen, and X=Y=Z=carbon; $R_7$ is not Cl, CN, OCH$_3$, NO$_2$, CF$_3$, H, or COOCH$_3$;
when $R_1$=$R_2$=$R_3$=$R_4$=$R_5$=$R_7$=$R_8$=$R_9$=hydrogen, and X=Y=Z=carbon; $R_6$ is not CN, NO$_2$, or CF$_3$;
when $R_1$=$R_2$=$R_3$=$R_4$=$R_5$=$R_8$=$R_9$=hydrogen, and X=Y=Z=carbon; $R_6$ and $R_7$ together is not —CH=CH—CH=CH—;
when $R_1$=$R_2$=$R_3$=$R_4$=$R_6$=$R_7$=$R_8$=$R_9$=hydrogen, and X=Y=Z=carbon; $R_5$ is not OCOCH$_3$;
when $R_1$=$R_3$=$R_4$=$R_5$=$R_6$=$R_7$=$R_8$=$R_9$=hydrogen, and X=Y=Z=carbon; $R_2$ is not COOH; and
when $R_1$=$R_2$=$R_3$=$R_4$=$R_5$=$R_8$=$R_9$=hydrogen, $R_6$=Cl, and X=Y=Z=carbon; $R_7$ is not Cl.

TABLE 4

Representative Compounds in Formula A(IV):

| $R_1$ | $R_2$ | $R_3$ | $R_4$ | $R_5$ | $R_6$ | $R_7$ | $R_8$ | $R_9$ | X | Y | Z |
|---|---|---|---|---|---|---|---|---|---|---|---|
| H | COOH | H | H | F | H | H | H | H | C | C | C |
| H | COOH | H | H | Cl | H | H | H | Cl | C | C | C |
| H | NO$_2$ | H | H | Cl | H | H | H | Cl | C | C | C |
| H | H | H | H | Cl | H | H | H | Cl | C | C | C |

Formula A(V)

In a fifth embodiment, the compounds of the present invention are represented by formula A(V):

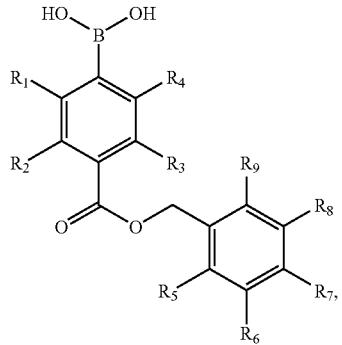

A(V)

wherein $R_1$ through $R_9$ are each independently hydrogen, $C_{1-6}$ alkyl, $C_{3-6}$ cycloalkyl, $C_{1-3}$ alkoxy, n-butoxy, i-butoxy, sec-butoxy, $R_{13}R_{14}N$— (wherein $R_{13}$ and $R_{14}$ each independently represents hydrogen or $C_{1-3}$ alkyl), trifluoromethyl, trifluoromethoxy, difluoromethoxy, fluoro, chloro, bromo, cyano, acetyl, nitro, amino, borono, carboxyl, $C_{1-6}$ alkoxycarbonyl, phenyl, phenoxy, phenoxycarbonyl, benzyloxy, hydroxyl, trimethylsilyloxy, diphenyl-t-butylsilyloxy, hydroxymethyl, —SO$_3$H, —SO$_2$CH$_3$, —SO$_2$NHR$_{15}$ (wherein $R_{15}$ is hydrogen or $C_{1-3}$ alkyl), or —O(CH$_2$)$_n$OR$_{16}$— (wherein $R_{16}$ is hydrogen or $C_{1-3}$ alkyl, and n is 1, 2 or 3); or when any two $R_i$s are located at the ortho position to each other, they together form -$Z_1$=$Z_2$-$Z_3$=$Z_4$- (wherein $Z_1$ through $Z_4$ each independently represents CH or N), —S—CO—O—, —CH=CH—NH—, —CH=CH—S—, —CH=CH—O—, —N=CH—NH—, —CH$_2$—N=N—, —N=N—O—, —N=CH—S— or —O—CH$_2$CH$_2$—O—.

In a preferred embodiment of the fifth embodiment,
$R_1$ and $R_4$ are each hydrogen;
$R_2$ and $R_3$ are each independently hydrogen, fluoro, chloro, bromo, cyano, acetyl, amino, borono, nitro, carboxyl, $C_{1-4}$ alkoxycarbonyl, phenoxycarbonyl, hydroxyl, —SO$_3$H, —SO$_2$CH$_3$ and —SO$_2$NH$_2$;
$R_5$ through $R_9$ are each independently hydrogen, $C_{1-4}$ alkyl, $C_{3-6}$ cycloalkyl, $C_{1-3}$ alkoxy, trifluoromethyl, fluoro, chloro, bromo, cyano, acetyl, amino, borono, nitro, carboxyl, $C_{1-4}$ alkoxycarbonyl, phenyl, phenoxy, phenoxycarbonyl, benzyloxy, hydroxyl, hydroxymethyl, —SO$_3$H, —SO$_2$CH$_3$, —SO$_2$NH$_2$, or when any two $R_i$s are located at the ortho position to each other, they together form -$Z_1$=$Z_2$-$Z_3$=$Z_4$- (wherein $Z_1$ through $Z_4$ each independently represents CH or N), —S—CO—O—, —CH=CH—NH—, —CH=CH—S—, —CH=CH—O—, —N=CH—NH—, —CH$_2$—N=N—, —N=N—O—, —N=CH—S— or —O—CH$_2$CH$_2$—O—.

In one particular embodiment of the fifth embodiment, the compounds of the present invention are represented by formula A(V):
wherein $R_1$ through $R_9$ are each independently hydrogen, $C_{1-6}$ alkyl, $C_{3-6}$ cycloalkyl, $C_{1-3}$ alkoxy, n-butoxy, i-butoxy, sec-butoxy, $R_{13}R_{14}N$— (wherein $R_{13}$ and $R_{14}$ each independently represents hydrogen or $C_{1-3}$ alkyl), trifluoromethyl, trifluoromethoxy, difluoromethoxy, fluoro, chloro, bromo, cyano, acetyl, nitro, amino, borono, carboxyl, $C_{1-6}$ alkoxycarbonyl, phenyl, phenoxy, phenoxycarbonyl, benzyloxy, hydroxyl, trimethylsilyloxy, diphenyl-t-butylsilyloxy, hydroxymethyl, —SO$_3$H, —SO$_2$CH$_3$, —SO$_2$NHR$_{15}$ (wherein $R_{15}$ is hydrogen or $C_{1-3}$ alkyl), or —O(CH$_2$)$_n$OR$_{16}$— (wherein $R_{16}$ is hydrogen or $C_{1-3}$ alkyl, and n is 1, 2 or 3); or when any two $R_i$ s are located at the ortho position to each other, they together form -$Z_1$=$Z_2$-$Z_3$=$Z_4$- (wherein $Z_1$ through $Z_4$ each independently represents CH or N), —S—CO—O—, —CH=CH—NH—, —CH=CH—S—, —CH=CH—O—, —N=CH—NH—, —CH$_2$—N=N—, —N=N—O—, —N=CH—S— or —O—CH$_2$CH$_2$—O—;
with the proviso that
when $R_1$=$R_2$=$R_3$=$R_4$=$R_5$=$R_6$=$R_8$=$R_9$=hydrogen; $R_7$ is not H, OH or C(CH$_3$)$_3$.

In another embodiment of the fifth embodiment,
$R_1$ and $R_4$ are each hydrogen;
$R_2$ and $R_3$ are each independently hydrogen, fluoro, chloro, bromo, cyano, acetyl, amino, borono, nitro, carboxyl, $C_{1-4}$ alkoxycarbonyl, phenoxycarbonyl, hydroxyl, —SO$_3$H, —SO$_2$CH$_3$ and —SO$_2$NH$_2$;
$R_5$ through $R_9$ are each independently hydrogen, $C_{1-4}$ alkyl, $C_{3-6}$ cycloalkyl, $C_{1-3}$ alkoxy, trifluoromethyl, fluoro, chloro, bromo, cyano, acetyl, amino, borono, nitro, carboxyl, $C_{1-4}$ alkoxycarbonyl, phenyl, phenoxy, phenoxycarbonyl, benzyloxy, hydroxyl, hydroxymethyl, —SO$_3$H, —SO$_2$CH$_3$, —SO$_2$NH$_2$, or when any two $R_i$s are located at the ortho position to each other, they together form -$Z_1$=$Z_2$-$Z_3$=$Z_4$- (wherein $Z_1$ through $Z_4$ each independently represents CH or N), —S—CO—O—, —CH=CH—NH—, —CH=CH—S—, —CH=CH—O—, —N=CH—NH—, —CH$_2$—N=N—, —N=N—O—, —N=CH—S— or —O—CH$_2$CH$_2$—O—;
with the proviso that
when $R_1$=$R_2$=$R_3$=$R_4$=$R_5$=$R_6$=$R_8$=$R_9$=hydrogen; $R_7$ is not H, OH or C(CH$_3$)$_3$.

Non-limiting specific compounds described by formula A(V) are listed in Table 5.

TABLE 5

Representative Compounds in Formula A(V):

| $R_1$ | $R_2$ | $R_3$ | $R_4$ | $R_5$ | $R_6$ | $R_7$ | $R_8$ | $R_9$ |
|---|---|---|---|---|---|---|---|---|
| H | H | H | H | H | H | H | H | H |
| H | F | H | H | H | $NO_2$ | H | H | H |
| H | F | H | H | H | Cl | H | H | H |
| H | H | H | H | H | Cl | H | H | H |
| H | H | H | H | H | $NO_2$ | H | H | H |

Compound

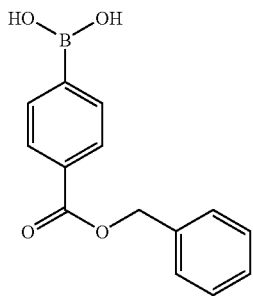

(compound F1002) is available from Combi-Blocks, Inc. (San Diego, Calif., Cat. No. BB-2114).

Formula A(VI)

In a sixth embodiment, the compounds of the present invention are represented by formula A(VI):

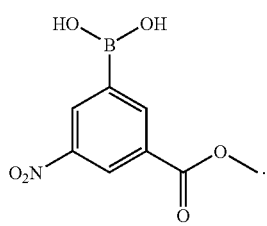

(Compound F1212)

A(VI)

This compound is available from Combi-Blocks, Inc. (San Diego, Calif., Cat. No. BB-2162).

Formula A(VII)

In a seventh embodiment, the compounds of the present invention are represented by formula A(VII):

A(VII)

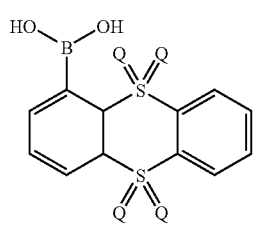

wherein Q is oxygen or lone-pair electrons.

The compound

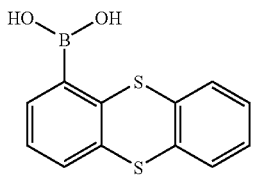

(compound F1012) is available from Sigma-Aldrich, Inc. (St. Louis, Mo., Cat. No. 51221-4.

Formula A(VIII)

In an eighth embodiment, the compounds of the present invention are represented by formula A(VIII):

(compound BB-1003)

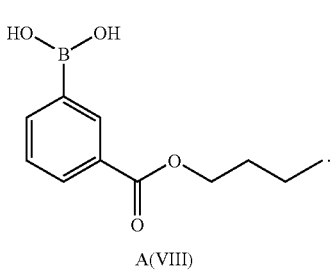

A(VIII)

Compound BB-1003 is commercially available from Combi-Blocks, Inc. (San Diego, Calif., Cat. No. BB2119).

Formula A(IX)

In a ninth embodiment, the compounds of the present invention are represented by formula A(IX):

(compound BB-1004)

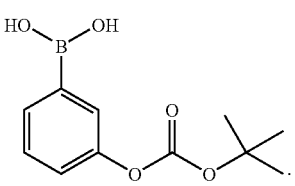

A(IX)

Compound BB-1004 is commercially available from Combi-Blocks, Inc. (San Diego, Calif., Cat. No. BB2623).

Formula A(X)

In a tenth embodiment, the compounds of the present invention are represented by formula A(X):

(compound BB-1005)

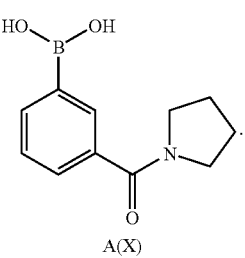

A(X)

Compound BB-1005 is commercially available from Combi-Blocks, Inc. (San Diego, Calif., Cat. No. BB3052).

Formula A(XI)

In an eleventh embodiment, the compounds of the present invention are represented by formula A(XI):

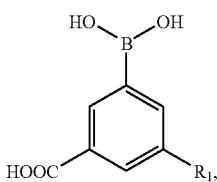

A(XI)

wherein $R_1$ is hydrogen, $C_{1-6}$ alkyl, $C_{3-6}$ cycloalkyl, $C_{1-3}$ alkoxy, n-butoxy, i-butoxy, sec-butoxy, $R_{13}R_{14}N$— (wherein $R_{13}$ and $R_{14}$ are each independently hydrogen or $C_{1-3}$ alkyl), trifluoromethyl, trifluoromethoxy, difluoromethoxy, fluoro, chloro, bromo, cyano, acetyl, amino, borono, nitro, carboxyl, $C_{1-6}$ alkoxycarbonyl, phenyl, phenoxy, phenoxycarbonyl, benzyloxy, hydroxyl, trimethylsilyloxy, diphenyl-t-butylsilyloxy, hydroxymethyl, —SO$_3$H, —SO$_2$CH$_3$, —SO$_2$NHR$_{15}$ (wherein $R_{15}$ is hydrogen or $C_{1-3}$ alkyl), or —O(CH$_2$)$_n$OR$_{16}$— (wherein $R_{16}$ is hydrogen or $C_{1-3}$ alkyl, and n is 1, 2 or 3).

In a preferred embodiment of the eleventh embodiment, $R_1$ is hydrogen, fluoro, chloro, bromo, cyano, acetyl, amino, borono, nitro, carboxyl, $C_{1-4}$ alkoxycarbonyl, phenoxycarbonyl, hydroxyl, —SO$_3$H, —SO$_2$CH$_3$ and —SO$_2$NH$_2$.

In one particular embodiment of the eleventh embodiment, the compounds of the present invention are represented by formula A(XI), wherein $R_1$ is $C_1$alkyl, $C_{3-6}$ cycloalkyl, $C_{1-3}$ alkoxy, n-butoxy, i-butoxy, sec-butoxy, $R_{13}R_{14}N$— (wherein $R_{13}$ and $R_{14}$ are each independently hydrogen or $C_{1-3}$ alkyl), trifluoromethyl, trifluoromethoxy, difluoromethoxy, fluoro, chloro, bromo, cyano, acetyl, carboxyl, $C_{1-6}$ alkoxycarbonyl, phenyl, phenoxy, phenoxycarbonyl, benzyloxy, hydroxyl, trimethylsilyloxy, diphenyl-t-butylsilyloxy, hydroxymethyl, —SO$_3$H, —SO$_2$CH$_3$, —SO$_2$NHR$_{15}$ (wherein $R_{15}$ is hydrogen or $C_{1-3}$ alkyl), or —O(CH$_2$)$_n$OR$_{16}$— (wherein $R_{16}$ is hydrogen or $C_{1-3}$ alkyl, and n is 1, 2 or 3).

In another embodiment of the eleventh embodiment, $R_1$ is fluoro, chloro, bromo, cyano, acetyl, carboxyl, $C_{1-4}$ alkoxycarbonyl, phenoxycarbonyl, hydroxyl, —SO$_3$H, —SO$_2$CH$_3$ and —SO$_2$NH$_2$.

Non-limiting specific compounds described by formula A(XI) are listed in Table 6.

TABLE 6

| Representative Compounds in Formula A(XI): |
| --- |
| $R_1$ |
| NH$_2$ |
| H |
| OH |
| CN |
| Br |

Formula A(XII)

In a twelfth embodiment, the compounds of the present invention are represented by formula A(XII):

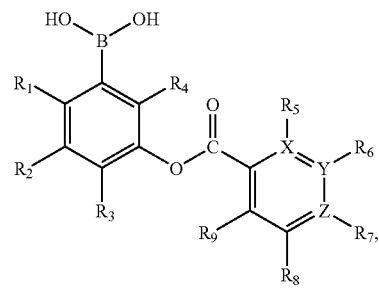

A(XII)

wherein $R_1$ through $R_9$ are each independently
(i) when connected to a carbon atom:
hydrogen, $C_{1-6}$ alkyl, $C_{3-6}$ cycloalkyl, $C_{1-3}$ alkoxy, n-butoxy, i-butoxy, sec-butoxy, $R_{13}R_{14}N$— (wherein $R_{13}$ and $R_{14}$ are each independently hydrogen or $C_{1-3}$ alkyl), trifluoromethyl, trifluoromethoxy, difluoromethoxy, fluoro, chloro, bromo, cyano, acetyl, amino, borono, nitro, carboxyl, $C_{1-6}$ alkoxycarbonyl, phenyl, phenoxy, phenoxycarbonyl, benzyloxy, hydroxyl, trimethylsilyloxy, diphenyl-t-butylsilyloxy, hydroxymethyl, —CHO, —CH=NOH, —C=NOHCH$_3$, —SO$_3$H, —SO$_2$CH$_3$, —SO$_2$NHR$_{15}$ (wherein $R_{15}$ is hydrogen or $C_{1-3}$ alkyl), or —O(CH$_2$)$_n$OR$_{16}$— (wherein $R_{16}$ is hydrogen or $C_{1-3}$ alkyl, and n is 1, 2 or 3); or when any two $R_i$s are located at the ortho position to each other, they together form -$Z_1$=$Z_2$-$Z_3$=$Z_4$- (wherein $Z_1$ through $Z_4$ each independently represents CH or N), —S—CO—O—, —CH=CH—NH—, —CH=CH—S—, —CH=CH—O—, —N=CH—NH—, —CH$_2$—N=N—, —N=N—O—, —N=CH—S— or —O—CH$_2$CH$_2$—O—; or
(ii) when connected to a nitrogen atom;
absent;
and
X, Y and Z are each independently carbon or nitrogen.

In a preferred embodiment of the twelfth embodiment, $R_1$, $R_3$ and $R_4$ are each hydrogen;
$R_2$ is hydrogen, fluoro, chloro, bromo, cyano, acetyl, amino, nitro, carboxyl, $C_{1-4}$ alkoxycarbonyl, phenoxycarbonyl, hydroxyl, —CHO, —CH=NOH, —C=NOHCH$_3$, —SO$_3$H, —SO$_2$CH$_3$ and —SO$_2$NH$_2$;
$R_5$ is:
(i) when X is nitrogen:
absent, and
(ii) when X is carbon:
hydrogen, $C_{1-4}$ alkyl, $C_{3-6}$ cycloalkyl, $C_{1-3}$ alkoxy, trifluoromethyl, fluoro, chloro, bromo, cyano, acetyl, amino, borono, nitro, carboxyl, $C_{1-4}$ alkoxycarbonyl, phenyl, phenoxy, phenoxycarbonyl, benzyloxy, hydroxyl, hydroxymethyl, —SO$_3$H, —SO$_2$CH$_3$, —SO$_2$NH$_2$, or when $R_5$ are located at the ortho position to another $R_i$, they together form -$Z_1$=$Z_2$-$Z_3$=$Z_4$- (wherein $Z_1$ through $Z_4$ each independently represents CH or N), —S—CO—O—, —CH=CH—NH—, —CH=CH—S—, —CH=CH—O—, —N=CH—NH—, —CH$_2$—N=N—, —N=N—O—, —N=CH—S— or —O—CH$_2$CH$_2$—O—;
$R_6$ is:
(i) when Y is nitrogen:
absent, and (ii) when Y is carbon:

hydrogen, $C_{1-4}$ alkyl, $C_{3-6}$ cycloalkyl, $C_{1-3}$ alkoxy, trifluoromethyl, fluoro, chloro, bromo, cyano, acetyl, amino, borono, nitro, carboxyl, $C_{1-4}$ alkoxycarbonyl, phenyl, phenoxy, phenoxycarbonyl, benzyloxy, hydroxyl, hydroxymethyl, —CHO, —CH=NOH, —C=NOHCH$_3$, —SO$_3$H, —SO$_2$CH$_3$, —SO$_2$NH$_2$, or when $R_6$ are located at the ortho position to another $R_j$, they together form -$Z_1$=$Z_2$-$Z_3$=$Z_4$- (wherein $Z_1$ through $Z_4$ each independently represents CH or N), —S—CO—O—, —CH=CH—NH—, —CH=CH—S—, —CH=CH—O—, —N=CH—NH—, —CH$_2$—N=N—, —N=N—O—, —N=CH—S— or —O—CH$_2$CH$_2$—O—;

$R_7$ is:

(i) when Z is nitrogen:

absent, and (ii) when Z is carbon:

hydrogen, $C_{1-4}$ alkyl, $C_{3-6}$ cycloalkyl, $C_{1-3}$ alkoxy, trifluoromethyl, fluoro, chloro, bromo, cyano, acetyl, amino, borono, nitro, carboxyl, $C_{1-4}$ alkoxycarbonyl, phenyl, phenoxy, phenoxycarbonyl, benzyloxy, hydroxyl, hydroxymethyl, —CHO, —CH=NOH, —C=NOHCH$_3$, —SO$_3$H, —SO$_2$CH$_3$, —SO$_2$NH$_2$, or when $R_7$ are located at the ortho position to another $R_j$, they together form -$Z_1$=$Z_2$-$Z_3$=$Z_4$- (wherein $Z_1$ through $Z_4$ each independently represents CH or N), —S—CO—O—, —CH=CH—NH—, —CH=CH—S—, —CH=CH—O—, —N=CH—NH—, —CH$_2$—N=N—, —N=N—O—, —N=CH—S— or —O—CH$_2$CH$_2$—O—;

$R_8$ through $R_9$ are each independently hydrogen, $C_{1-4}$ alkyl, $C_{3-6}$ cycloalkyl, $C_{1-3}$ alkoxy, trifluoromethyl, fluoro, chloro, bromo, cyano, acetyl, amino, borono, nitro, carboxyl, $C_{1-4}$ alkoxycarbonyl, phenyl, phenoxy, phenoxycarbonyl, benzyloxy, hydroxyl, hydroxymethyl, —CHO, —CH=NOH, —C=NOHCH$_3$, —SO$_3$H, —SO$_2$CH$_3$, —SO$_2$NH$_2$, or when any two $R_j$s are located at the ortho position to each other, they together form -$Z_1$=$Z_2$-$Z_3$=$Z_4$- (wherein $Z_1$ through $Z_4$ each independently represents CH or N), —S—CO—O—, —CH=CH—NH—, —CH=CH—S—, —CH=CH—O—, —N=CH—NH—, —CH$_2$—N=N—, —N=N—O—, —N=CH—S— or —O—CH$_2$CH$_2$—O—; and X, Y and Z are each independently carbon or nitrogen.

Non-limiting specific compounds described by formula A(XII) are listed in Table 7.

TABLE 7

Representative Compounds in Formula A(XII):

| $R_1$ | $R_2$ | $R_3$ | $R_4$ | $R_5$ | $R_6$ | $R_7$ | $R_8$ | $R_9$ | X | Y | Z |
|---|---|---|---|---|---|---|---|---|---|---|---|
| H | H | H | H | Cl | H | H | H | Cl | C | C | C |
| H | H | H | H | Cl | H | Cl | H | Cl | C | C | C |
| H | H | H | H | H | H | H | H | H | C | N | C |
| H | NO$_2$ | H | H | Cl | H | H | H | Cl | C | C | C |

Formula A(XIII)

In a thirteenth embodiment, the compounds of the present invention are represented by formula A(XIII):

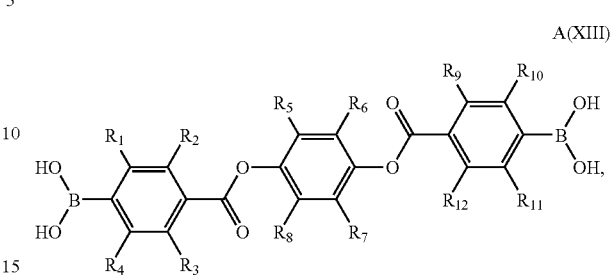

A(XIII)

wherein $R_1$ through $R_{12}$ are each independently hydrogen, $C_{1-6}$ alkyl, $C_{3-6}$ cycloalkyl, $C_{1-3}$ alkoxy, n-butoxy, i-butoxy, sec-butoxy, $R_{13}R_{14}N$— (wherein $R_{13}$ and $R_{14}$ are each independently hydrogen or $C_{1-3}$ alkyl), trifluoromethyl, trifluoromethoxy, difluoromethoxy, fluoro, chloro, bromo, cyano, acetyl, amino, borono, nitro, carboxyl, $C_{1-6}$ alkoxycarbonyl, phenyl, phenoxy, phenoxycarbonyl, benzyloxy, hydroxyl, trimethylsilyloxy, diphenyl-t-butylsilyloxy, hydroxymethyl, —SO$_3$H, —SO$_2$CH$_3$, —SO$_2$NHR$_{15}$ (wherein $R_{15}$ is hydrogen or $C_{1-3}$ alkyl), or —O(CH$_2$)$_n$OR$_{16}$— (wherein $R_{16}$ is hydrogen or $C_{1-3}$ alkyl, and n is 1, 2 or 3); or when any two $R_j$s are located at the ortho position to each other, they together form -$Z_1$=$Z_2$-$Z_3$=$Z_4$- (wherein $Z_1$ through $Z_4$ each independently represents CH or N), —S—CO—O—, —CH=CH—NH—, —CH=CH—S—, —CH=CH—O—, —N=CH—NH—, —CH$_2$—N=N—, —N=N—O—, —N=CH—S— or —O—CH$_2$CH$_2$—O—.

In a preferred embodiment of the thirteenth embodiment, $R_1$, $R_3$, $R_4$, $R_9$, $R_{11}$ and $R_{12}$ are each hydrogen;

$R_2$ and $R_{10}$ are each independently hydrogen, fluoro, chloro, bromo, cyano, acetyl, nitro, amino, borono, carboxyl, $C_{1-4}$ alkoxycarbonyl, phenoxycarbonyl, hydroxyl, —SO$_3$H, —SO$_2$CH$_3$ and —SO$_2$NH$_2$;

$R_5$ through $R_8$ are each independently hydrogen, $C_{1-4}$ alkyl, $C_{3-6}$ cycloalkyl, $C_{1-3}$ alkoxy, trifluoromethyl, fluoro, chloro, bromo, cyano, acetyl, amino, borono, nitro, carboxyl, $C_{1-4}$ alkoxycarbonyl, phenyl, phenoxy, phenoxycarbonyl, benzyloxy, hydroxyl, hydroxymethyl, —SO$_3$H, —SO$_2$CH$_3$, —SO$_2$NH$_2$, or when any two $R_j$s are located at the ortho position to each other, they together form -$Z_1$=$Z_2$-$Z_3$=$Z_4$- (wherein $Z_1$ through $Z_4$ each independently represents CH or N), —S—CO—O—, —CH=CH—NH—, —CH=CH—S—, —CH=CH—O—, —N=CH—NH—, —CH$_2$—N=N—, —N=N—O—, —N=CH—S— or —O—CH$_2$CH$_2$—O—.

Non-limiting specific compounds described by formula A(XIII) are listed in Table 8.

TABLE 8

Representative Compounds in Formula A(XIII):

| $R_1$ | $R_2$ | $R_3$ | $R_4$ | $R_5$ | $R_6$ | $R_7$ | $R_8$ | $R_9$ | $R_{10}$ | $R_{11}$ | $R_{12}$ |
|---|---|---|---|---|---|---|---|---|---|---|---|
| H | F | H | H | Cl | H | H | H | F | H | H | H |
| H | F | H | H | H | H | H | H | F | H | H | H |
| H | H | H | H | Cl | H | H | H | H | H | H | H |
| H | H | H | H | H | H | H | H | H | H | H | H |

Formula A(XIV)

In a fourteenth embodiment, the compounds of the present invention are represented by formula A(XIV):

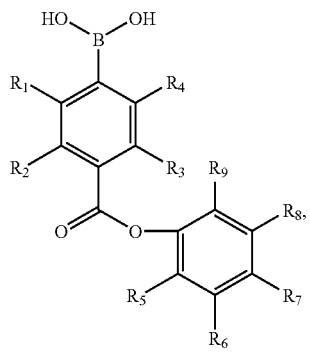

A(XIV)

wherein $R_1$ through $R_9$ are each independently hydrogen, $C_{1-6}$ alkyl, $C_{3-6}$ cycloalkyl, $C_{1-3}$ alkoxy, n-butoxy, i-butoxy, sec-butoxy, $R_{13}R_{14}N$— (wherein $R_{13}$ and $R_{14}$ each independently represents hydrogen or $C_{1-3}$ alkyl), trifluoromethyl, trifluoromethoxy, difluoromethoxy, fluoro, chloro, bromo, cyano, acetyl, nitro, amino, borono, carboxyl, $C_{1-6}$ alkoxycarbonyl, phenyl, phenoxy, phenoxycarbonyl, benzyloxy, hydroxyl, trimethylsilyloxy, diphenyl-t-butylsilyloxy, hydroxymethyl, —$SO_3H$, —$SO_2CH_3$, —$SO_2NHR_{15}$ (wherein $R_{15}$ is hydrogen or $C_{1-3}$ alkyl), or —$O(CH_2)_n$ $OR_{16}$— (wherein $R_{16}$ is hydrogen or $C_{1-3}$ alkyl, and n is 1, 2 or 3); or when any two $R_i$s are located at the ortho position to each other, they together form -$Z_1$=$Z_2$-$Z_3$=$Z_4$- (wherein $Z_1$ through $Z_4$ each independently represents CH or N), —S—CO—O—, —CH=CH—NH—, —CH=CH—S—, —CH=CH—O—, —N=CH—NH—, —CH_2—N=N—, —N=N—O—, —N=CH—S— or —O—CH_2CH_2—O—.

In a preferred embodiment of the fourteenth embodiment, $R_1$ and $R_4$ are each hydrogen;

$R_2$ and $R_3$ are each independently hydrogen, fluoro, chloro, bromo, cyano, acetyl, amino, borono, nitro, carboxyl, $C_{1-4}$ alkoxycarbonyl, phenoxycarbonyl, hydroxyl, —$SO_3H$, —$SO_2CH_3$ and —$SO_2NH_2$;

$R_5$ through $R_9$ are each independently hydrogen, $C_{1-4}$ alkyl, $C_{3-6}$ cycloalkyl, $C_{1-3}$ alkoxy, trifluoromethyl, fluoro, chloro, bromo, cyano, acetyl, amino, borono, nitro, carboxyl, $C_{1-4}$ alkoxycarbonyl, phenyl, phenoxy, phenoxycarbonyl, benzyloxy, hydroxyl, hydroxymethyl, —$SO_3H$, —$SO_2CH_3$, —$SO_2NH_2$, or when any two $R_i$s are located at the ortho position to each other, they together form -$Z_1$=$Z_2$-$Z_3$=$Z_4$- (wherein $Z_1$ through $Z_4$ each independently represents CH or N), —S—CO—O—, —CH=CH—NH—, —CH=CH—S—, —CH=CH—O—, —N=CH—NH—, —CH_2—N=N—, —N=N—O—, —N=CH—S— or —O—CH_2CH_2—O—.

Non-limiting specific compounds described by formula A(XIV) are listed in Table 9.

TABLE 9

Representative Compounds in Formula A(XIV):

| $R_1$ | $R_2$ | $R_3$ | $R_4$ | $R_5$ | $R_6$ | $R_7$ | $R_8$ | $R_9$ | $R_{10}$ | $R_{11}$ | $R_{12}$ |
|---|---|---|---|---|---|---|---|---|---|---|---|
| H | F | H | H | Cl | H | H | H | $NO_2$ | H | H | H |
| H | F | H | H | Cl | H | H | H | Cl | H | H | H |
| H | H | H | H | Cl | H | H | H | Cl | H | H | H |

Formula A(XV)

In a fifteenth embodiment, the compounds of the present invention are represented by formula A(XV):

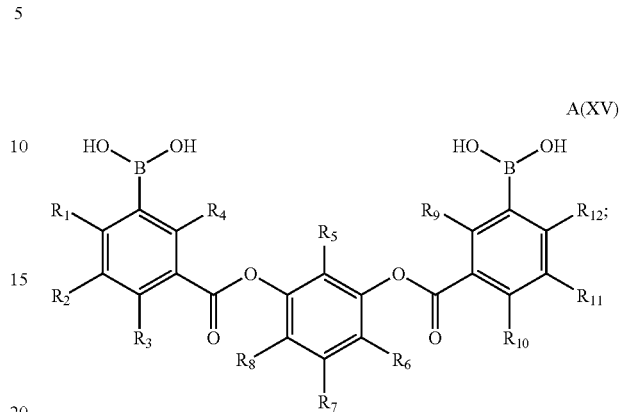

A(XV)

wherein $R_1$ through $R_{12}$ are each independently hydrogen, $C_{1-6}$ alkyl, $C_{3-6}$ cycloalkyl, $C_{1-3}$ alkoxy, n-butoxy, i-butoxy, sec-butoxy, $R_{13}R_{14}N$— (wherein $R_{13}$ and $R_{14}$ are each independently hydrogen or $C_{1-3}$ alkyl), trifluoromethyl, trifluoromethoxy, difluoromethoxy, fluoro, chloro, bromo, cyano, acetyl, amino, borono, nitro, carboxyl, $C_{1-6}$ alkoxycarbonyl, phenyl, phenoxy, phenoxycarbonyl, benzyloxy, hydroxyl, trimethylsilyloxy, diphenyl-t-butylsilyloxy, hydroxymethyl, —$SO_3H$, —$SO_2CH_3$, —$SO_2NHR_{15}$ (wherein $R_{15}$ is hydrogen or $C_{1-3}$ alkyl), or —$O(CH_2)_n$ $OR_{16}$— (wherein $R_{16}$ is hydrogen or $C_{1-3}$ alkyl, and n is 1, 2 or 3); or when any two $R_i$s are located at the ortho position to each other, they together form -$Z_1$=$Z_2$-$Z_3$=$Z_4$- (wherein $Z_1$ through $Z_4$ each independently represents CH or N), —S—CO—O—, —CH=CH—NH—, —CH=CH—S—, —CH=CH—O—, —N=CH—NH—, —CH_2—N=N—, —N=N—O—, —N=CH—S— or —O—CH_2CH_2—O—.

In a preferred embodiment of the fifteenth embodiment, $R_1$, $R_3$, $R_4$, $R_9$, $R_{11}$ and $R_{12}$ are each hydrogen;

$R_2$ and $R_{10}$ are each independently hydrogen, fluoro, chloro, bromo, cyano, acetyl, nitro, amino, borono, carboxyl, $C_{1-4}$ alkoxycarbonyl, phenoxycarbonyl, hydroxyl, —$SO_3H$, —$SO_2CH_3$ and —$SO_2NH_2$;

$R_5$ through $R_8$ are each independently hydrogen, $C_{1-4}$ alkyl, $C_{3-6}$ cycloalkyl, $C_{1-3}$ alkoxy, trifluoromethyl, fluoro, chloro, bromo, cyano, acetyl, amino, borono, nitro, carboxyl, $C_{1-4}$ alkoxycarbonyl, phenyl, phenoxy, phenoxycarbonyl, benzyloxy, hydroxyl, hydroxymethyl, —$SO_3H$, —$SO_2CH_3$, —$SO_2NH_2$, or when any two $R_i$s are located at the ortho position to each other, they together form -$Z_1$=$Z_2$-$Z_3$=$Z_4$- (wherein $Z_1$ through $Z_4$ each independently represents CH or N), —S—CO—O—, —CH=CH—NH—, —CH=CH—S—, —CH=CH—O—, —N=CH—NH—, —CH_2—N=N—, —N=N—O—, —N=CH—S— or —O—CH_2CH_2—O—.

Non-limiting specific compounds described by formula A(XV) are listed in Table 10.

TABLE 10

Representative Compounds in Formula A(XV):

| $R_1$ | $R_2$ | $R_3$ | $R_4$ | $R_5$ | $R_6$ | $R_7$ | $R_8$ | $R_9$ | $R_{10}$ | $R_{11}$ | $R_{12}$ |
|---|---|---|---|---|---|---|---|---|---|---|---|
| H | $NO_2$ | H | H | H | H | H | H | H | $NO_2$ | H | H |
| H | $NO_2$ | H | H | H | Br | H | H | H | $NO_2$ | H | H |
| H | $NO_2$ | H | H | $COCH_3$ | H | H | H | H | $NO_2$ | H | H |
| H | $NO_2$ | H | H | H | H | COOH | H | H | $NO_2$ | H | H |
| H | H | H | H | H | H | H | H | H | H | H | H |
| H | H | H | H | H | Br | H | H | H | H | H | H |
| H | H | H | H | $COCH_3$ | H | H | H | H | H | H | H |
| H | H | H | H | H | H | COOH | H | H | H | H | H |

Formula A(XVI)

In a sixteenth embodiment, the compounds of the present invention are represented by formula A(XVI):

A(XVI)

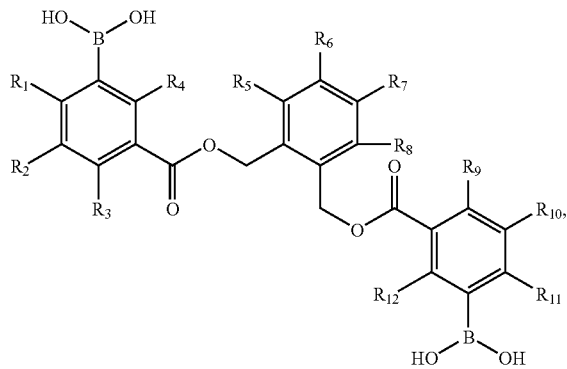

wherein $R_1$ through $R_{12}$ are each independently hydrogen, $C_{1-6}$ alkyl, $C_{3-6}$ cycloalkyl, $C_{1-3}$ alkoxy, n-butoxy, i-butoxy, sec-butoxy, $R_{13}R_{14}N$— (wherein $R_{13}$ and $R_{14}$ are each independently hydrogen or $C_{1-3}$ alkyl), trifluoromethyl, trifluoromethoxy, difluoromethoxy, fluoro, chloro, bromo, cyano, acetyl, amino, borono, nitro, carboxyl, $C_{1-6}$ alkoxycarbonyl, phenyl, phenoxy, phenoxycarbonyl, benzyloxy, hydroxyl, trimethylsilyloxy, diphenyl-t-butylsilyloxy, hydroxymethyl, —$SO_3H$, —$SO_2CH_3$, —$SO_2NHR_{15}$ (wherein $R_{15}$ is hydrogen or $C_{1-3}$ alkyl), or —$O(CH_2)_n OR_{16}$— (wherein $R_{16}$ is hydrogen or $C_{1-3}$ alkyl, and n is 1, 2 or 3); or when any two $R_i$s are located at the ortho position to each other, they together form -$Z_1=Z_2-Z_3=Z_4$- (wherein $Z_1$ through $Z_4$ each independently represents CH or N), —S—CO—O—, —CH=CH—NH—, —CH=CH—S—, —CH=CH—O—, —N=CH—NH—, —$CH_2$—N=N—, —N=N—O—, —N=CH—S— or —O—$CH_2CH_2$—O—.

In a preferred embodiment of the sixteenth embodiment, $R_1$, $R_3$, $R_4$, $R_9$, $R_{11}$ and $R_{12}$ are each hydrogen;
$R_2$ and $R_{10}$ are each independently hydrogen, fluoro, chloro, bromo, cyano, acetyl, nitro, amino, borono, carboxyl, $C_{1-4}$ alkoxycarbonyl, phenoxycarbonyl, hydroxyl, —$SO_3H$, —$SO_2CH_3$ and —$SO_2NH_2$;
$R_5$ through $R_8$ are each independently hydrogen, $C_{1-4}$ alkyl, $C_{3-6}$ cycloalkyl, $C_{1-3}$ alkoxy, trifluoromethyl, fluoro, chloro, bromo, cyano, acetyl, amino, borono, nitro, carboxyl, $C_{1-4}$ alkoxycarbonyl, phenyl, phenoxy, phenoxycarbonyl, benzyloxy, hydroxyl, hydroxymethyl, —$SO_3H$, —$SO_2CH_3$, —$SO_2NH_2$, or when any two $R_i$s are located at the ortho position to each other, they together form -$Z_1=Z_2-Z_3=Z_4$- (wherein $Z_1$ through $Z_4$ each independently represents CH or N), —S—CO—O—, —CH=CH—NH—, —CH=CH—S—, —CH=CH—O—, —N=CH—NH—, —$CH_2$—N=N—, —N=N—O—, —N=CH—S— or —O—$CH_2CH_2$—O—.

Non-limiting specific compounds described by formula A(XVI) are listed in Table 10A.

TABLE 10A

Representative Compounds in Formula A(XVI)

| $R_1$ | $R_2$ | $R_3$ | $R_4$ | $R_5$ | $R_6$ | $R_7$ | $R_8$ | $R_9$ | $R_{10}$ | $R_{11}$ | $R_{12}$ |
|---|---|---|---|---|---|---|---|---|---|---|---|
| H | $NO_2$ | H | H | H | H | H | H | H | $NO_2$ | H | H |
| H | H | H | H | H | H | H | H | H | H | H | H |

Formula A(XVII)

In a seventeenth embodiment, the compounds of the present invention are represented by formula A(XVII):

A(XVII)

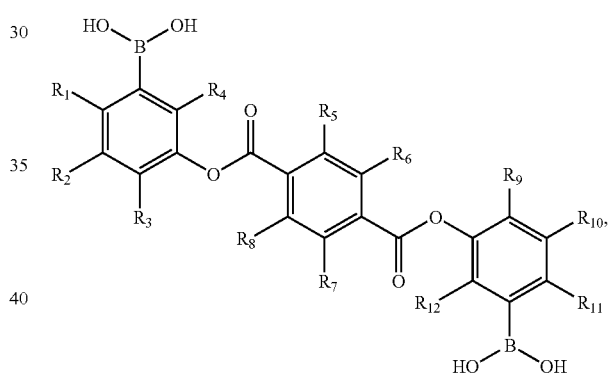

wherein $R_1$ through $R_{12}$ are each independently hydrogen, $C_{1-6}$ alkyl, $C_{3-6}$ cycloalkyl, $C_{1-3}$ alkoxy, n-butoxy, i-butoxy, sec-butoxy, $R_{13}R_{14}N$— (wherein $R_{13}$ and $R_{14}$ are each independently hydrogen or $C_{1-3}$ alkyl), trifluoromethyl, trifluoromethoxy, difluoromethoxy, fluoro, chloro, bromo, cyano, acetyl, amino, borono, nitro, carboxyl, $C_{1-6}$ alkoxycarbonyl, phenyl, phenoxy, phenoxycarbonyl, benzyloxy, hydroxyl, trimethylsilyloxy, diphenyl-t-butylsilyloxy, hydroxymethyl, —$SO_3H$, —$SO_2CH_3$, —$SO_2NHR_{15}$ (wherein $R_{15}$ is hydrogen or $C_{1-3}$ alkyl), or —$O(CH_2)_n OR_{16}$— (wherein $R_{16}$ is hydrogen or $C_{1-3}$ alkyl, and n is 1, 2 or 3); or when any two $R_i$s are located at the ortho position to each other, they together form -$Z_1=Z_2-Z_3=Z_4$- (wherein $Z_1$ through $Z_4$ each independently represents CH or N), —S—CO—O—, —CH=CH—NH—, —CH=CH—S—, —CH=CH—O—, —N=CH—NH—, —$CH_2$—N=N—, —N=N—O—, —N=CH—S— or —$CH_2CH_2$—O—.

In a preferred embodiment of the sixteenth embodiment, $R_1$, $R_3$, $R_4$, $R_9$, $R_{11}$ and $R_{12}$ are each hydrogen;
$R_2$ and $R_{10}$ are each independently hydrogen, fluoro, chloro, bromo, cyano, acetyl, nitro, amino, borono, carboxyl, $C_{1-4}$ alkoxycarbonyl, phenoxycarbonyl, hydroxyl, —$SO_3H$, —$SO_2CH_3$ and —$SO_2NH_2$;
$R_5$ through $R_8$ are each independently hydrogen, $C_{1-4}$ alkyl, $C_{3-6}$ cycloalkyl, $C_{1-3}$ alkoxy, trifluoromethyl, fluoro, chloro, bromo, cyano, acetyl, amino, borono, nitro, carboxyl, $C_{1-4}$ alkoxycarbonyl, phenyl, phenoxy, phenoxycarbonyl, benzyloxy, hydroxyl, hydroxymethyl, —$SO_3H$, —$SO_2CH_3$, —$SO_2NH_2$, or when any two $R_i$s are located at the ortho position to each other, they together form -$Z_1$=$Z_2$-$Z_3$=$Z_4$- (wherein $Z_1$ through $Z_4$ each independently represents CH or N), —S—CO—O—, —CH=CH—NH—, —CH=CH—S—, —CH=CH—O—, —N=CH—NH—, —$CH_2$—N=N—, —N=N—O—, —N=CH—S— or —O—$CH_2CH_2$—O—.

Non-limiting specific compounds described by formula A(XVII) are listed in Table 10B.

TABLE 10B

Representative Compounds in Formula A(XVII)

| $R_1$ | $R_2$ | $R_3$ | $R_4$ | $R_5$ | $R_6$ | $R_7$ | $R_8$ | $R_9$ | $R_{10}$ | $R_{11}$ | $R_{12}$ |
|---|---|---|---|---|---|---|---|---|---|---|---|
| H | $NO_2$ | H | H | H | H | H | H | H | $NO_2$ | H | H |
| H | H | H | H | H | H | H | H | H | H | H | H |

Formula A(XVIII)

In a eighteenth embodiment, the compounds of the present invention are represented by formula A(XVIII):

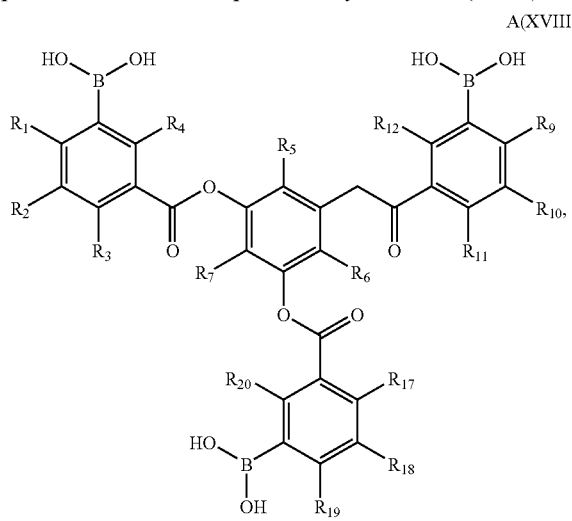

A(XVIII)

wherein $R_1$ through $R_{20}$ are each independently hydrogen, $C_{1-6}$ alkyl, $C_{3-6}$cycloalkyl, $C_{1-3}$ alkoxy, n-butoxy, i-butoxy, sec-butoxy, $R_{13}R_{14}N$— (wherein $R_{13}$ and $R_{14}$ are each independently hydrogen or $C_{1-3}$ alkyl), trifluoromethyl, trifluoromethoxy, difluoromethoxy, fluoro, chloro, bromo, cyano, acetyl, amino, borono, nitro, carboxyl, $C_{1-6}$ alkoxycarbonyl, phenyl, phenoxy, phenoxycarbonyl, benzyloxy, hydroxyl, trimethylsilyloxy, diphenyl-t-butylsilyloxy, hydroxymethyl, —$SO_3H$, —$SO_2CH_3$, —$SO_2NHR_{15}$ (wherein $R_{15}$ is hydrogen or $C_{1-3}$ alkyl), or —$O(CH_2)_n$ $OR_{16}$— (wherein $R_{16}$ is hydrogen or $C_{1-3}$ alkyl, and n is 1, 2 or 3); or when any two $R_i$s are located at the ortho position to each other, they together form -$Z_1$=$Z_2$-$Z_3$=$Z_4$- (wherein $Z_1$ through $Z_4$ each independently represents CH or N), —S—CO—O—, —CH=CH—NH—, —CH=CH—S—, —CH=CH—O—, —N=CH—NH—, —$CH_2$—N=N—, —N=N—O—, —N=CH—S— or —O—$CH_2CH_2$—O—.

In a preferred embodiment of the eighteenth embodiment, $R_1$, $R_3$, $R_4$, $R_9$, $R_{11}$, $R_{12}$, $R_{17}$, $R_{19}$ and $R_{20}$ are each hydrogen;

$R_2$, $R_{10}$ and $R_{18}$ are each independently hydrogen, fluoro, chloro, bromo, cyano, acetyl, nitro, amino, borono, carboxyl, $C_{1-4}$ alkoxycarbonyl, phenoxycarbonyl, hydroxyl, —$SO_3H$, —$SO_2CH_3$ and —$SO_2NH_2$;

$R_5$ through $R_7$ are each independently hydrogen, $C_{1-4}$ alkyl, $C_{3-6}$ cycloalkyl, $C_{1-3}$ alkoxy, trifluoromethyl, fluoro, chloro, bromo, cyano, acetyl, amino, borono, nitro, carboxyl, $C_{1-4}$ alkoxycarbonyl, phenyl, phenoxy, phenoxycarbonyl, benzyloxy, hydroxyl, hydroxymethyl, —$SO_3H$, —$SO_2CH_3$, —$SO_2NH_2$.

Non-limiting specific compounds described by formula A(XVIII) are listed in Table 10C.

TABLE 10C

Representative Compounds in Formula A(XVIII)

| $R_1$ | $R_2$ | $R_3$ | $R_4$ | $R_5$ | $R_6$ | $R_7$ | $R_9$ | $R_{10}$ | $R_{11}$ | $R_{12}$ | $R_{17}$ | $R_{18}$ | $R_{19}$ | $R_{20}$ |
|---|---|---|---|---|---|---|---|---|---|---|---|---|---|---|
| H | $NO_2$ | H | H | H | H | H | H | $NO_2$ | H | H | H | $NO_2$ | H | H |
| H | H | H | H | H | H | H | H | H | H | H | H | H | H | H |

β-Lactamases

The compounds of the present invention can be used to inhibit any lactamases.

β-lactamases are endogenous bacterial enzymes that destroy β-lactam antibiotics and eliminate their efficacy. The name derives from their ability to cleave the β-lactam ring. The structures of many β-lactamases are known at the atomic level and available in the protein database. Preferably, the β-lactamase is a Class A, B, C or D β-lactamase. More preferably, it is a Class A (TEM) or Class C (AmpC) β-lactamase.

Salts and Derivatives

Various pharmaceutically acceptable salts, ether derivatives, ester derivatives, acid derivatives, and aqueous solubility altering derivatives of the active compound also are encompassed by the present invention. The present invention further includes all individual enantiomers, diastereomers, racemates, and other isomer of the compound. The invention also includes all polymorphs and solvates, such as hydrates and those formed with organic solvents, of this compound. Such isomers, polymorphs, and solvates may be prepared by methods known in the art, such as by regiospecific and/or enantioselective synthesis and resolution, based on the disclosure provided herein.

Suitable salts of the compound include, but are not limited to, acid addition salts, such as those made with hydrochloric, hydrobromic, hydroiodic, perchloric, sulfuric, nitric, phosphoric, acetic, propionic, glycolic, lactic pyruvic, malonic, succinic, maleic, fumaric, malic, tartaric, citric, benzoic, carbonic cinnamic, mandelic, methanesulfonic, ethanesulfonic, hydroxyethanesulfonic, benezenesulfonic, p-toluene sulfonic, cyclohexanesulfamic, salicyclic, p-aminosalicylic, 2-phenoxybenzoic, and 2-acetoxybenzoic acid; salts made with saccharin; alkali metal salts, such as sodium and potassium salts; alkaline earth metal salts, such as calcium and magnesium salts; and salts formed with organic or inorganic ligands, such as quaternary ammonium salts.

Additional suitable salts include, but are not limited to, acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate salts of the compound of the present invention.

Prodrugs and active metabolites of compounds disclosed herein are also within the scope of the invention.

A prodrug is a pharmacologically inactive compound that is converted into a pharmacologically active agent by a metabolic transformation. In vivo, a prodrug is acted on by naturally occurring enzyme(s) resulting in liberation of the pharmacologically active agent. Conventional procedures for the selection and preparation of suitable prodrug derivatives are described, for example, in "Design of Prodrugs", ed. H. Bundgaard, Elsevier, 1985.

An active metabolite is a compound which results from metabolism of another compound after administration of the latter to a subject. Metabolites can be identified by techniques well-known in the art.

Formulation and Administration

Suitable dosage forms include but are not limited to oral, rectal, sub-lingual, mucosal, nasal, ophthalmic, subcutaneous, intramuscular, intravenous, transdermal, spinal, intrathecal, intra-articular, intra-arterial, sub-arachinoid, bronchial, lymphatic, and intra-uterille administration, and other dosage forms for systemic delivery of active ingredients.

To prepare such pharmaceutical dosage forms, one or more of the aforementioned compounds of formula (1), alone or in combination with β-lactam antibiotics, are intimately admixed with a pharmaceutical carrier according to conventional pharmaceutical compounding techniques. The carrier may take a wide variety of forms depending on the form of preparation desired for administration.

In preparing the compositions in oral dosage form, any of the usual pharmaceutical media may be employed. Thus, for liquid oral preparations, such as, for example, suspensions, elixirs and solutions, suitable carriers and additives include water, glycols, oils, alcohols, flavoring agents, preservatives, coloring agents and the like. For solid oral preparations such as, for example, powders, capsules and tablets, suitable carriers and additives include starches, sugars, diluents, granulating agents, lubricants, binders, disintegrating agents and the like. Due to their ease in administration, tablets and capsules represent the most advantageous oral dosage unit form. If desired, tablets may be sugar coated or enteric coated by standard techniques.

For parenteral formulations, the carrier will usually comprise sterile water, though other ingredients, for example, ingredients that aid solubility or for preservation, may be included. Injectable solutions may also be prepared in which case appropriate stabilizing agents may be employed.

In some applications, it may be advantageous to utilize the active agent in a "vectorized" form, such as by encapsulation of the active agent in a liposome or other encapsulant medium, or by fixation of the active agent, e.g., by covalent bonding, chelation, or associative coordination, on a suitable biomolecule, such as those selected from proteins, lipoproteins, glycoproteins, and polysaccharides.

Treatment methods of the present invention using formulations suitable for oral administration may be presented as discrete units such as capsules, cachets, tablets, or lozenges, each containing a predetermined amount of the active ingredient as a powder or granules. Optionally, a suspension in an aqueous liquor or a non-aqueous liquid may be employed, such as a syrup, an elixir, an emulsion, or a draught.

A tablet may be made by compression or molding, or wet granulation, optionally with one or more accessory ingredients. Compressed tablets may be prepared by compressing in a suitable machine, with the active compound being in a free-flowing form such as a powder or granules which optionally is mixed with a binder, disintegrant, lubricant, inert diluent, surface active agent, or discharging agent. Molded tablets comprised of a mixture of the powdered active compound with a suitable carrier may be made by molding in a suitable machine.

A syrup may be made by adding the active compound to a concentrated aqueous solution of a sugar, for example sucrose, to which may also be added any accessory ingredient(s). Such accessory ingredient(s) may include flavorings, suitable preservative, agents to retard crystallization of the sugar, and agents to increase the solubility of any other ingredient, such as a polyhydroxy alcohol, for example glycerol or sorbitol.

Formulations suitable for parenteral administration usually comprise a sterile aqueous preparation of the active compound, which preferably is isotonic with the blood of the recipient (e.g., physiological saline solution). Such formulations may include suspending agents and thickening agents and liposomes or other microparticulate systems which are designed to target the compound to blood components or one or more organs. The formulations may be presented in unit-dose or multi-dose form.

Parenteral administration may comprise any suitable form of systemic delivery or delivery directly to the CNS. Administration may for example be intravenous, intra-arterial, intrathecal, intramuscular, subcutaneous, intramuscular, intra-abdominal (e.g., intraperitoneal), etc., and may be effected by infusion pumps (external or implantable) or any other suitable means appropriate to the desired administration modality.

Nasal and other mucosal spray formulations (e.g. inhalable forms) can comprise purified aqueous solutions of the active compounds with preservative agents and isotonic agents. Such formulations are preferably adjusted to a pH and isotonic state compatible with the nasal or other mucous membranes. Alternatively, they can be in the form of finely divided solid powders suspended in a gas carrier. Such formulations may be delivered by any suitable means or method, e.g., by nebulizer, atomizer, metered dose inhaler, or the like.

Formulations for rectal administration may be presented as a suppository with a suitable carrier such as cocoa butter, hydrogenated fats, or hydrogenated fatty carboxylic acids.

Transdermal formulations may be prepared by incorporating the active agent in a thixotropic or gelatinous carrier such as a cellulosic medium, e.g., methyl cellulose or hydroxyethyl cellulose, with the resulting formulation then being packed in a transdermal device adapted to be secured in dermal contact with the skin of a wearer.

In addition to the aforementioned ingredients, formulations of this invention may further include one or more accessory ingredient(s) selected from diluents, buffers, flavoring agents, binders, disintegrants, surface active agents, thickeners, lubricants, preservatives (including antioxidants), and the like.

The formulation of the present invention can have immediate release, sustained release, delayed-onset release or any other release profile known to one skilled in the art.

β-Lactam Antibiotics

β-lactam antibiotics are compounds with antimicrobial activities and contain the β-lactam structure. Any β-lactam antibiotic is suitable. Many suitable β-lactam antibiotics are known (See e.g., R. B. Morin and M. Gorin, M. Eds.; Academic Press, New York, 1982; vol. 1–3). These include but not limited to cephalosporins (e.g., cephalothin), penicillins (e.g., amoxicillin), monobactams (e.g., aztreonam), carbapenems (e.g., imipenem), carbacephems (loracarbef), and others. β-lactam antibiotics are effective (in the absence of resistance) against a wide range of bacterial infections. These include those caused by gram-positive and/or gram-negative bacteria, for example, bacteria of the genus *Staphylococcus* (such as *Staphylococcus aureus* and *Staphylococcus epidermis*), *Streptococcus* (such as *Streptococcus agalactine, Streptococcus penumoniae* and *Streptococcus faecalis*), *Micrococcus* (such as *Micrococcus luteus*), *Bacillus* (such as *Bacillus subtilis*), *Listerella* (such as *Listerella monocytogenes*), *Escherichia* (such as *Escherichia coli*), *Klebsiella* (such as *Klebsiella pneumoniae*), *Proteus* (such as *Proteus mirabilis* and *Proteus vulgaris*), *Salmonella* (such as *Salmonella typhosa*), *Shigella* (such as *Shigella sonnei*), *Enterobacter* (such as *Enterobacter aerogenes* and *Enterobacterfacium*), *Serratia* (such as *Serratia marcescens*), *Pseudomonas* (such as *Pseudomonas aeruginosa*), *Acinetobacter* such as *Acinetobacter anitratus*), *Nocardia* (such as *Nocardia autotrophica*), or *Mycobacterium* (such as *Mycobacterium fortuitum*). Preferred β-lactam antibiotics are those which preferentially deactivated by Class A and Class C β-lactamase enzymes, for example, amoxicillin, piperacillin, ampicillin, ceftizoxime, cefotaxime, cefuroxime, cephalexin, cefaclor, cephaloridine, and ceftazidime. Effective doses and modes of administration of β-lactam antibiotics, alone or in combination with β-lactamase inhibitor(s), are known in the art or may be determined empirically by one skilled on the art.

Combination Treatments

The compounds disclosed herein may be used in combination with with one or more other antibacterial agent for any of the aforementioned methods, including without limitation, any of the aforementioned methods of treatment. Preferred classes of antibacterial agents for use in combination with the compounds disclosed herein are, without limition, β-lactam antibiotics, described supra, fluoroquinolones, quinolones, macrolides, and tetracyclines. Examples of fluoroquinolones include, without limitation, ciprofloxacin, clinafloxacin, enoxacin, fleroxacin, gatifloxacin, moxifloxacin, gemifloxacin, grepafloxacin, levofloxacin, norfloxacin, sparfloxacin, and trovafloxacin. Examples of quinolones include, without limitation, cinoxacin, garenoxacin, and nalidixic acid. Examples of macrolides include, without limitation, azithromycin, clarithromycin, dirithromycin, erythromycin, and lincomycin. Examples of tetracyclines include, without limitation, doxycycline, minocycline, and tetracycline.

The term "in combination" refers to the concomitant administration of two (or more) active agents for the treatment of a, e.g., single disease state. As used herein, the active agents may be combined and administered in a single dosage form, may be administered as separate dosage forms at the same time, or may be administered as separate dosage forms that are administered alternately or sequentially on the same or separate days. In one preferred embodiment of the present invention, the active agents are combined and administered in a single dosage form. In another preferred embodiment, the active agents are administered in separate dosage forms (e.g., wherein it is desirable to vary the amount of one but not the other). The single dosage form may include additional active agents for the treatment of the disease state.

EXAMPLES

The following examples illustrates the invention, but are not limiting.

Example 1

Synthesis of Select Compounds in Formulation A(I)

General Procedure A: Synthesis of 3-aryloxycarbonyl-phenylboronic acid

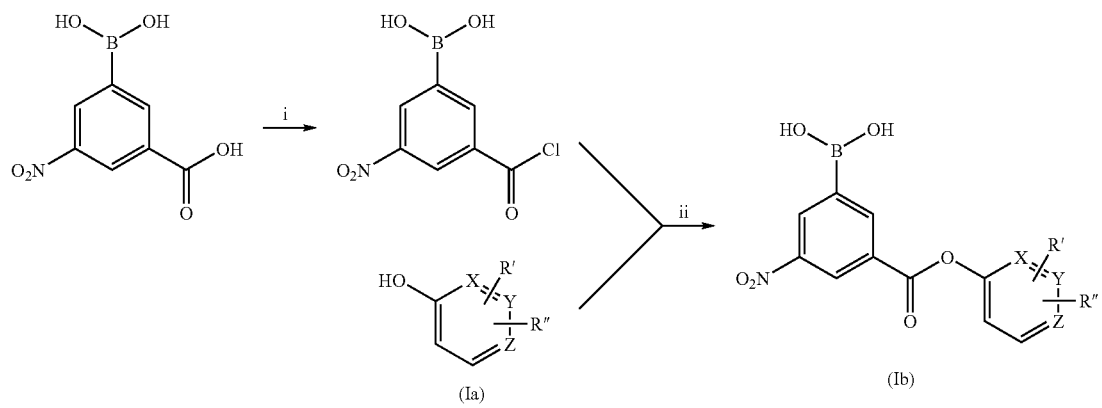

step i, (COCl)$_2$, DMF, CH$_2$Cl$_2$, rt, overnight
step ii, Et$_3$N, CH$_2$Cl$_2$, rt, overnight In step (i) of general procedure A, oxalyl chloride (35 μL, 0.4 mmol) was added to a suspension of (3-carboxyl-5-nitrophenyl)boronic acid (42 mg, 0.2 mmol), 1 drop of DMF and 5 mL of anhydrous CH$_2$Cl$_2$. The reaction mixture was stirred at room temperature overnight and then evaporated to dryness to afford acid chloride as a yellow solid, which was used without further purification.

In step (ii) of general procedure A, a solution of the acid chloride (0.2 mmol, obtained from step (i) above) in 5 mL of anhydrous CH$_2$Cl$_2$ was added dropwise to an ice-cold solution of (Ia), anhydrous triethyl amine (42 μL, 0.3 mmol) and 10 mL of anhydrous CH$_2$Cl$_2$. The reaction mixture was stirred at room temperature overnight and then evaporated to dryness. It was then dissolved in 25 mL of ethyl acetate and washed with 1N aqueous HCl, 10% aqueous NaHCO$_3$, saturated brine solution, dried (Na$_2$SO$_4$) and then concentrated. The residue was purified by flash chromatography eluting with MeOH-ethyl acetate (1:10). The product yielded from step (ii) is (Ib).

Compound (1a)
(3-(4-Nitrophenoxycarbonyl)-5-nitrophenylboronic acid)

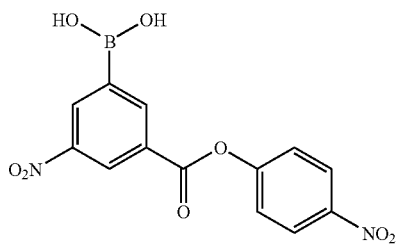

To make compound (1a) p-Nitrophenol (21 mg, 0.15 mmol) was treated according to general procedure A, step (ii), to yield 42 mg (84% yield) of 3-(4-Nitrophenoxycarbonyl)-5-nitrophenylboronic acid as a white powder, mp: 205–207° C.

$^1$H-NMR(300 MHz, d$_6$-DMSO): δ7.61–7.66 [m, 2H, Ar—H], 8.30–8.35 [m, 2H, Ar—H], 8.78–8.89 [m, 3H, Ar—H].

Compound (1b)
(3-(2-Nitrophenoxycarbonyl)-5-nitrophenylboronic acid)

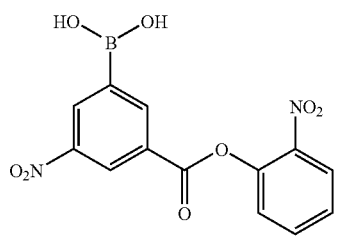

To make the compound (1b) o-Nitrophenol (21 mg, 0.15 mmol) was treated according to general procedure A, step (ii), to give 36 mg (72% yield) of 3-(2-Nitrophenoxycarbonyl)-5-nitrophenylboronic acid as a pale yellow powder, mp: 128–130° C. $^1$H-NMR(300 MHz, d$_6$-DMSO): δ7.52–7.71 [m, 2H, Ar—H], 7.81–7.94 [m, 1H, Ar—H], δ8.13–8.24 [m, 1H, Ar—H], 8.70–8.93 [m, 3H, Ar—H].

Compound (1c)
(3-(3-Nitrophenoxycarbonyl)-5-nitrophenylboronic acid)

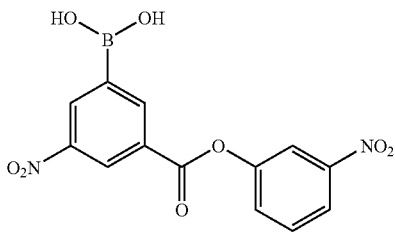

To make compound (1c), m-Nitrophenol (21 mg, 0.15 mmol) was treated according to general procedure A, step (ii), to give 41 mg (82% yield) of 3-(3-Nitrophenoxycarbonyl)-5-nitrophenylboronic acid as a light yellow crystal, mp: 185–187° C. $^1$H-NMR(300 MHz, d$_6$-DMSO): δ7.72–7.81 [m, 2H, Ar—H], δ8.15–8.29 [m, 2H, Ar—H], 8.76–8.89 [m, 3H, Ar—H].

Compound (1d)
(3-(4-Methoxyphenoxycarbonyl)-5-nitrophenylboronic acid)

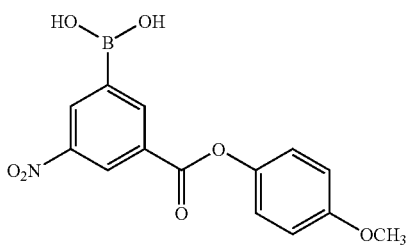

To make compound (1d), p-Methoxyphenol (19 mg, 0.15 mmol) was treated according to general procedure A, step (ii), to give 39 mg (81% yield) of 3-(4-Methoxyphenoxycarbonyl)-5-nitrophenylboronic acid as a white needle, mp: 67° C. $^1$H-NMR(300 MHz, d$_6$-DMSO): δ3.74 [s, 3H, OCH$_3$], 6.93–6.99 [m, 2H, Ar—H], 7.19–7.24 [m, 2H, Ar—H], 8.72–8.87 [m, 3H, Ar—H].

Compound (1e) (3-(4-Ethoxycarbonylphenoxycarbonyl)-5-nitrophenylboronic acid)

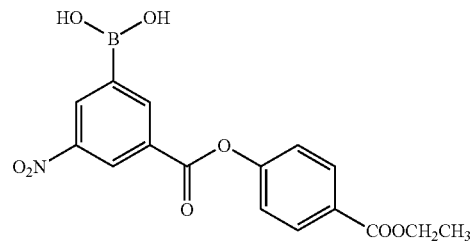

To make compound (1e), ethyl 4-hydroxybenzoate (25 mg, 0.15 mmol) was treated according to general procedure A, step (ii), to give 51 mg (94% yield) of the desired compound as a white powder, mp: 230–232° C. $^1$H-NMR (400 MHz, d$_6$-DMSO): δ 1.31 [t, 2H, CH$_2$CH$_3$], 4.30 [q, 3H, CH$_2$CH$_3$], 7.50 [d, 2H, Ar—H], 8.05 [d, 2H, Ar—H], 8.78–8.90 [m, 3H, Ar—H].

Compound (1f) (3-(2-OxO-benzo[1,3]oxathiol-6-oxycarbonyl)-5-nitrophenylboronic acid)

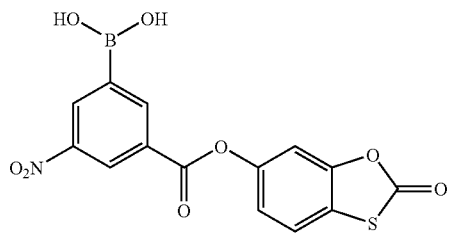

To make compound (1f), 6-Hydroxy-1,3-benzoxathiol-2-one (25 mg, 0.15 mmol) was treated according to general procedure A, step (ii), to give 50 mg (92% yield) of the desired compound as a white powder, mp: 145–147° C. $^1$H-NMR(300 MHz, d$_6$-DMSO): δ7.28–7.36 [m, 1H, Ar—H], 7.56–7.64 [m, 1H, Ar—H], 7.78–7.86 [m, 1H, Ar—H], 8.72–8.86 [m, 3H, Ar—H].

Compound (1g) (3-(2-Cyanophenoxycarbonyl)-5-nitrophenylboronic acid)

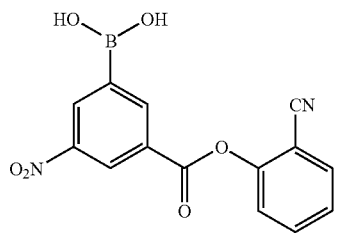

To make compound (1g), 2-Hydroxybenzonitrile (18 mg, 0.15 mmol) was treated according to general procedure A, step (ii), to give 43 mg (92% yield) of the desired compound as a white powder, mp: 248–250° C. $^1$H-NMR(400 MHz, d$_6$-DMSO): δ7.48–7.57 [m, 1H, Ar—H], 7.62–7.69 [m, 1H, Ar—H], 7.78–7.89 [m, 1H, Ar—H], 7.96–8.01 [m, 1H, Ar—H], 8.83–8.94 [m, 3H, Ar—H].

Compound (1h) (3-(2-Chloro-6-nitrophenoxycarbonyl)-5-nitrophenylboronic acid)

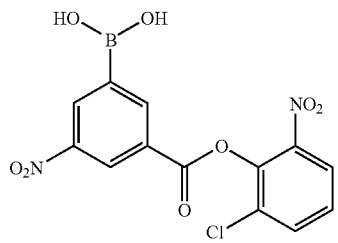

To make compound (1h), 2-Chloro-6-nitrophenol (26 mg, 0.15 mmol) was treated according to general procedure A, step (ii), to give 39 mg (71% yield) of the desired compound as a yellow needle, mp: 179° C. $^1$H-NMR(300 MHz, d$_6$-DMSO): δ7.54–7.72 [m, 1H, Ar—H], 8.01–8.24 [m, 2H, Ar—H], 8.65–8.94 [m, 3H, Ar—H].

Compound (1i) (3-(2-Ethoxycarbonyl-phenoxycarbonyl)-5-nitrophenylboronic acid)

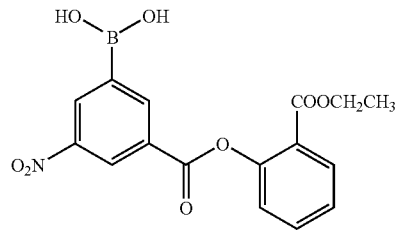

To make compound (1i), ethyl salicylate (25 mg, 0.15 mmol) was treated according to general procedure A, step (ii), to give 35 mg (64% yield) of the desired compound as a yellow semisolid. $^1$H-NMR(300 MHz, d$_6$-DMSO): δ1.24 [t, 2H, CH$_2$CH$_3$], 4.31 [q, 3H, CH$_2$CH$_3$], 7.41–7.57 [m, 2H, Ar—H], 7.81–8.05 [m, 2H, Ar—H], 8.67–8.93 [m, 3H, Ar—H].

Compound (1j) (3-(2-Chlorophenoxycarbonyl)-5-nitrophenylboronic acid)

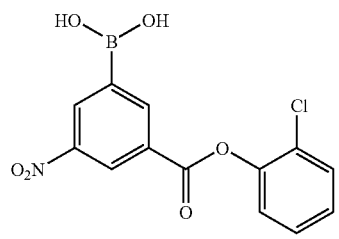

To make compound (1j), o-Chlorophenol (19 mg, 0.15 mmol) was treated according to general procedure A, step (ii), to give 44 mg (90% yield) of the desired compound as a white powder, mp: 138–140C. $^1$H-NMR(300 MHz, d$_6$-DMSO): δ 7.38–7.78 [m, 4H, Ar—H], 8.71–9.04 [m, 3H, Ar—H].

Compound (1k) (3-(2-Methylphenoxycarbonyl)-5-nitro-phenylboronic acid)

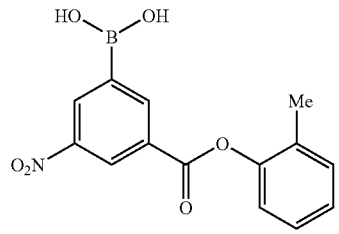

To make compound (1k), o-Cresol (16 mg, 0.15 mmol) was treated according to general procedure A, step (ii), to give 40 mg (89% yield) of the desired compound as a yellow powder, mp: 175° C.(dec). $^1$H-NMR(300 MHz, d$_6$-DMSO): δ2.17 [t, 3H, CH$_3$], 7.21–7.40 [m, 3H, Ar—H], 8.15–8.22 [m, 1H, Ar—H], 8.65–8.91 [m, 3H, Ar—H].

Compound (1l) (3-(2-Methoxylphenoxycarbonyl)-5-nitrophenylboronic acid)

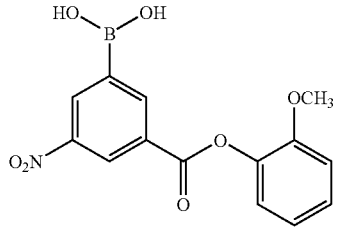

To make compound (1l), guaiacol (19 mg, 0.15 mmol) was treated according to general procedure A, step (ii), to give 44 mg (92% yield) of the desired compound as a yellow semisolid. $^1$H-NMR(300 MHz, d$_6$-DMSO): δ3.69[s, 3H, OCH$_3$], 7.46–8.03 [m, 4H, Ar—H], 8.64–8.97 [m, 3H, Ar—H].

Compound (1 m) (3-(3-Methylphenoxycarbonyl)-5-nitrophenylboronic acid)

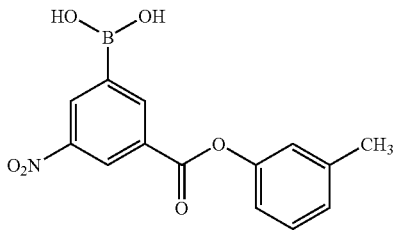

To make compound (1m), m-Cresol (16 mg, 0.15 mmol) was treated according to general procedure A, step (ii), to give 41 mg (91% yield) of the desired compound as a yellow semisolid. $^1$H-NMR(300 MHz, d$_6$-DMSO): δ 2.35 [t, 3H, CH$_3$], 7.79–8.30 [m, 4H, Ar—H]; 8.71–8.91 [m, 3H, Ar—H].

Compound (1n) (3-(2,6-Dichlorophenoxycarbonyl)-5-nitrophenylboronic acid)

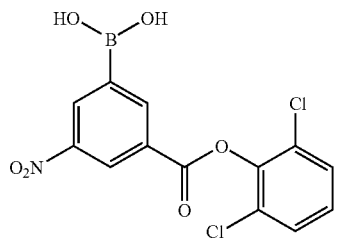

To make compound (1n), 2,6-Dichlorophenol (25 mg, 0.15 mmol) was treated according to general procedure A, step (ii), to give 43 mg (80% yield) of the desired compound as a pale yellow powder, mp: 167–169° C. $^1$H-NMR(300 MHz, d$_6$-DMSO): δ7.39–7.44 [m, 1H, Ar—H], 7.52–7.67 [m, 2H, Ar—H], 8.83 [t, 1H, Ar—H], 8.94–8.96 [m, 2H, Ar—H].

Compound (1o) (3-(2-Fluorophenoxycarbonyl)-5-nitrophenylboronic acid)

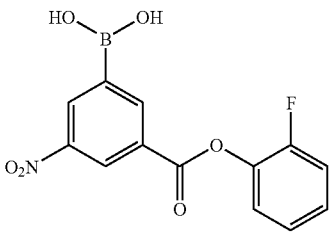

To make compound (1o), 2-Fluorophenol (17 mg, 0.15 mmol) was treated according to general procedure A, step (ii), to give 39 mg (85% yield) of the desired compound as a white needle, mp: 144–146° C. $^1$H-NMR (400 MHz, d$_6$-DMSO+D$_2$O): δ7.29–7.53 [m, 4H, Ar—H], 8.80 [s, 1H, Ar—H], 8.89–8.93 [m, 2H, Ar—H].

Compound (1p) (3-(2,6-Difluorophenoxycarbonyl)-5-nitrophenylboronic acid)

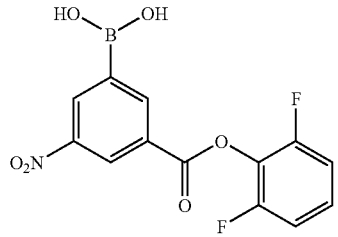

To make compound (1p), 2,6-Difluorophenol (20 mg, 0.15 mmol) was treated according to general procedure A, step (ii), to give 39 mg (81% yield) of the desired compound as a white powder, mp: 124–126° C. $^1$H-NMR(400 MHz, d$_6$-DMSO+D$_2$O): δ7.23–7.38 [m, 2H, Ar—H], 7.38–7.48 [m, 1H, Ar—H], 8.81 [s, 1H, Ar—H], 8.86–8.96 [m, 2H, Ar—H].

Compound (1q) (3-(4-Fluorophenoxycarbonyl)-5-nitrophenylboronic acid)

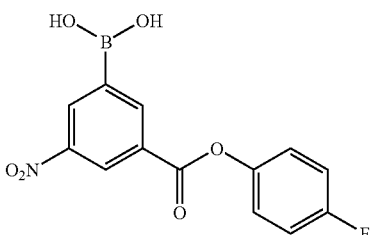

To make compound (1q), 4-Fluorophenol (17 mg, 0.15 mmol) was treated according to general procedure A, step (ii), to give 41 mg (89% yield) of the desired compound as a white powder, mp: 233–235° C. $^1$H-NMR(400 MHz, 5% D$_2$O in d$_6$-DMSO): δ7.21–7.42 [m, 4H, Ar—H], 8.76 [s, 1H, Ar—H], 8.83–8.95 [m, 2H, Ar—H].

Compound (1 r) (3-(4-pyridyloxycarbonyl)-5-nitro-phenylboronic acid)

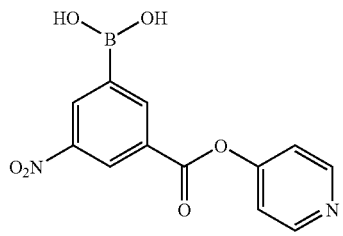

To make compound (1r), 4-Pyridinol (14 mg, 0.15 mmol) was treated according to general procedure A, step (ii), to give 34 mg (79% yield) of title compound as a pale yellow powder, mp: 165° C.(dec). $^1$H-NMR(400 MHz, 5% D$_2$O in d$_6$-DMSO): δ7.43–7.50 [m, 1H, Ar—H], 8.67–8.72 [m, 1H, Ar—H], 8.77–8.86 [m, 3H, Ar—H], 8.86–8.97 [m, 1H, Ar—H].

Compound (1s) (3-(2-Chloro-3-pyridyloxycarbonyl)-5-nitrophenylboronic acid)

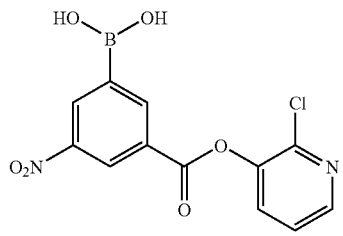

To make compound (1s), 2-Chloro-3-pyridinol (19 mg, 0.15 mmol), was treated according to general procedure A, step (ii), to give 37 mg (77% yield) of the desired compound as a white powder, mp: 146–148° C. $^1$H-NMR(400 MHz, 5% D$_2$O in d$_6$-DMSO): δ7.57–7.63 [m, 1H, Ar—H], 8.05–8.09 [m, 1H, Ar—H], 8.39–8.43 [m, 1H, Ar—H], 8.81 [s, 1H, Ar—H], 8.89–8.94 [m, 2H, Ar—H].

Compound (1t) (3-Phenoxycarbonyl-5-nitrophenylboronic acid)

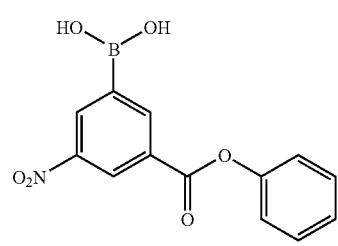

To make compound (1t), phenol (14 mg, 0.15 mmol) was treated according to general procedure A, step (ii), to give 39 mg (91% yield) of the desired compound as a white needle, mp: 139–141° C. $^1$H-NMR(400 MHz, 5% D$_2$O in d$_6$-DMSO): δ7.28–7.34 [m, 3H, Ar—H], 7.44–7.51 [m, 2H, Ar—H], 8.78 [s, 1H, Ar—H], 8.86–8.92 [m, 2H, Ar—H].

Compound (1 u) (3-(2-Bromophenoxycarbonyl)-5-nitro-phenylboronic acid)

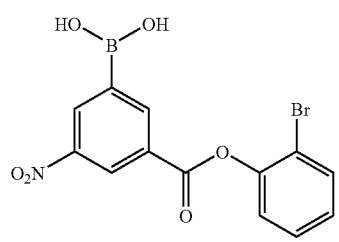

To make compound (1u), 2-Bromophenol (26 mg, 0.15 mmol) was treated according to general procedure A, step (ii), to give 49 mg (90% yield) of the desired compound as a pale yellow powder, mp: 128–130° C. $^1$H-NMR(400 MHz, 5% D$_2$O in d$_6$-DMSO): δ7.26–7.35 [m, 1H, Ar—H], 7.47–7.56 [m, 2H, Ar—H], 7.76–7.81 [m, 1H, Ar—H], 8.83–8.94 [m, 3H, Ar—H].

Compound (1v) (3-(3-Boronophenoxycarbonyl)-5-nitrophenylboronic acid)

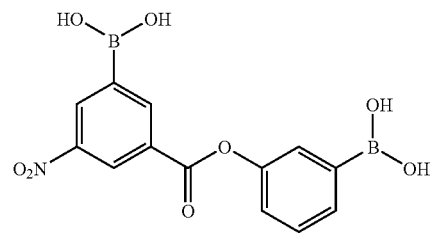

To make compound (1v), 3-Hydroxyphenylboronic acid (21 mg, 0.15 mmol) was treated according to general procedure A, step (ii), to give 32 mg (64% yield) of the desired compound as a pale yellow powder, mp: 228–230° C. $^1$H-NMR (400 MHz, 5% D$_2$O in d$_6$-DMSO): δ7.30–7.36 [m, 1H, Ar—H], 7.41–7.47 [m, 1H, Ar—H], 7.60–7.63 [m, 1H, Ar—H], 7.68–7.73 [m, 1H, Ar—H], 8.76–8.79 [m, 1H, Ar—H], 8.84–8.90 [m, 2H, Ar—H].

Compound (1w) (3-(2,4-Dichloro-6-nitro-phenoxycarbonyl)-5-nitro-phenylboronic acid)

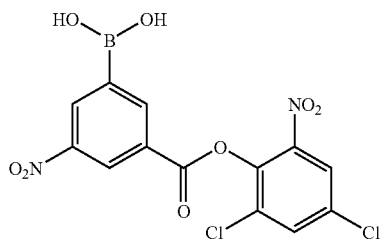

To make compound (1w), 2,4-Dichloro-6-nitrophenol (80%) (39 mg, 0.15 mmol) was treated according to general procedure A, step (ii), to give 52 mg (87% yield) of the desired compound as a pale yellow powder, mp: 184–186° C. $^1$H-NMR (400 MHz, 5% D$_2$O in d$_6$-DMSO): 8.34–8.38 [m, 1H, Ar—H], 8.82–8.84 [m, 1H, Ar—H], 8.90–8.91 [m, 1H, Ar—H], 8.94–8.96 [m, 1H, Ar—H].

Compound (1x) (3-(2,4-Dichloro-6-nitro-phenoxycarbonyl)-5-nitro-phenylboronic acid)

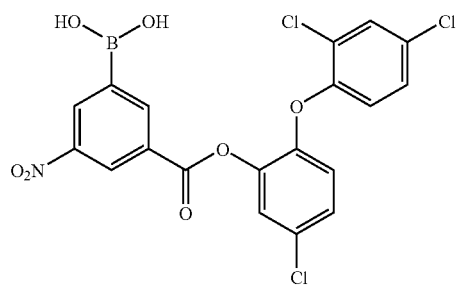

To make compound (1x), 5-Chloro-2-(2,4-dichlorophenoxy)phenol (43 mg, 0.15 mmol) was treated according to general procedure A, step (ii), to give 51 mg (71% yield) of the desired compound as a pale yellow powder, mp: 193° C. $^1$H-NMR (400 MHz, 5% D$_2$O in d$_6$-DMSO): δ6.61–6.94 [m, 3H, Ar—H], 7.15–8.07 [m, 3H, Ar—H], 8.71–8.76 [m, 1H, Ar—H], 8.84–8.89 [m, 1H, Ar—H], 8.89–8.96 [m, 1H, Ar—H].

Compound (1y) (3-(2,4,6-Trichlorophenoxycarbonyl)-5-nitro-phenylboronic acid)

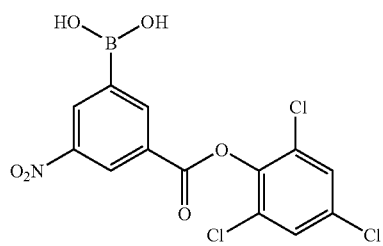

To make compound (1y), 2,4,6-Trichlorophenol (30 mg, 0.15 mmol) was treated according to general procedure A, step (ii), to give 45 mg (77% yield) of the desired compound as a white powder, mp: 217° C.(dec). $^1$H-NMR (400 MHz, 5% D$_2$O in d$_6$-DMSO): δ7.24 [s, 2H, Ar—H], 8.77–8.80 [m, 1H, Ar—H], 8.90–8.96 [m, 2H, Ar—H].

Example 2

Synthesis of Select Compounds in Formulation A(II)

General Procedure B: Synthesis of 3-borono-5-nitrobenzoic acid 1,4-phenylene ester

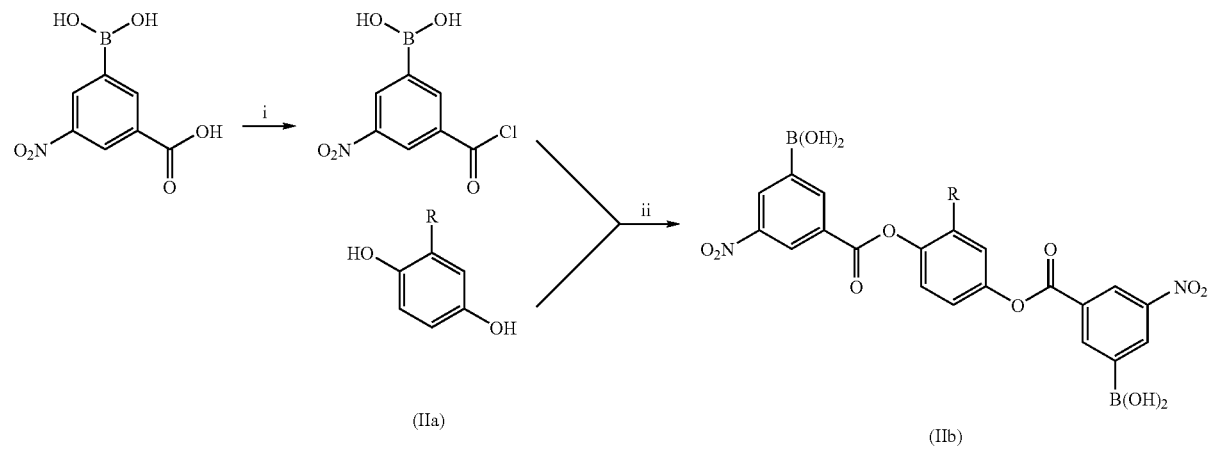

i, (COCl)$_2$, DMF, CH$_2$Cl$_2$, rt, overnight
ii, Et$_3$N, rt, overnight

In step (i) of general procedure B, oxalyl chloride (35 μL, 0.4 mmol) was added to a suspension of (3-carboxyl-5-nitrophenyl)boronic acid (42 mg, 0.2 mmol), 1 drop of DMF and 5 mL of anhydrous CH$_2$Cl$_2$. The reaction mixture was stirred at room temperature overnight and then evaporated to dryness to afford acid chloride as a yellow solid, which was used without further purification.

In step (ii) of general procedure B, a solution of the acid chloride (0.2 mmol, obtained above in step (i)) in 5 mL of anhydrous THF was added dropwise to an ice-cold solution of 0.075 mmol of (IIa), anhydrous triethyl amine (42 μL, 0.3 mmol) and 10 mL of anhydrous THF. The reaction mixture was stirred at room temperature overnight and then evaporated to dryness. It was then dissolved in 25 mL of ethyl acetate and washed with 1N aqueous HCl, 10% aqueous NaHCO$_3$, saturated brine solution, dried (Na$_2$SO$_4$) and concentrated. The residue was recrystallized from ethyl acetate/hexane. The product yielded from step (ii) is (IIb).

Compound (2a) (3-Borono-5-nitrobenzoic acid 1,4-phenylene ester)

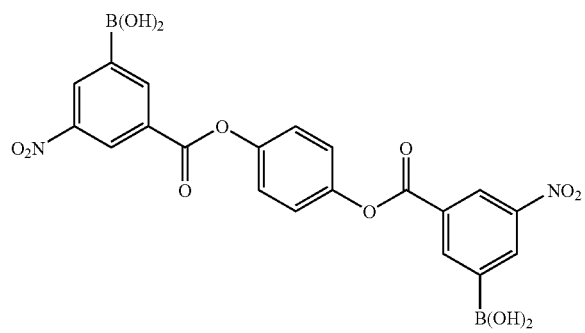

To make the compound (2a), hydroquinone (9 mg, 0.075 mmol) was treated according to general procedure B, step (ii), to give 32 mg (86% yield) of the desired compound as a white powder, mp: 271–273° C. $^1$H-NMR(300 MHz, d$_6$-DMSO+D$_2$O): δ7.43 [s, 4H, Ar—H], 8.79 [t, 1H, Ar—H], 8.84 [t, 1H, Ar—H], 8.86 [d, 1H, Ar—H].

Compound (2b) (3-Borono-5-nitrobenzoic acid 2-chloro-1,4-phenylene ester)

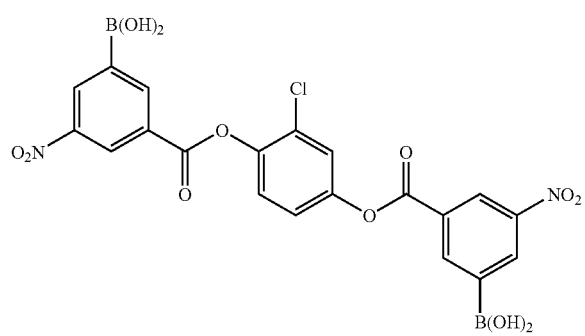

To make compound (2b), chlorohydroquinone (11 mg, 0.075 mmol) was treated according to general procedure B, step (ii), to give 31 mg (78% yield) of the deisred compound as a white powder, mp: 264–266° C. $^1$H-NMR(300 MHz, d$_6$-DMSO): δ 7.46–7.79 [m, 3H, Ar—H], 8.79 [d, 1H, Ar—H], 8.88–8.92 [m, 2H, Ar—H].

Compound (2c) (3-Borono-5-nitrobenzoic acid 2-chloro-1,4-phenylene ester)

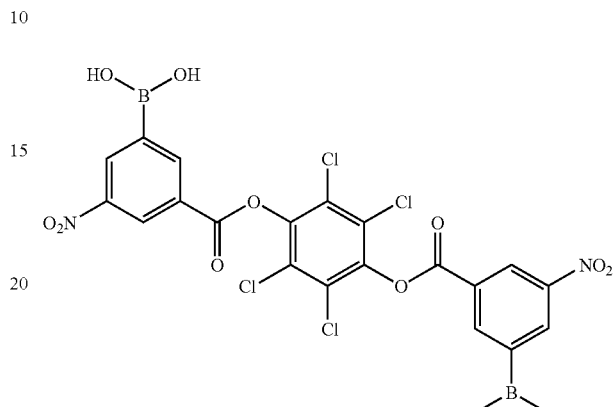

To make compound (2c), tetrachlorohydroquinone (19 mg, 0.075 mmol) was treated according to general procedure B, step (ii), to give 33 mg (69% yield) of the desired compound as a white powder, mp: 252° C. $^1$H-NMR(300 MHz, d$_6$-DMSO): δ8.71–8.75 [m, 2H, Ar—H], 8.93–8.99 [m, 4H, Ar—H].

Compound (2d) (3-Borono-5-nitrobenzoic acid 2-chloro-1,4-phenylene ester)

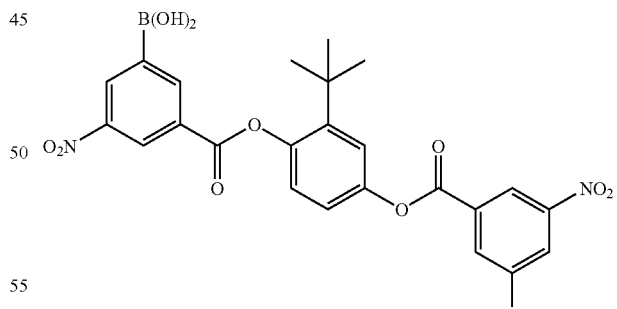

To make compound (2d), t-butylhydroquinone (12 mg, 0.075 mmol) was treated according to general procedure B, step (ii), to give 54 mg (65% yield) of the desired compound as a pale yellow powder, mp: 104° C.(dec). $^1$H-NMR(300 MHz, d$_6$-DMSO): δ1.34[s, 9H, CH$_3$], 7.02–7.27 [m, 3H, Ar—H], 8.79–8.83 [m, 2H, Ar—H], 8.86–8.92 [m, 4H, Ar—H].

Example 3

Synthesis of Select Compounds in Formulation A(III)

General Procedure C: Synthesis of 3-aryloxycarbonyl-phenylboronic acid

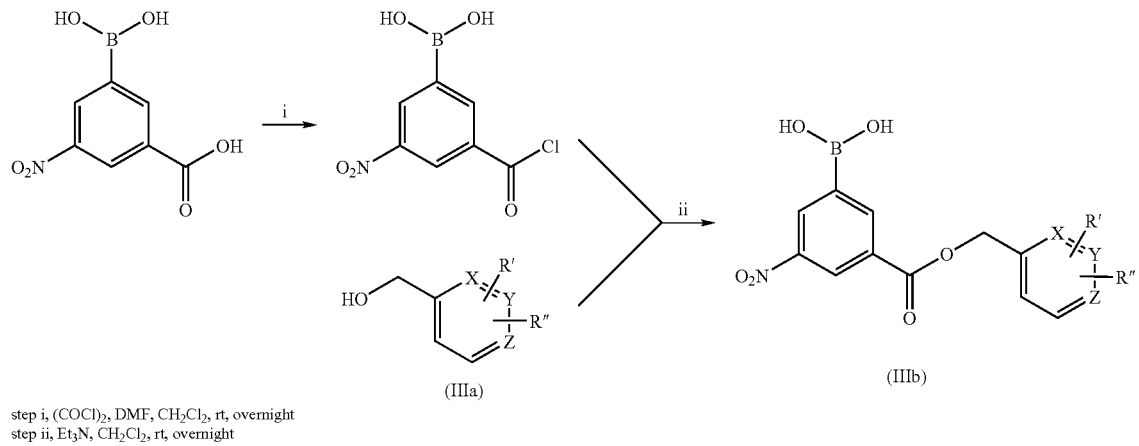

step i, (COCl)$_2$, DMF, CH$_2$Cl$_2$, rt, overnight
step ii, Et$_3$N, CH$_2$Cl$_2$, rt, overnight In step (i) of general procedure C, oxalyl chloride (35 µL, 0.4 mmol) was added to a suspension of (3-carboxyl-5-nitrophenyl)boronic acid (42 mg, 0.2 mmol), 1 drop of DMF and 5 mL of anhydrous CH$_2$Cl$_2$. The reaction mixture was stirred at room temperature overnight and then evaporated to dryness to afford acid chloride as a yellow solid, which was used without further purification.

In step (ii) of general procedure C, a solution of the acid chloride (0.2 mmol, obtained from step (i) above) in 5 mL of anhydrous CH$_2$Cl$_2$ was added dropwise to an ice-cold solution of (IIIa), anhydrous triethyl amine (42 µL, 0.3 mmol) and 10 mL of anhydrous CH$_2$Cl$_2$. The reaction mixture was stirred at room temperature overnight and then evaporated to dryness. It was then dissolved in 25 mL of ethyl acetate and washed with 1N aqueous HCl, 10% aqueous NaHCO$_3$, saturated brine solution, dried (Na$_2$SO$_4$) and then concentrated. The residue was purified by flash chromatography eluting with MeOH-ethyl acetate (1:10). The product yielded from step (ii) is (IIIb).

Compound (3a) (3-(2,6-Dichlorobenzyloxycarbonyl)-5-nitrophenylboronic)

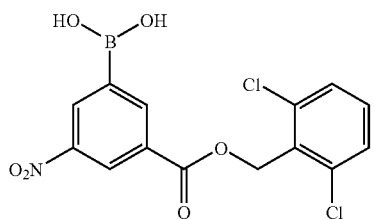

To make compound (3a), 2,6-Dichlorobenzyl alcohol (27 mg, 0.15 mmol) was treated according to general procedure C, step (ii), to give 49 mg (89% yield) of the desired compound as a pale yellow semisolid. $^1$H-NMR(400 MHz, 5% D$_2$O in d$_6$-DMSO): δ5.62 [s, 2H, Ar—CH$_2$], 7.26–7.62 [m, 3H, Ar—H], 8.57–8.95 [m, 3H, Ar—H].

Compound (3b)
(3-(3-Nitrobenzyloxycarbonyl)-5-nitrophenylboronic acid)

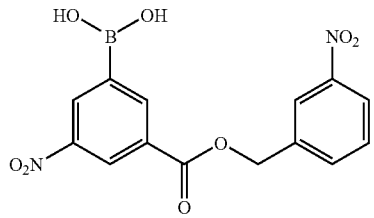

To make compound (3b), 3-Nitrobenzyl alcohol (23 mg, 0.15 mmol) was treated according to general procedure C, step (ii), to give 43 mg (82% yield) of the desired compound as a pale yellow powder, mp: 142–144° C. $^1$H-NMR (400 MHz, 5% D$_2$O in d$_6$-DMSO): δ5.46 [s, 2H, Ar—CH$_2$], 7.65–7.70 [m, 1H, Ar—H], 7.93–7.97 [m, 1H, Ar—H], 8.09–8.12 [m, 1H, Ar—H], 8.17–8.21 [m, 1H, Ar—H], 8.62–8.94 [m, 3H, Ar—H].

Compound (3c) (3-(3-Chlorobenzyloxycarbonyl)-5-nitrophenylboronic acid)

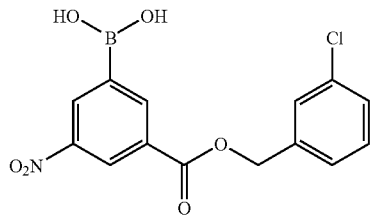

To make compound (3c), 3-Chlorobenzyl alcohol (22 mg, 0.15 mmol) was treated according to general procedure C, step (ii), to give 44 mg (88% yield) of the desired compound as a white powder, mp: 91° C.(dec). $^1$H-NMR(400 MHz, 5% D$_2$O in d$_6$-DMSO): δ5.41 [s, 2H, Ar—CH$_2$], 7.41–7.61 [m, 4H, Ar—H], 8.62–8.95 [m, 3H, Ar—H].

Compound (3d) (3-(3-Boronobenzyloxycarbonyl)-5-nitrophenylboronic acid)

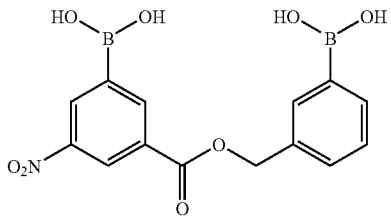

To make compound (3d), 3-Hydroxymethylphenylboronic acid (23 mg, 0.15 mmol) was treated according to general procedure C, step (ii), to give 35 mg (68% yield) of the desired compound as a yellow semisolid. $^1$H-NMR (400 MHz, 5% $D_2O$ in $d_6$-DMSO): δ5.39 [s, 2H, Ar—$CH_2$], 7.27–7.84 [m, 4H, Ar—H], 8.79–8.90 [m, 3H, Ar—H].

Compound (3e) (3-(1-Naphthalenemethoxycarbonyl)-5-nitrophenylboronic acid)

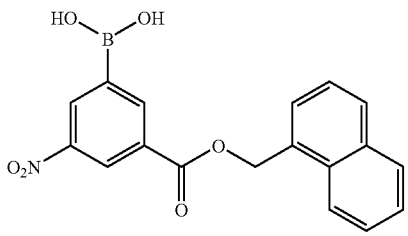

To make compound (3e), 1-Naphthalenemethanol (24 mg, 0.15 mmol) was treated according to general procedure C, step (ii), to give 31 mg (59% yield) of the desired compound as a yellow semisolid. $^1$H-NMR (300 MHz, 5% $D_2O$ in $d_6$-DMSO): δ5.88 [s, 2H, Ar—$CH_2$], 7.50–8.24 [m, 7H, Ar—H], 8.601–8.87 [m, 3H, Ar—H].

Compound (3f) (3-(3-Boronobenzyloxycarbonyl)-5-aminophenylboronic acid)

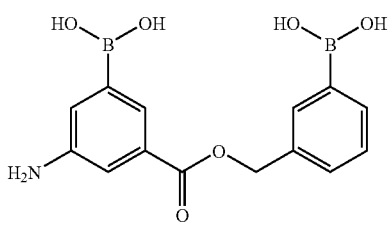

To make the compound (3f), a solution of 3-(3-boronobenzyloxycarbonyl)-5-nitrophenylboronic acid (172 mg, 0.5 mmol) in absolute ethanol (10 ml) was hydrogenated in the presence of Raney Nickel (80 mg) for 4 hours. The catalyst was removed by filtration and the solvent was evaporated to dryness, then the residue was recrystallized from ethanol/$H_2O$ to give 60 mg (38% yield) of the desired compound as a pale yellow semisolid. $^1$H-NMR(300 MHz, 5% $D_2O$ in $d_6$-DMSO): δ5.25 [s, 2H, Ar—$CH_2$], 6.56–6.97 [m, 2H, Ar—H], 7.15–8.09 [m, 5H, Ar—H].

Compound (3g) (3-(3-Boronobenzyloxycarbonyl)-5-hydroxylphenylboronic acid)

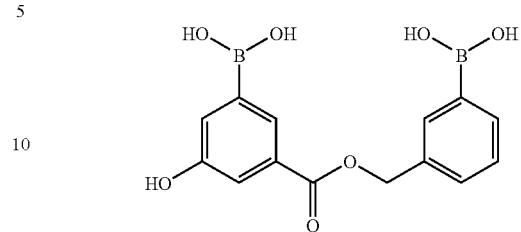

To make the compound (3g), 3-(3-boronobenzyloxycarbonyl)-5-aminophenylboronic acid (31 mg, 0.1 mmol) was suspended in 2 mL of 50% $H_2SO_4$ and treated at −5° C. with a solution of $NaNO_2$ (8 mg, 0.1 mmol) in 1 mL of water. After the mixture had been stirred for 1 h at this temperature, water (10 mL) was added and the mixture was warmed to 60° C. until the evolution of gas ceased. The dark brown solution was extracted twice with ethyl acetate, and the extracts were washed with water and brine and dried with $Na_2SO_4$. The solvent was evaporated to dryness, then the residue was recrystallized from methanol to give 10 mg (32% yield) of the desired compound as a pale yellow powder, mp: 217° C.(dec). $^1$H-NMR(300 MHz, 5% $D_2O$ in $d_6$-DMSO): δ5.39 [s, 2H, Ar—$CH_2$], 7.07–7.64 [m, 3H, Ar—H], 7.89–8.27 [m, 4H, Ar—H].

Example 4

Synthesis of Select Compounds in Formulation A(IV)

Compound (4a)
3-(2-Fluorobenzamido)-5-carboxylphenylboronic acid

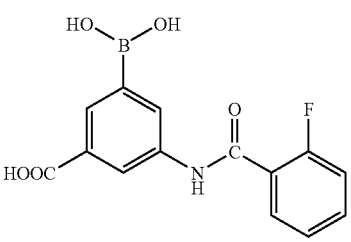

To make compound (4a), 2-fluorobenzoyl chloride (60 μL, 0.5 mmol) was added dropwise over a period of 30 min to an ice-cold solution of 3-amino-5-carboxylphenylboronic acid (91 mg, 0.5 mmol) and $NaHCO_3$ (105 mg, 1.25 mmol) in 10 mL of water. The reaction mixture was kept at 0° C. for 1 h and then stirred at room temperature overnight. It was then extracted twice with 10 mL of ethyl ether. The aqueous solution was acidified with 1N aqueous HCl and extracted twice with 10 mL of ethyl acetate. The combined organic layers were washed with water and saturated brine solution, dried ($Na_2SO_4$) and concentrated. The residue was recrystallized from ethyl acetate/hexane to give 94 mg (62% yield) of the desired compound as a white powder, mp: 224–225° C. $^1$H-NMR(300 MHz, 5% $D_2O$ in $d_6$-DMSO): δ7.21–7.38 [m, 2H, Ar—H], 7.48–7.72 [m, 2H, Ar—H], 8.12–8.33 [m, 3H, Ar—H].

Example 5

Synthesis of Select Compounds in Formulation A(XI)

Compound (5a) (3–5-carboxylphenylboronic acid)

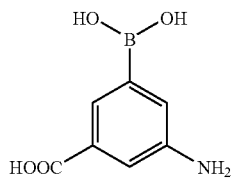

To make the compound (5a), a solution of 3-carboxyl-5-nitrophenylboronic acid (422 mg, 2 mmol) in absolute ethanol (5 ml) was hydrogenated in the presence of Raney Nickel (150 mg) for 6 hours. The catalyst was removed by filtration and the solvent was evaporated to dryness, then the residue was recrystallized from water to give 257 mg (71% yield) of the desired compound as a pale yellow powder, mp: 210–212° C. (Ref. mp: 212–214° C.). $^1$H-NMR(400 MHz, 5% $D_2O$ in $d_6$-DMSO): δ7.06 [s, 1H, Ar—H], 7.16 [s, 1H, Ar—H], 7.55 [s, 1H, Ar—H] (Torssell, K.; Meyer, H.; Zacharias, B. *Arkiv Kemi* 1957, 10, 497–505).

Example 6

Synthesis of Select Compounds in Formulation A(XII)

Compound (6a) (3-(2,6-Dichlorophenylcarbonyloxy)phenyl boronic acid)

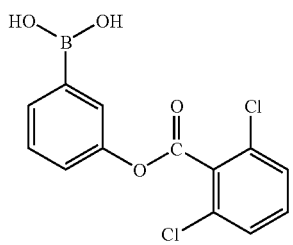

To make compound (6a), a solution of 2,6-dichlorobenzoyl chloride (29 μL, 0.2 mmol) in 5 mL of dried THF was added dropwise to an ice-cold solution of 3-hydroxyphenylboronic acid (21 mg, 0.15 mmol), dried triethyl amine (42 μL, 0.3 mmol) and 10 mL of dried THF. The reaction mixture was stirred at room temperature overnight and then evaporated to dryness. It was dissolved in 25 mL of ethyl acetate and washed with 1N aqueous HCl, 10% aqueous $NaHCO_3$, saturated brine solution, dried ($Na_2SO_4$) and then concentrated. The residue was purified by flash chromatography eluting with MeOH-ethyl acetate (1:10) to give 38 mg (81% yield) of desired compound as a white powder, mp: 238° C.(dec). $^1$H-NMR (400 MHz, 5% $D_2O$ in $d_6$-DMSO): δ7.08–7.19 [m, 1H, Ar—H], 7.22–7.30 [m, 1H, Ar—H], 7.22–7.30 [m, 1H, Ar—H], 7.42–7.50 [m, 1H, Ar—H], 7.54–7.60 [m, 1H, Ar—H], 7.60–7.68 [m, 2H, Ar—H], 7.73–7.78 [m, 3H, Ar—H].

Example 7

Synthesis of Select Compounds in Formulation A(XIII)

Compound (7a) 4-Borono-2-fluorobenzoic acid 2-chloro-1,4-phenylene ester

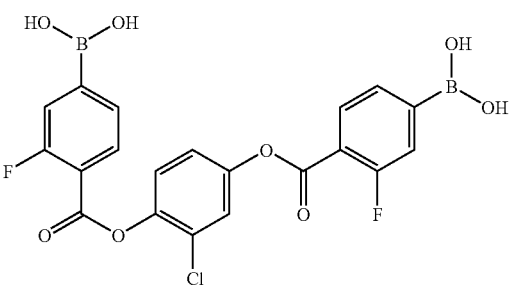

In step (i), oxalyl chloride (35 μL, 0.4 mmol) was added to a suspension of 3-fluoro-4-carboxylphenylboronic acid (37 mg, 0.2 mmol), 1 drop of DMF and 5 mL of dried $CH_2Cl_2$. The reaction mixture was stirred at room temperature overnight and then evaporated to dryness to afford acid chloride as a yellow solid, which was used without further purification in step (ii).

In step (ii), a suspension of the above acid chloride (0.2 mmol, obtained from step (ii)) in 5 mL of dried THF was added dropwise to an ice-cold solution of chlorohydroquinone (11 mg, 0.075 mmol), anhydrous triethyl amine (42 μL, 0.3 mmol) and 10 mL of anhydrous THF. The reaction mixture was stirred at room temperature overnight and then evaporated to dryness. It was dissolved in 25 mL of ethyl acetate and washed with 1N aqueous HCl, 10% aqueous $NaHCO_3$, saturated brine solution, dried ($Na_2SO_4$) and then concentrated. The residue was purified by flash chromatography eluting with MeOH-ethyl acetate (1:10) to give 26 mg (74% yield) of the desired compound as a pale yellow powder, mp: 228–230° C. $^1$H-NMR (400 MHz, 5% $D_2O$ in $d_6$-DMSO): δ6.52–6.55 [m, 1H, Ar—H], 6.68–6.76 [m, 2H, Ar—H], 6.94–7.06 [m, 1H, Ar—H], 7.21–7.34 [m, 1H, Ar—H], 7.57–7.78 [m, 3H, Ar—H], 7.99–8.11 [m, 1H, Ar—H].

Example 8

Synthesis of Select Compounds In Formulation A(XIV)

Compound 8(a) (4-(2-Chloro-6-nitrophenoxycarbonyl)-3-fluorophenylboronic acid)

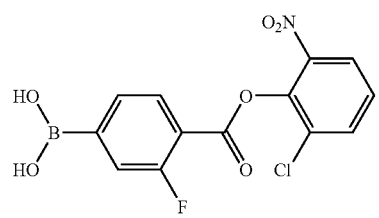

In step (i), oxalyl chloride (35 μL, 0.4 mmol) was added to a suspension of 3-fluoro-4-carboxylphenylboronic acid (37 mg, 0.2 mmol), 1 drop of DMF and 5 mL of dried CH$_2$Cl$_2$. The reaction mixture was stirred at room temperature overnight and then evaporated to dryness to afford acid chloride as a yellow solid, which was used without further purification in step (ii).

In step (ii), a suspension of the above acid chloride (0.2 mmol) in 5 mL of dried THF was added dropwise to an ice-cold solution of 2-chloro-6-nitrophenol (26 mg, 0.15 mmol), dried triethyl amine (42 µL, 0.3 mmol) and 10 mL of dried THF. The reaction mixture was stirred at room temperature overnight and then evaporated to dryness. It was dissolved in 25 mL of ethyl acetate and washed with 1N aqueous HCl, 10% aqueous NaHCO$_3$, saturated brine solution, dried (Na$_2$SO$_4$) and concentrated. The residue was purified by flash chromatography eluting with MeOH-ethyl acetate (1:10) to give 40 mg (79% yield) of the desired compound as a pale yellow powder, mp: 174–175C. $^1$H-NMR (400 MHz, 5% D$_2$O in d$_6$-DMSO): δ7.61–7.36 [m, 1H, Ar—H], 7.71–7.74 [m, 1H, Ar—H], 7.77–7.79 [m, 1H, Ar—H], 8.07–8.11 [m, 2H, Ar—H], 8.18–8.21 [m, 2H, Ar—H].

Example 9

Synthesis of Select Compounds In Formulation A(XV)

Compound (9a) (3-Borono-5-nitrobenzoic acid 1,3-phenylene ester)

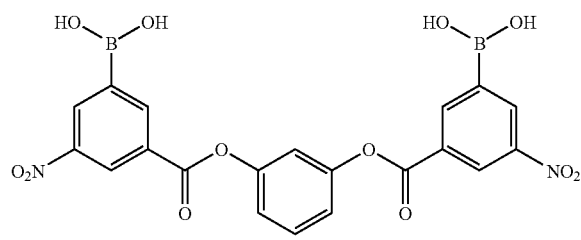

In step (i), oxalyl chloride (35 µL, 0.4 mmol) was added to a suspension of 3-carboxyl-5-nitrophenylboronic acid (42 mg, 0.2 mmol), 1 drop of DMF and 5 mL of dried CH$_2$Cl$_2$. The reaction mixture was stirred at room temperature overnight and then evaporated to dryness to afford acid chloride as a yellow solid, which was used without further purification in step (ii).

In step (ii), a solution of the above acid chloride (0.2 mmol) in 5 mL of dried THF was added dropwise to an ice-cold solution of resorcinol (9 mg, 0.075 mmol), dried triethyl amine (42 µL, 0.3 mmol) and 10 mL of dried THF. The reaction mixture was stirred at room temperature overnight and then evaporated to dryness. It was dissolved in 25 mL of ethyl acetate and washed with 1N aqueous HCl, 10% aqueous NaHCO$_3$, saturated brine solution, dried (Na$_2$SO$_4$) and concentrated. The residue was purified by flash chromatography eluting with MeOH-ethyl acetate (1:10) to give 26 mg (70% yield) of the desired compound as a pale yellow powder, mp: 134° C.(dec). $^1$H-NMR (400 MHz, 5% D$_2$O in d$_6$-DMSO): δ6.14–6.18 [m, 2H, Ar—H], 7.33–7.45 [m, 2H, Ar—H], 8.75–8.82 [m, 2H, Ar—H], 8.85–8.90 [m, 4H, Ar—H].

Example 10

Synthesis of Select Compounds In Formulation A(XVI)

Compound (10a) (3-Borono-5-nitrobenzoic acid 1,2-benzenedimethanol ester)

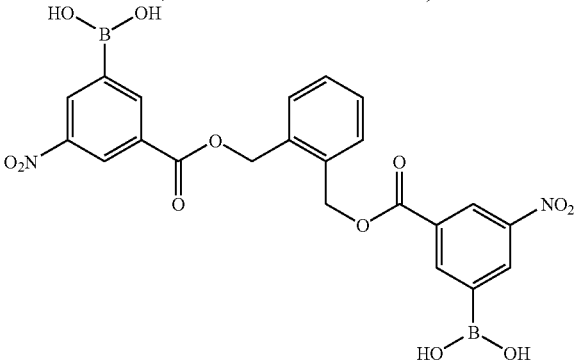

In step (i), oxalyl chloride (35 µL, 0.4 mmol) was added to a suspension of (3-carboxyl-5-nitrophenyl)boronic acid (42 mg, 0.2 mmol), 1 drop of DMF and 5 mL of dried CH$_2$Cl$_2$. The reaction mixture was stirred at room temperature overnight and then evaporated to dryness to afford acid chloride as a yellow solid, which was used without further purification in step (ii).

In step (ii), a suspension of the above acid chloride (0.2 mmol, obtained from step (ii)) in 5 mL of dried THF was added dropwise to an ice-cold solution of 1,2-benzenedimethanol (10 mg, 0.075 mmol), anhydrous triethyl amine (42 µL, 0.3 mmol) and 10 mL of anhydrous THF. The reaction mixture was stirred at room temperature overnight and then evaporated to dryness. It was dissolved in 25 mL of ethyl acetate and washed with 1N aqueous HCl, 10% aqueous NaHCO$_3$, saturated brine solution, dried (Na$_2$SO$_4$) and then concentrated. The residue was purified by flash chromatography eluting with MeOH-ethyl acetate (1:10) to give 21 mg (53% yield) of the desired compound as a pale yellow powder, mp: 142° C.(dec). $^1$H-NMR (400 MHz, 5% D$_2$O in d$_6$-DMSO): δ5.64 [s, 4H, CH$_2$], 6.14–6.18 [m, 2H, Ar—H], 7.33–7.45 [m, 2H, Ar—H], 8.77–8.84 [m, 2H, Ar—H], 8.87–8.93 [m, 4H, Ar—H].

Example 11

Synthesis of Select Compounds in Formulation A(XVII)

Compound (11a) (1,4-Benzenedicarboxylic Acid, di 3-boronophenyl ester)

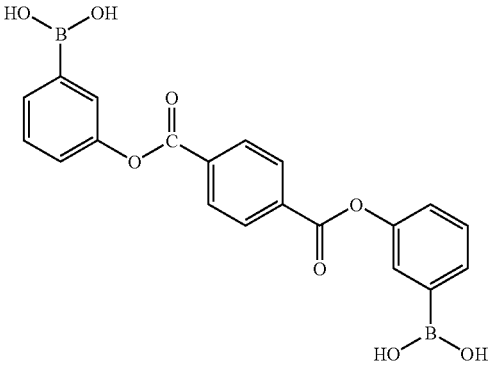

To make compound (12a), a solution of terephthaloyl chloride (21 mg, 0.1 mmol) in 5 mL of dried THF was added dropwise to an ice-cold solution of 3-hydroxyphenylboronic acid (21 mg, 0.15 mmol), dried triethyl amine (28 µL, 0.2 mmol) and 10 mL of dried THF. The reaction mixture was stirred at room temperature overnight and then evaporated to dryness. It was dissolved in 25 mL of ethyl acetate and washed with 1N aqueous HCl, 10% aqueous NaHCO$_3$, saturated brine solution, dried (Na$_2$SO$_4$) and then concentrated. The residue was purified by flash chromatography eluting with MeOH-ethyl acetate (1:10) to give 16 mg (51% yield) of the desired compound as a white powder, mp: 214° C.(dec). $^1$H-NMR (400 MHz, 5% D$_2$O in d$_6$-DMSO): δ7.28–7.34 [m, 2H, Ar—H], 7.38–7.46 [m, 2H, Ar—H], 7.59–7.63 [m, 2H, Ar—H], 7.68–7.73 [m, 2H, Ar—H], 8.30 [s, 4H, Ar—H].

Example 12

Synthesis of Select Compounds In Formulation A(XVIII)

Compound (12a) (Tris(3-borono-5-nitrobenzoic acid), 1,3,5-trihydroxybenzene ester)

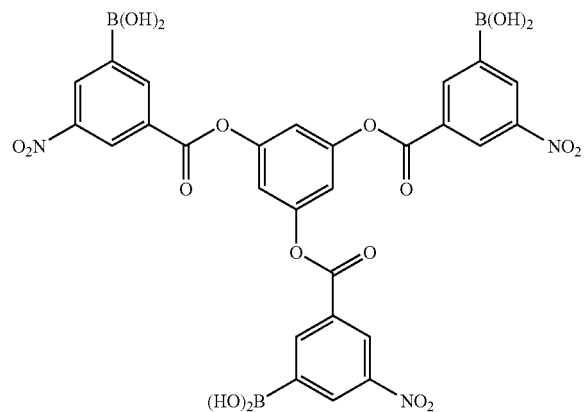

In step (i), oxalyl chloride (79 μL, 0.9 mmol) was added to a suspension of (3-carboxyl-5-nitrophenyl)boronic acid (95 mg, 0.45 mmol), 1 drop of DMF and 10 mL of dried CH$_2$Cl$_2$. The reaction mixture was stirred at room temperature overnight and then evaporated to dryness to afford acid chloride as a yellow solid, which was used without further purification in step (ii).

In step (ii), a suspension of the above acid chloride (0.2 mmol, obtained from step (ii)) in 5 mL of dried THF was added dropwise to an ice-cold solution of phloroglucinol (13 mg, 0.1 mmol), anhydrous triethyl amine (42 μL, 0.3 mmol) and 10 mL of anhydrous THF. The reaction mixture was stirred at room temperature overnight and then evaporated to dryness. It was dissolved in 25 mL of ethyl acetate and washed with 1N aqueous HCl, 10% aqueous NaHCO$_3$, saturated brine solution, dried (Na$_2$SO$_4$) and then concentrated. The residue was purified by flash chromatography eluting with MeOH-ethyl acetate (1:10) to give 17 mg (24% yield) of the desired compound as a pale yellow powder, mp: 274° C.(dec). $^1$H-NMR (400 MHz, 5% D$_2$O in d$_6$-DMSO): δ7.46 [s, 1H, Ar—H], 8.72–8.76 [m, 1H, Ar—H], 8.78–8.86 [m, 2H, Ar—H].

Example 13

Inhibition Assay

The inhibition of TEM-1 β-lactamase was determined spectrophotometrically. B-lactamase activity was followed by measuring the hydrolysis of nitrocefin, [3-(2,4-dinitrostyryl)-(6R, 7R)-7-(2-thienylacetamido)-ceph-3-em-4-carboxylic acid, E-isomer], (Calbiochem, San Diego, Calif., USA) at 486 nm. Inhibition assays were performed at 25° C. in 50 mM sodium phosphate, 5% DMSO, pH 7.0. The enzyme concentration was held at 5 nM, with substrate at 167 μM and varying inhibitor concentrations. Inhibitor was added to the enzyme and incubated for ten minutes before the addition of substrate. Inhibition constants (K$_i$) for the inhibitors are obtained at the desired temperature and solvent conditions by measuring the rate of substrate hydrolysis at increasing amounts of inhibitors.

Table 11 shows the β-lactamase inhibition data of the compounds of the present invention obtained using inhibition assay described above. The Ki values in the parenthesis obtained from a Lineweaver-Burke analysis.

TABLE 11

Results of TEM-1 β-Lactamase Inhibition Assay

| Compound | Ki(μM) (Ki from Lineweaver-Burke Analysis) |
|---|---|
| (1a) | 80 ± 9 |
| (1b) | 12 ± 3 |
|  | (1.18) |
| (1c) | 39 ± 7 |
| (1d) | 42 ± 7 |
| (1e) | >1000 |
| (1f) | 33 ± 4 |
| (1g) | 37 ± 3 |
|  | (1.37) |
| (1h) | 9.5 ± 0.8 |
|  | (0.65) |
| (1i) | 101 ± 4 |
| (1j) | 28 ± 2 |
|  | (1.31) |
| (1k) | 130 ± 18 |
| (1l) | 116 ± 7 |
| (1m) | 114 ± 12 |
| (2a) | 22.7 ± 1.3 |
| (2b) | 15.2 ± 1.4 |
| (1n) | 8.8 ± 0.5 |
|  | (0.62) |
| (1o) | 49.3 ± 4.6 |
| (1p) | 19.8 ± 1.3 |
| (4a) | 143 ± 9 |
| (1q) | 100 ± 8 |
| (3a) | 34 ± 2.9 |
|  | (4.97) |
| (1r) | 138 ± 2.7 |
| (5a) | 727 ± 49 |
| (1s) | 42.3 ± 2.4 |
| (1t) | 95 ± 8.7 |
|  | (6.54) |
| (3b) | 27 ± 3.4 |
|  | (2.76) |
| (3c) | 25 ± 1.5 |
|  | (2.35) |
| (1u) | 25 ± 2.5 |
|  | (1.68) |
| (6a) | 28 ± 2.1 |
| (1v) | 32 ± 1.1 |
| (3d) | 55.7 ± 4.3 |
| (7a) | 122 ± 10 |
| (8a) | 43 ± 1.6 |
| (9a) | 16 ± 1.5 |
| (1w) | 13 ± 1.1 |
| F1001 | 104 |
| F1002 | 148 |
| F1012 | 113 |
| F1201 | 27 |
| F1212 | 95 |
| BB-1003 | 231 |
| BB-1004 | 297 |
| BB-1005 | 392 |

Example 14

Binding Energetics of Inhibitors

The binding of the compounds of the present invention to β-lactamase was also measured by isothermal titration calorimetry. Isothermal titration calorimetry does not only measure the binding affinity of inhibitors but also dissects the enthalpic and entropic components to binding, thus allowing identification of the forces involved in the association reaction. In general a binding reaction characterized by a favorable enthalpy change indicates that the inhibitor establishes strong interactions with the target, whereas an inhibitor characterized by unfavorable binding enthalpy is driven by non-specific hydrophobic interactions, i.e., a tendency to escape water rather than a strong attraction to the target (Velazquez-Campoy et al., (2001) Arch. Biochim. Biophys. 390, 169–175; and Ohtaka et al., (2002) Protein Science 11, 1908–1916).

TABLE 12

Binding Enthalpy of Selected Compounds

| Compound | ΔH wt cal/mol | ΔH M69I cal/mol | ΔH E104K cal/mol | ΔH R244S cal/mol |
|---|---|---|---|---|
| (1b) | −3800 | −2000 | −3900 | −9500 |
| F1201 | −3200 | −2400 | −3500 | −6500 |
| F1212 | −4700 | −3300 | −4500 | −8900 |
| (1h) | −1140 | −953 | −1896 | −11931 |
| (1j) | −2145 | −1693 | −2756 | −6877 |
| (1g) | −5520 | −2460 | −6397 | −8200 |

These experiments, in combination with the inhibition assays, indicate that the compounds identified in this disclosure bind to the wild type as well as drug resistant beta lactamases with favorable binding enthalpies. This is a very important characteristic from the point of view of further optimization since it facilitates the achievement of extremely high affinities and low susceptibilities to drug resistant mutations and naturally occurring polymorphisms.

Example 15

Activity Against Clavulanic Acid Resistant Mutants

As discussed above, the use of β-lactam-based β-lactamase inhibitors has led to the appearance of infectious microorganisms that carry mutated versions of the beta lactamase enzyme that are not efficiently inhibited by beta lactamase inhibitors currently in clinical use (clavulanic acid, sulbactam, tazobactam) (Bonomo et al, 1997). Three of the most important mutations are M69I, R244S and E104K. The mutations M69I and R244S significantly lower the affinity of clinically used beta lactamase inhibitors whereas the mutation E104K does not have a direct effect on the affinity of those molecules but increases the hydrolysis rates of extended spectrum antibiotics. Compounds of the present invention were tested against these mutations as shown in Table 13. As shown in Table 13, while the existing clinical inhibitors lose potency between one to over two orders of magnitude, compounds of the present invention maintain equivalent potency against wild type and drug resistant mutants, and in many cases exhibit better potency against drug resistant mutants.

TABLE 13

Loss of Potency Against β-Lactamase Mutants Expressed as the Ratio of the Inhibitory Constant Between Mutant and Wild Type ($Potency_{wt}/Potency_{mutant}$).*

| Compound | M69I | R244S | E104K |
|---|---|---|---|
| Clavulanic | 163 | 38 | 0.67 |
| Sulbactam | 15 | 93 | 1 |
| Tazobactam | 31 | 105 | 1 |
| (1h) | 1.2 | 0.86 | 0.77 |
| (1b) | 1.0 | 1.2 | 0.92 |
| F1201 | 0.52 | 0.86 | 0.48 |
| (1j) | 0.33 | 0.37 | 0.15 |
| (1f) | 0.47 | 0.42 | 0.37 |
| (1g) | 0.40 | 0.26 | 0.32 |
| (1d) | 0.60 | 0.62 | 0.55 |
| (1c) | 1.0 | 0.52 | 0.56 |
| (1a) | 0.43 | 0.44 | 0.39 |
| (1i) | 0.50 | 0.34 | 0.36 |

*A number higher than 1 reflects a loss of potency against mutant

Example 16

Recovery of Antibiotic Potency in Antibacterial Assay

The following four compounds

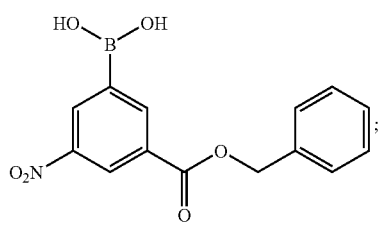
(compound F1201)

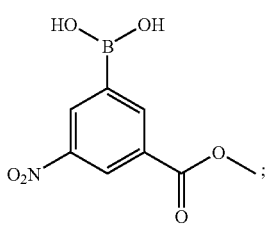
(compound F1202)

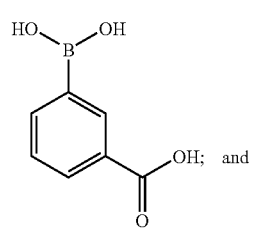
(compound F1203)

and

-continued (compound F1204)

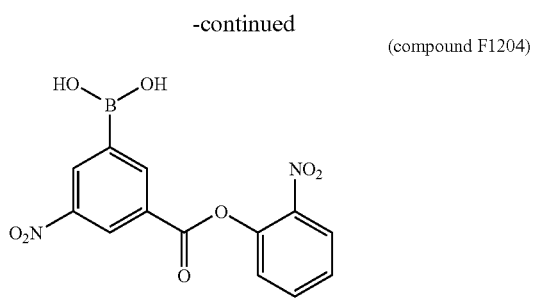

were tested against three different strains:

(1) methicillin resistant *S. aureus* ATCC 33591 (MRSA-ATCC). This strain was obtained from American Type Culture Collection (ATCC), Manassas, Md.;

(2) methicillin resistant *S. aureus* from Stanford University Hospital Clinical Microbiology/Virology Laboratory (MRSA-SU). This strain was isolated from a blood culture and was found to be resistant to nafcillin and oxacillin. Such *Staphylococci* are also resistant to all penicillins, and all cephalosporins, in addition to all β-lactamase inhibitor combinations (including ampicillin/sulbactarn, amoxicillin/clavulanic acid, piperacillin/tazobactam), imipenem, and meropenem; and (3) methicillin sensitive *S. aureus* ATCC 25923 (MSSA). This strain was obtained from ATCC and was used as a control.

Oxacillin (Lot # 11OK1041) was purchased from Sigma Chemical Company, St. Louis, Mo.

Experimental Procedures

Cultivation and Maintenance of Test Organisms

The strains were processed according to procedures recommended by ATCC, or procedures that are routinely used. Single colonies of each organism were picked for purification to generate pure working cultures. Prior to each experiment each strain was subcultured on a fresh Mueller-Hinton agar plate (MHA).

Inoculum

Inocula for the MIC assays were prepared by transferring a tiny portion of one colony from a MHA plate to 2 ml of Mueller-Hinton broth (MHB) such that the estimated cell density was about $10^7$ colony forming unit (CFU)/ml. This cell suspension was then further diluted 10-fold (to $10^6$ CFU/ml) by transferring the 2 ml cell suspension to 18 ml of MHB. Addition of 50 µl of this dilute cell suspension to 50 µl of growth medium yielded the desired cell density, namely about $5 \times 10^4$ CFU/well, or $5 \times 10^5$ CFU/ml.

Broth Microdilution Procedure

The MIC value of oxacillin was determined using the broth microdilution procedure recommended by the National Committee of Clinical Laboratory Standards (NCCLS, 2000). This procedure was also used to determine whether any of the inhibitors exhibited antimicrobial activity.

MIC Assays with Oxacillin

The MIC experiments were performed in duplicate in 96-well microtiter plates using MHB. A stock solution of 2.6 mg/0.5 ml was prepared in dimethylsulfoxide (DMSO). A total of 8 two-fold serial dilutions were made with DMSO. Initial oxacillin doses used were (µg/ml): 64, 32, 16, 8, 4, 2, 1, and 0.5. Doses were adjusted in the confirmatory experiment, if needed, in order to establish an actual MIC value.

To each well of a 96 well microtiter plate was added 47.5 µl of MHB. A volume of 2.5 µl of each dilution of oxacillin was then transferred to appropriate wells containing the medium. All wells, except the sterility control wells, were then inoculated with 50 µl of a diluted cell suspension to give a final volume of 100 µl and a final cell density of $5 \times 10^4$ CFU/well. The volume in the sterility control wells was adjusted to 100 µl with MHB. A sterile pipette tip was used to mix the contents of each well (one tip was used going from the low to the high concentration in the same column). The microtiter plates were covered with the lids and were placed in large Stratagene Big Blue plates (Cat. # 400041). Four large kimwipes moistened with tap water were placed near the edges of the Stratagene plates to prevent evaporation of the medium. The microtiter plates were incubated for at least 24 hours at 35° C. The plates were then evaluated for growth in each well. Controls included: medium sterility and negative control (medium and bacteria only).

MIC Assays with Compounds of the Present Invention

The procedure used to determine the antimicrobial activity of the compounds of the present invention was identical to the broth microdilution procedure described above with the exception of the preparation of the stock solutions. Stock solution at concentration of 40.96 mg/0.5 ml was prepared in DMSO for each of the compounds. A total of 8 two-fold dilutions were then made in DMSO. A volume of 2.5 µl of each dilution was delivered to appropriate wells. The initial doses used were (µg/ml): 512, 256, 128, 64, 32, 16, 8, and 4.

Criteria for MIC determination

A numerical code was used to evaluate the extent of growth as indicated below.

0: absence of growth
1: barely visible (faint) growth
2: fair growth but less than the negative solvent control
3: growth is equivalent to the negative solvent control.

The lowest dose at which no visible growth is observed was determined to be the MIC value.

Matrix System

The effect of the four compounds of the present invention on oxacillin resistance of the MRSA strains was determined using a matrix system. The β-lactamase inhibitors were tested at 5 doses against up to eleven concentrations of oxacillin. The highest dose of oxacillin and inhibitors used were at least one dose above the MIC value, with the exception of compound FL203 which was tested at a high dose of 512 µl/ml which was not bacteriotoxic to any of the strains used. A 96-well microtiter plate was used for the matrix system. The procedure was identical to that described above for the MIC determination, with the exception that both oxacillin and one each of the β-lactamase inhibitors was added, 2.5 µl each, to the wells prior to addition of the test organisms.

Results and Discussion

MIC Evaluation of Oxacillin and the Four Compounds

MIC assays were performed with oxacillin and the four compounds. Each of the compounds was tested at the following 8 doses (µg/ml): 512, 256, 128, 64, 32, 16, 8, and 4. Oxacillin was tested at the following 8 doses (µg/ml): 64, 32, 16, 8, 4, 2, 1, and 0.5. The MIC values obtained were tabulated in Table 14. These MIC data indicate that these four compounds have antibacterial activities.

TABLE 14

| Test Organism | Compound F1201 | Compound F1202 | Compound F1203 | Compound F1204 | Oxacillin |
|---|---|---|---|---|---|
| MRSA-ATCC | 32 | 16 | >512 | 256 | 32 |
| MSSA | 32 | 128 | >512 | 512 | 0.25 |
| MRSA-SU | 32 | 256 | >512 | 512 | >64 |

Matrix Study:Oxacillin and Compound FL201 with MRSA-ATCC

The results are shown in Table 15.

TABLE 15

| Oxacillin | Compound F1201 | | | | |
|---|---|---|---|---|---|
| µg/ml | 0 | 16 | 8 | 4 | 2 | 1 |
| 0 | 3 | 0 | 1 | 2 | 3 | 3 |
| 64 | 0 | 0 | 0 | 0 | 0 | 0 |
| 32 | 2 | 0 | 0 | 0 | 0 | 0 |
| 16 | 2 | 0 | 0 | 0 | 0 | 0 |
| 8 | 3 | 0 | 0 | 0 | 0 | 1 |
| 4 | 3 | 0 | 0 | 0 | 0 | 1 |
| 2 | 3 | 0 | 0 | 0 | 0 | 1 |
| 1 | 3 | 0 | 0 | 0 | 1 | 1 |
| 0.5 | 3 | 0 | 0 | 0 | 1 | 1 |
| 0.25 | 3 | 0 | 0 | 1 | 1 | 1 |
| 0.125 | 3 | 0 | 0 | 1 | 1 | 1 |
| 0.064 | 3 | 0 | 0 | 1 | 1 | 1 |
| MIC µg/ml | 64 | N/A | <0.064 | 0.5 | 2 | 16 |

Matrix Study: Oxacillin and Compound Fl202 with MRSA-ATCC

The results are shown in Table 16.

TABLE 16

| Oxacillin | Compound F1202 | | | | |
|---|---|---|---|---|---|
| µg/ml | 0 | 16 | 8 | 4 | 2 | 1 |
| 0 | 3 | 1 | 1 | 2 | 2 | 3 |
| 64 | 0 | 0 | 0 | 0 | 0 | 0 |
| 32 | 2 | 0 | 0 | 0 | 0 | 0 |
| 16 | 2 | 0 | 0 | 0 | 0 | 2 |
| 8 | 3 | 0 | 0 | 0 | 1 | 2 |
| 4 | 3 | 0 | 0 | 0 | 2 | 2 |
| 2 | 3 | 0 | 0 | 0 | 2 | 2 |
| 1 | 3 | 0 | 0 | 0 | 2 | 3 |
| 0.5 | 3 | 0 | 0 | 1 | 2 | 3 |
| 0.25 | 3 | 0 | 0 | 1 | 2 | 3 |
| 0.125 | 3 | 0 | 0 | 2 | 3 | 3 |
| 0.064 | 3 | 0 | 1 | 2 | 3 | 3 |
| MIC µg/ml | 32 | <0.064 | 0.125 | 1 | 16 | 32 |

Matrix Study:Oxacillin and Compound FL201 with MRSA-SU

The results are shown in Table 17.

TABLE 17

| Oxacillin | Compound F1201 | | | | |
|---|---|---|---|---|---|
| µg/ml | 0 | 32 | 16 | 8 | 4 | 2 |
| 0 | 3 | 0 | 1 | 2 | 2 | 3 |
| 256 | 0 | 0 | 0 | 0 | 0 | 0 |
| 128 | 1 | 0 | 0 | 0 | 0 | 0 |
| 64 | 2 | 0 | 0 | 0 | 0 | 0 |
| 16 | 3 | 0 | 0 | 0 | 0 | 1 |
| 4 | 3 | 0 | 0 | 0 | 1 | 1 |
| 2 | 3 | 0 | 0 | 0 | 1 | 1 |
| 1 | 3 | 0 | 0 | 0 | 1 | 1 |
| 0.5 | 3 | 0 | 0 | 0 | 1 | 2 |
| 0.25 | 3 | 0 | 0 | 1 | 1 | 2 |
| 0.125 | 3 | 0 | 0 | 1 | 2 | 2 |
| 0.064 | 3 | 0 | 0 | 1 | 2 | 2 |
| MIC µg/ml | 256 | N/A | <0.064 | 0.5 | 16 | 64 |

Matrix Study: Oxacillin and Compound FL202 with MRSA-SU

The results are shown in Table 18.

TABLE 18

| Oxacillin | Compound F1202 | | | | |
|---|---|---|---|---|---|
| µg/ml | 0 | 256 | 128 | 64 | 32 | 16 |
| 0 | 3 | 0 | 1 | 3 | 3 | 3 |
| 256 | 0 | 0 | 0 | 0 | 0 | 0 |
| 128 | 2 | 0 | 0 | 0 | 0 | 0 |
| 64 | 2 | 0 | 0 | 0 | 0 | 0 |
| 16 | 3 | 0 | 0 | 0 | 0 | 1 |
| 4 | 3 | 0 | 0 | 0 | 0 | 1 |
| 2 | 3 | 0 | 0 | 0 | 1 | 1 |
| 1 | 3 | 0 | 0 | 0 | 1 | 1 |
| 0.5 | 3 | 0 | 0 | 1 | 1 | 1 |
| 0.25 | 3 | 0 | 0 | 1 | 1 | 1 |
| 0.125 | 3 | 0 | 1 | 1 | 1 | 1 |
| 0.064 | 3 | 0 | 1 | 1 | 1 | 1 |
| MIC µg/ml | 256 | N/A | 0.25 | 1 | 4 | 64 |

Example 17

Comparison of Activities Against TEM-1 and Amp-C β-Lactamases

Materials and Methods

The gene for AmpC β-lactamase (accession number P00811) was obtained from *Escherichia coli* K12 strain W3110 (American Type Culture Collection, Rockville Md.). *E. coli* was grown and plasmid (F-lacIq lacPL8 ampC:: lambdacI+) was isolated via Qiagen (Valencia, Calif.) mini prep. The gene for AmpC was amplified in two pieces via polymerase chain reaction, ligated and purified by agarose gel electrophoresis. The ligated gene was inserted into a pET200 vector via a TOPO reaction (Invitrogen, Carlsbad, Calif.). Correct gene and plasmid sequence was verified by standard DNA sequencing.

BL21 (DE3) (Invitrogen) cells were transformed by heat-shock with the prepared plasmid. These cells were grown to an $OD_{600}$ of 0.8 at 37° C. Isopropylthiogalactoside (IPTG) was added to 1 mM, incubation temperature decreased to 25° C. and the cells were grown for an additional 18 hours. After 18 hours, the *E. coli* was pelleted by centrifugation, and discarded. The growth media was concentrated and dialyzed versus 100 mM Tris, pH 7.0. This solution was run through an equilibrated Q-resin column, and washed with excess 100 mM Tris, pH 7.0. AmpC was eluted and purity was found to be >95% by SDS-PAGE.

The competitive inhibition of β-lactamase was determined spectrophotometrically using a Varian (Walnut Creek, Calif.) Cary 100 UV-Visible spectrophotometer. β-lactamase activity was followed by measuring the hydrolysis of nitrocefin, [3-(2,4-dinitrostyryl)-(6R, 7R)-7-(2-thienylacetamido)-ceph-3-em-4-carboxylic acid, E-isomer], (Calbiochem, San Diego, Calif.) at 486 nm. Inhibition assays were performed at 25° C. in 50 mM sodium phosphate, 5% DMSO, pH 7.0. Typical β-lactamase preparations hydrolyze nitrocefin substrate from 50 to 150 $s^{-1}$. Under these conditions, the $K_M$ for AmpC β-lactamase is 250 µM and the $k_{cat}$ is 975 $s^{-1}$. Penicillin G (Sigma, St. Louis, Mo.) was also used as a substrate to determine $K_M$ and $k_{cat}$.

Lineweaver-Burk plots were used to determine the inhibition mechanism, and several compounds were found to inhibit competitively. For determination of compound inhibition constants, protein was held at 5 nM, with nitrocefin substrate at 167 µM and a varying inhibitor concentration. Inhibitor was added to protein and incubated for ten minutes before the addition of substrate. Inhibition constants were determined by measuring the loss of P-lactamase activity with increasing inhibitor concentrations and fitting the data to standard equations for competitive inhibition.

Isothermal titration calorimetry was performed on a high-precision VP-ITC titration calorimeter (Microcal Inc., Northampton, Mass.). β-Lactamase solutions were titrated with inhibitors in 50 mM sodium phosphate, 2% DMSO, pH 7.0, with β-lactamase concentrations ranging from 15 to 25 µM and inhibitor concentrations ranging from 300 to 1000 µM. The heat evolved from each injection was obtained by integrating the calorimetric signal. Heat of binding was obtained as the difference between the heat of reaction and the heat of inhibitor dilution. Data were analyzed using Origin 7.0 (OriginLab Corporation, Northampton, Mass.).

These methods can also be used to express and assay recombinant TEM-1 variant of β-lactamase.

Results

Kinetic measurements of the digestion of a natural substrate, penicillin G and a chemically available substrate, nitrocefin are shown in Table 19. $k_{cat}/K_M$, a measure of the catalytic efficiency, is larger with penicillin G as a substrate instead of nitrocefin.

TABLE 19

Kinetic characterization of the AmpC β-lactamase.

| Substrate | $k_{cat}{}^1$ | $K_M{}^2$ | $k_{cat}/K_M{}^3$ |
|---|---|---|---|
| penicillin G | 198 ± 4 | 28 ± 3 | 7.2 ± 0.6 |
| nitrocefin | 976 ± 46 | 253 ± 28 | 3.9 ± 0.6 |

[1]Units are $s^{-1}$.
[2]Units are µM.
[3]Units are $s^{-1} \mu M^{-1}$.

Phenyl-boronic acids have inhibitory activity against the TEM-1 and AmpC β-lactamases. Lineweaver-Burk inhibition plots indicate competitive inhibition. Screening of compounds for inhibitory activity showed several compounds with inhibitory activity in the high nanomolar to low micromolar range. Isothermal titration calorimetry was undertaken to determine the thermodynamic characteristics of binding to AmpC β-lactamase. Most compounds tested bound with favorable enthalpic contributions, although the magnitude of the enthalpic contribution varied greatly between the compounds. Several compounds bound with nM affinity.

The compounds with the highest inhibitory activity and the thermodynamic components of binding to Amp-C are shown in Table 20. Also shown are the results obtained for β-lactamase variant TEM-1.

TABLE 20

Inhibition constants and thermodynamic parameters of compounds versus AmpC and TEM-1 β-lactamases

| AmpC | $Ki^1$ | $\Delta G^2$ | $\Delta H^2$ | $-T\Delta S^2$ | TEM-1 | $Ki^1$ | $\Delta G^2$ | $\Delta H^2$ | $-T\Delta S^2$ |
|---|---|---|---|---|---|---|---|---|---|
| (10a) | 0.457 | −8590 | −4149 | −4441 | (2c) | 6.7 | −5814 | −1648 | −4166 |
| (3f) | 0.724 | −8151 | −9325 | 1174 | (12a) | 6.9 | −6468 | −690 | −5778 |
| (7a) | 0.873 | −7314 | −9936 | 2622 | (1n) | 8.8 | −5608 | −1173 | −4435 |
| (8a) | 0.913 | −8190 | −8486 | 296 | (1h) | 9.5 | −6614 | −1140 | −5474 |
| (3d) | 1.03 | −7442 | −15637 | 8195 | (10a) | 9.7 | −7183 | −982 | −6201 |
| (11a) | 1.31 | −7548 | −3114 | −4434 | (1x) | 10.4 | −6655 | −577 | −6078 |
| (6a) | 1.53 | −7757 | −6538 | −1219 | (2d) | 10.9 | −6513 | −859 | −5654 |
| F1001 | 1.79 | −6830 | −644 | −6186 | (1b) | 12 | −6420 | −4011 | −2409 |
| (12a) | 1.94 | −7231 | −1470 | −5761 | (1w) | 12.7 | −6409 | −4554 | −1855 |
| (3g) | 2.69 | −7356 | −3677 | −3679 | (2b) | 15.2 | −7864 | −520 | −7344 |
| (2b) | 2.92 | −7736 | −225 | −7511 | (1y) | 15.8 | −6550 | 0 | −6550 |
| (2c) | 3.68 | −7115 | −473 | −6642 | (9a) | 16.2 | −7864 | 446 | −8310 |
| F1201 | 4.45 | −6566 | −5084 | −1482 | (3e) | 17.1 | −6164 | 224 | −6388 |
| (1v) | 5.01 | −7221 | −10412 | 3191 | (1p) | 19.8 | −5916 | −6715 | 799 |
| (2d) | 6.27 | −7098 | 0 | −7098 | (2a) | 22.7 | −7451 | 274 | −7725 |

[1]Ki units are µM.
[2]ΔG, ΔH and −TΔS units are cal/mol.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

Numerous references, including patents, patent applications, protocols and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entirety and to the same extent as if each reference was individually incorporated by reference.

What is claimed is:

1. A compound represented by formula A(II):

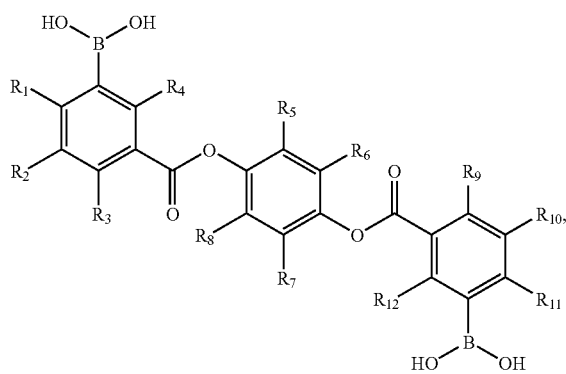

A(II)

wherein $R_1$ through $R_{12}$ are each independently hydrogen, $C_{1-6}$ alkyl, $C_{3-6}$ cycloalkyl, $C_{1-3}$ alkoxy, n-butoxy, i-butoxy, sec-butoxy, $R_{13}R_{14}N$— (wherein $R_{13}$ and $R_{14}$ are each independently hydrogen or $C_{1-3}$ alkyl), trifluoromethyl, trifluoromethoxy, difluoromethoxy, fluoro, chloro, bromo, cyano, acetyl, amino, borono, nitro, carboxyl, $C_{1-6}$ alkoxycarbonyl, phenyl, phenoxy, phenoxycarbonyl, benzyloxy, hydroxyl, trimethylsilyloxy, diphenyl-t-butylsilyloxy, hydroxymethyl, —SO$_3$H, —SO$_2$CH$_3$, —SO$_2$NHR$_{15}$ (wherein $R_{15}$ is hydrogen or $C_{1-3}$ alkyl), or —O(CH$_2$)$_n$OR$_{16}$— (wherein $R_{16}$ is hydrogen or $C_{1-3}$ alkyl, and n is 1, 2 or 3); or when any two $R_i$s are located at the ortho position to each other, they together form $-Z_1=Z_2-Z_3=Z_4$- (wherein $Z_1$ through $Z_4$ each independently represents CH or N), —S—CO—O—, —CH=CH—NH—, —CH=CH—S—, —CH=CH—O—, —N=CH—NH—, —CH$_2$—N=N—, —N=N—O—, —N=CH—S— or —O—CH$_2$CH$_2$—O—.

2. The compound of claim 1, wherein
$R_1$, $R_3$, $R_4$, $R_9$, $R_{11}$ and $R_{12}$ are each hydrogen;
$R_2$ and $R_{10}$ are each independently hydrogen, fluoro, chloro, bromo, cyano, acetyl, nitro, amino, borono, carboxyl, $C_{1-4}$ alkoxycarbonyl, phenoxycarbonyl, hydroxyl, —SO$_3$H, —SO$_2$CH$_3$ and —SO$_2$NH$_2$;
$R_5$ through $R_8$ are each independently hydrogen, $C_{1-4}$ alkyl, $C_{3-6}$ cycloalkyl, $C_{1-3}$ alkoxy, trifluoromethyl, fluoro, chloro, bromo, cyano, acetyl, amino, borono, nitro, carboxyl, $C_{1-4}$ alkoxycarbonyl, phenyl, phenoxy, phenoxycarbonyl, benzyloxy, hydroxyl, hydroxymethyl, —SO$_3$H, —SO$_2$CH$_3$, —SO$_2$NH$_2$, or when any two $R_i$s are located at the ortho position to each other, they together form $-Z_1=Z_2-Z_3=Z_4$- (wherein $Z_1$ through $Z_4$ each independently represents CH or N), —S—CO—O—, —CH=CH—NH—, —CH=CH—S—, —CH=CH—O—, —N=CH—NH—, —CH$_2$—N=N—, —N=N—O—, —N=CH—S— or —O—CH$_2$CH$_2$—O—.

3. A method of treating bacterial infection comprising administering to a subject suffering from such an infection an effective amount of the compound of claim 1.

4. A method of treating bacterial infection comprising administering a subject suffering from such an infection an effective amount of the compound of claim 1 and an effective amount of a β-lactam-antibiotic or other antibacterial agent.

5. A method of overcoming bacterial resistances comprising administering a subject an effective amount of the compound of claim 1 and an effective amount of β-lactam-antibiotic or other antibacterial agent.

6. A pharmaceutical composition comprising the compound of claim 1 and a pharmaceutically acceptable carrier.

7. A pharmaceutical composition comprising the compound of claim 1, a β-lactam-antibiotic; and a pharmaceutically acceptable carrier.

8. A compound represented by formula A(XIII):

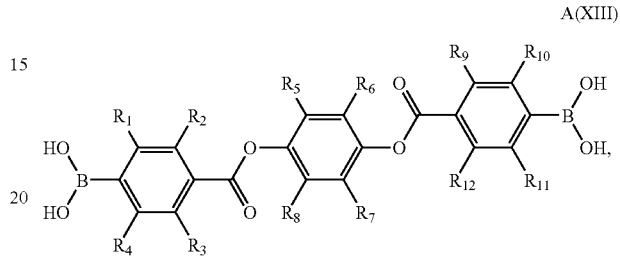

A(XIII)

wherein $R_1$ through $R_{12}$ are each independently hydrogen, $C_{1-6}$ alkyl, $C_{3-6}$ cycloalkyl, $C_{1-3}$ alkoxy, n-butoxy, i-butoxy, sec-butoxy, $R_{13}R_{14}N$— (wherein $R_{13}$ and $R_{14}$ are each independently hydrogen or $C_{1-3}$ alkyl), trifluoromethyl, trifluoromethoxy, difluoromethoxy, fluoro, chloro, bromo, cyano, acetyl, amino, borono, nitro, carboxyl, $C_{1-6}$ alkoxycarbonyl, phenyl, phenoxy, phenoxycarbonyl, benzyloxy, hydroxyl, trimethylsilyloxy, diphenyl-t-butylsilyloxy, hydroxymethyl, —SO$_3$H, —SO$_2$CH$_3$, —SO$_2$NHR$_{15}$ (wherein $R_{15}$ is hydrogen or $C_{1-3}$ alkyl), or —O(CH$_2$)$_n$OR$_{16}$— (wherein $R_{16}$ is hydrogen or $C_{1-3}$ alkyl, and n is 1, 2 or 3); or when any two $R_i$s are located at the ortho position to each other, they together form $-Z_1=Z_2-Z_3=Z_4$- (wherein $Z_1$ through $Z_4$ each independently represents CH or N), —S—CO—O—, —CH=CH—NH—, —CH=CH—S—, —CH=CH—O—, —N=CH—NH—, —CH$_2$—N=N—, —N=N—O—, —N=CH—S— or —O—CH$_2$CH$_2$—O—.

9. The compound of claim 8 wherein
$R_1$, $R_3$, $R_4$, $R_9$, $R_{11}$ and $R_{12}$ are each hydrogen;
$R_2$ and $R_{10}$ are each independently hydrogen, fluoro, chloro, bromo, cyano, acetyl, nitro, amino, borono, carboxyl, $C_{1-4}$ alkoxycarbonyl, phenoxycarbonyl, hydroxyl, —SO$_3$H, —SO$_2$CH$_3$ and —SO$_2$NH$_2$;
$R_5$ through $R_8$ are each independently hydrogen, $C_{1-4}$ alkyl, $C_{3-6}$ cycloalkyl, $C_{1-3}$ alkoxy, trifluoromethyl, fluoro, chloro, bromo, cyano, acetyl, amino, borono, nitro, carboxyl, $C_{1-4}$ alkoxycarbonyl, phenyl, phenoxy, phenoxycarbonyl, benzyloxy, hydroxyl, hydroxymethyl, —SO$_3$H, —SO$_2$CH$_3$, —SO$_2$NH$_2$, or when any two $R_i$s are located at the ortho position to each other, they together form $-Z_1=Z_2-Z_3=Z_4$- (wherein $Z_1$ through $Z_4$ each independently represents CH or N), —S—CO—O—, —CH=CH—NH—, —CH=CH—S—, —CH=CH—O—, —N=CH—NH—, —CH$_2$—N=N—, —N=N—O—, —N=CH—S— or —O—CH$_2$CH$_2$—O—.

10. A method of treating bacterial infection comprising administering to a subject suffering from such an infection an effective amount of the compound of claim 8.

11. A method of treating bacterial infection comprising administering a subject suffering from such an infection an effective amount of the compound of claim 8 and an effective amount of a β-lactam-antibiotic or other antibacterial agent.

12. A method of overcoming bacterial resistances comprising administering a subject an effective amount of the compound of claim 8 and an effective amount of a β-lactam-antibiotic or other antibacterial agent.

13. A pharmaceutical composition comprising the compound of claim 8 and a pharmaceutically acceptable carrier.

14. A pharmaceutical composition comprising the compound of claim 8, a β-lactam-antibiotic; and a pharmaceutically acceptable carrier.

15. A compound represented by formula A(XV):

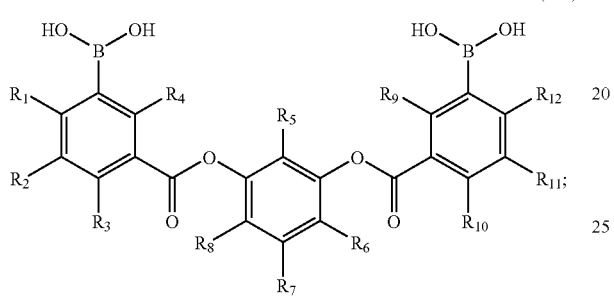

wherein $R_1$ through $R_9$ are each independently hydrogen, $C_{1-6}$ alkyl, $C_{3-6}$ cycloalkyl, $C_{1-3}$ alkoxy, n-butoxy, i-butoxy, sec-butoxy, $R_{13}R_{14}N$— (wherein $R_{13}$ and $R_{14}$ are each independently hydrogen or $C_{1-3}$ alkyl), trifluoromethyl, trifluoromethoxy, difluoromethoxy, fluoro, chloro, bromo, cyano, acetyl, nitro, amino, borono, carboxyl, $C_{1-6}$ alkoxycarbonyl, phenyl, phenoxy, phenoxycarbonyl, benzyloxy, hydroxyl, trimethylsilyloxy, diphenyl-t-butylsilyloxy, hydroxymethyl, —$SO_3H$, —$SO_2CH_3$, —$SO_2NHR_{15}$ (wherein $R_{15}$ is hydrogen or $C_{1-3}$ alkyl), or —$O(CH_2)_nOR_{16}$— (wherein $R_{16}$ is hydrogen or $C_{1-3}$ alkyl, and n is 1, 2 or 3); or when any two $R_i$ s are located at the ortho position to each other, they together form -$Z_1=Z_2-Z_3=Z_4$- (wherein $Z_1$ through $Z_4$ each independently represents CH or N), —S—CO—O—, —CH=CH—NH—, —CH=CH—S—, —CH=CH—O—, —N=CH—NH—, —$CH_2$—N=N—, —N=N—O—, —N=CH—S— or —O—$CH_2CH_2$—O—.

16. The compound of claim 15, wherein $R_1$, $R_3$, $R_4$, $R_9$, $R_{11}$ and $R_{12}$ are each hydrogen;

$R_2$ and $R_{10}$ are each independently hydrogen, fluoro, chloro, bromo, cyano, acetyl, nitro, amino, borono, carboxyl, $C_{1-4}$ alkoxycarbonyl, phenoxycarbonyl, hydroxyl, —$SO_3H$, —$SO_2CH_3$ and —$SO_2NH_2$;

$R_5$ through $R_8$ are each independently hydrogen, $C_{1-4}$ alkyl, $C_{3-6}$ cycloalkyl, $C_{1-3}$ alkoxy, trifluoromethyl, fluoro, chloro, bromo, cyano, acetyl, amino, borono, nitro, carboxyl, $C_{1-4}$ alkoxycarbonyl, phenyl, phenoxy, phenoxycarbonyl, benzyloxy, hydroxyl, hydroxymethyl, —$SO_3H$, —$SO_2CH_3$, —$SO_2NH_2$, or when any two $R_i$ s are located at the ortho position to each other, they together form -$Z_1=Z_2-Z_3=Z_4$- (wherein $Z_1$ through $Z_4$ each independently represents CH or N), —S—CO—O—, —CH=CH—NH—, —CH=CH—S—, —CH=CH—O—, —N=CH—NH—, —$CH_2$—N=N—, —N=N—O—, —N=CH—S— or —O—$CH_2CH_2$—O—.

17. A method of treating bacterial infection comprising administering to a subject suffering from such an infection an effective amount of the compound of claim 15.

18. A method of treating bacterial infection comprising administering a subject suffering from such an infection an effective amount of the compound of claim 15 and an effective amount of a β-lactam-antibiotic or other antibacterial agent.

19. A method of overcoming bacterial resistances comprising administering a subject an effective amount of the compound of claim 15 and an effective amount of a β-lactam-antibiotic or other antibacterial agent.

20. A pharmaceutical composition comprising the compound of claim 15 and a pharmaceutically acceptable carrier.

21. A pharmaceutical composition comprising the compound of claim 15, a β-lactam-antibiotic; and a pharmaceutically acceptable carrier.

* * * * *